(12) United States Patent  
Ohashi et al.

(10) Patent No.: US 7,998,657 B2
(45) Date of Patent: Aug. 16, 2011

(54) ESTER COMPOUNDS AND THEIR PREPARATION, POLYMERS, RESIST COMPOSITIONS AND PATTERNING PROCESS

(75) Inventors: Masaki Ohashi, Joetsu (JP); Takeshi Kinsho, Joetsu (JP); Takeru Watanabe, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 12/912,161

(22) Filed: Oct. 26, 2010

(65) Prior Publication Data

US 2011/0039204 A1 Feb. 17, 2011

Related U.S. Application Data

(62) Division of application No. 11/822,441, filed on Jul. 5, 2007, now Pat. No. 7,902,385.

(30) Foreign Application Priority Data

Jul. 6, 2006 (JP) .................................. 2006-186298

(51) Int. Cl.
*G03F 7/004* (2006.01)
*G03F 7/30* (2006.01)
*C08F 124/00* (2006.01)
*C08F 224/00* (2006.01)

(52) U.S. Cl. ............... 430/270.1; 430/326; 430/910; 526/268; 526/269; 526/281; 526/284

(58) Field of Classification Search ............... 430/270.1, 430/326, 910; 526/268, 269, 281, 284
See application file for complete search history.

(56) References Cited

U.S. PATENT DOCUMENTS

| | | | |
|---|---|---|---|
| 4,491,628 A | 1/1985 | Ito et al. | |
| 4,603,101 A | 7/1986 | Crivello | |
| 5,188,585 A | 2/1993 | Peters | |
| 5,714,625 A | 2/1998 | Hada et al. | |
| 6,004,724 A | 12/1999 | Yamato et al. | |
| 6,063,953 A | 5/2000 | Hada et al. | |
| 6,114,083 A * | 9/2000 | Kawamura et al. | 430/270.1 |
| 6,261,738 B1 | 7/2001 | Asakura et al. | |
| 6,692,888 B1 | 2/2004 | Barclay et al. | |

(Continued)

FOREIGN PATENT DOCUMENTS

JP 5-88367 A 1/1990

(Continued)

OTHER PUBLICATIONS

Allen et al., "Single Layer Resists with Enhanced ETCH Resistance for 193nm Lithography," Journal of Photopolymer Science and Technology, vol. 7, No. 3, 1994, pp. 507-516.

Arimitsu et al., "Effect of Phenolic Hydroxyl Residues on the Improvement of Acid-Proliferation-Type Photoimaging Materials," Journal of Photopolymer Science and Technology, vol. 9, No. 1, 1996, pp. 29-30.

(Continued)

*Primary Examiner* — John S Chu
(74) *Attorney, Agent, or Firm* — Birch, Stewart, Kolasch & Birch, LLP

(57) ABSTRACT

Novel ester compounds having formulae (1) to (4) wherein $A^1$ is a polymerizable functional group having a carbon-carbon double bond, $A^2$ is oxygen, methylene or ethylene, $R^1$ is a monovalent hydrocarbon group, $R^2$ is H or a monovalent hydrocarbon group, any pair of $R^1$ and/or $R^2$ may form an aliphatic hydrocarbon ring, $R^3$ is a monovalent hydrocarbon group, and n is 0 to 6 are polymerizable into polymers. Resist compositions comprising the polymers as a base resin are thermally stable and sensitive to high-energy radiation, have excellent sensitivity and resolution, and lend themselves to micropatterning with electron beam or deep-UV.

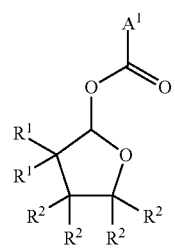

(1)

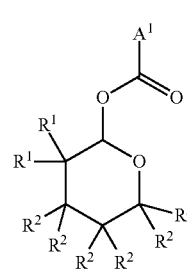

(2)

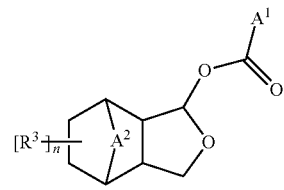

(3)

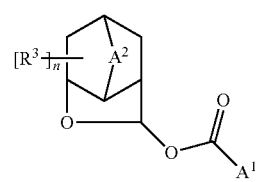

(4)

7 Claims, No Drawings

U.S. PATENT DOCUMENTS 6,916,591 B2 7/2005 Ohsawa et al.

FOREIGN PATENT DOCUMENTS

| JP | 62-115440 A | 3/1990 |
| --- | --- | --- |
| JP | 2-27660 B2 | 6/1990 |
| JP | 2-19847 A | 8/1992 |
| JP | 2-80515 A | 4/1993 |
| JP | 9-95479 A | 4/1997 |
| JP | 9-230588 A | 9/1997 |
| JP | 9-301948 A | 11/1997 |
| JP | 2906999 B2 | 4/1999 |
| JP | 4-215661 A | 11/2000 |
| JP | 2000/314956 A | 11/2000 |
| WO | WO 2004-074242 A3 | 9/2004 |

OTHER PUBLICATIONS

Arimitsu et al., "Sensitivity Enhancement of Chemical-Amplification-Type Photoimaging Materials by Acetoacetic Acid Derivatives," Journal of Photopolymer Science and Technology, vol. 8, No. 1, 1995, pp. 43-44.

* cited by examiner

ESTER COMPOUNDS AND THEIR PREPARATION, POLYMERS, RESIST COMPOSITIONS AND PATTERNING PROCESS

CROSS-REFERENCE TO RELATED APPLICATION

This application is a Divisional of pending U.S. application Ser. No. 11/822,441, filed on Jul. 5, 2007, now U.S. Pat. No. 7,902,385 which claims the benefit of Japanese Application No. 2006-186298, filed on Jul. 6, 2006, both of which are hereby incorporated by reference as fully set forth herein.

TECHNICAL FIELD

This invention relates to (1) a novel ester compound, (2) a polymer comprising units derived from the ester compound which is blended as a base resin to formulate a chemically amplified resist composition suitable in the micropatterning technology, (3) a resist composition comprising the polymer, and (4) a patterning process using the resist composition.

BACKGROUND OF THE INVENTION

While a number of recent efforts are being made to achieve a finer pattern rule in the drive for higher integration and operating speeds in LSI devices, deep-ultraviolet lithography is thought to hold particular promise as the next generation in microfabrication technology. In particular, photolithography using a KrF or ArF excimer laser as the light source is strongly desired to reach the practical level as the micropatterning technique capable of achieving a feature size of 0.3 μm or less.

For resist materials for use with a KrF excimer laser, polyhydroxystyrene having a practical level of transmittance and etching resistance is, in fact, a standard base resin. For resist materials for use with an ArF excimer laser, polyacrylic or polymethacrylic acid derivatives and polymers comprising cycloaliphatic compounds in the backbone are under investigation. In either case, the basic concept is that some or all of alkali soluble sites of alkali soluble resin are protected with acid labile groups. The overall performance of resist material is adjusted by a choice from among a variety of acid labile groups.

Exemplary acid labile groups include tert-butoxycarbonyl (JP-B 2-27660), tert-butyl (JP-A 62-115440 and J. Photopolym. Sci. Technol. 7 [3], 507 (1994)), 2-tetrahydropyranyl (JP-A 2-80515 and JP-A 5-88367), and 1-ethoxyethyl (JP-A 2-19847 and JP-A 4-215661). While it is desired to achieve a finer pattern rule, none of these acid labile groups are deemed to exert satisfactory performance.

More particularly, tert-butoxycarbonyl and tert-butyl are extremely less reactive with acids so that a substantial quantity of energy radiation must be irradiated to generate a sufficient amount of acid in order to establish a difference in rate of dissolution before and after exposure. If a photoacid generator of the strong acid type is used, the exposure can be reduced to a relatively low level because reaction can proceed with a small amount of acid generated. However, in this event, the deactivation of the generated acid by air-borne basic substances has a relatively large influence, giving rise to such problems as a T-top pattern. On the other hand, 2-tetrahydropyranyl and 1-ethoxyethyl are so reactive with acids that with only the acid generated by exposure, elimination reaction may randomly proceed without wait until heat treatment, resulting in substantial dimensional changes between exposure and heat treatment/development. Where these groups are used as protective groups for carboxylic acid, they have a low inhibiting effect to alkali dissolution, resulting in a high rate of dissolution in unexposed areas and film thinning during development. If highly substituted polymers are used to avoid such inconvenience, there results an extreme drop of heat resistance. These resins fail to provide a difference in rate of dissolution before and after exposure, resulting in resist materials having a very low resolution.

In case where 2-adamantyloxymethyl is used as the protective group for carboxylic acid, its performance is good with respect to sensitivity and resolution, but such a protective group of methylene acetal type gives off formaldehyde having a low boiling point after deprotection, leaving the risk of lens contamination by outgassing. While a further reduction of pattern feature size is being demanded, there is a need to have a resist material which is not only satisfactory in sensitivity, resolution, and etch resistance, but also minimized in outgassing.

DISCLOSURE OF THE INVENTION

Therefore, an object of the present invention is to provide (1) a novel ester compound having a good acid-decomposition ability and high thermal stability and a method for preparing the same, (2) a polymer which is blended as a base resin to formulate a resist composition having a high sensitivity and resolution as well as minimized outgassing, (3) a resist composition comprising the polymer as a base resin, and (4) a patterning process using the resist composition.

It has been found that ester compounds of the general formulae (1) to (4), shown below, can be prepared in high yields by a simple method to be described later; that polymers obtained using the ester compounds have high transparency at the exposure wavelength of an excimer laser; that resist compositions comprising the polymers as the base resin have a high sensitivity, high resolution and high thermal stability; and that these resist compositions lend themselves to precise micropatterning.

In one aspect, the invention provides a polymerizable ester compound having any one of the following general formulae (1) to (4).

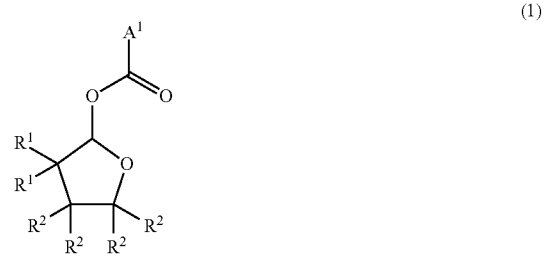

(1)

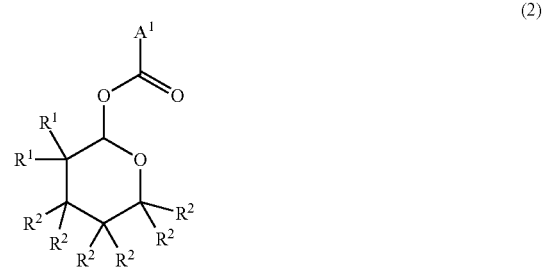

(2)

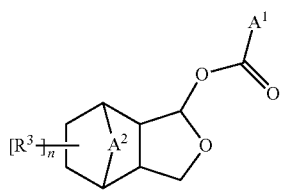
(3)

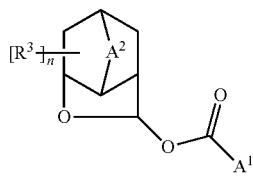
(4)

Herein $A^1$ is a polymerizable functional group having a carbon-carbon double bond, $A^2$ is an oxygen atom, methylene or ethylene group, $R^1$ is each independently a straight, branched or cyclic monovalent hydrocarbon group of 1 to 10 carbon atoms, $R^2$ is each independently a hydrogen atom or a straight, branched or cyclic monovalent hydrocarbon group of 1 to 10 carbon atoms, or a combination of $R^1$, a combination of $R^2$, or a combination of $R^1$ and $R^2$ may bond together to form an aliphatic hydrocarbon ring with some carbon atoms in the oxygen heterocycle to which they are attached, and in that event, each of $R^1$ and $R^2$ is a straight, branched or cyclic alkylene group of 1 to 10 carbon atoms, $R^3$ is each independently a straight, branched or cyclic monovalent hydrocarbon group of 1 to 10 carbon atoms, or a combination of $R^3$ may bond together to form an aliphatic hydrocarbon ring with some carbon atoms in the ring to which they are attached, and in that event, each of $R^3$ is a straight, branched or cyclic alkylene group of 1 to 10 carbon atoms, and n is an integer of 0 to 6.

The preferred ester compounds have the following general formulae (5) to (8):

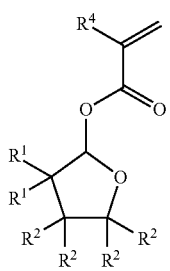
(5)

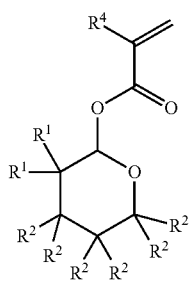
(6)

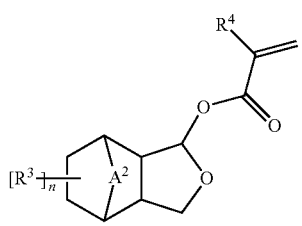
(7)

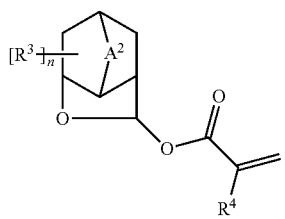
(8)

wherein $A^1$, $R^1$, $R^2$, $R^3$ and n are as defined above, and $R^4$ is hydrogen, fluorine, methyl or trifluoromethyl.

Also the preferred ester compounds have the following general formulae (9) to (12):

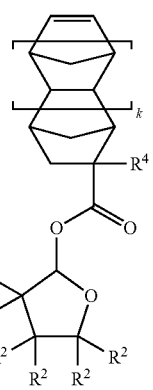
(9)

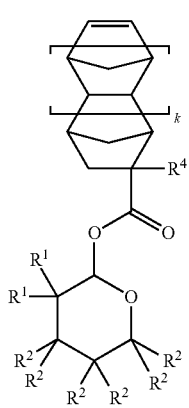
(10)

-continued

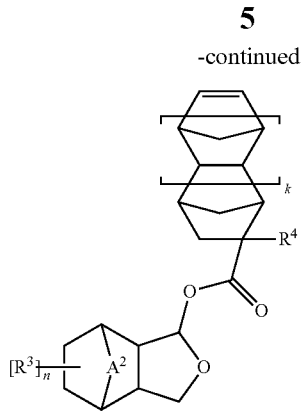
(11)

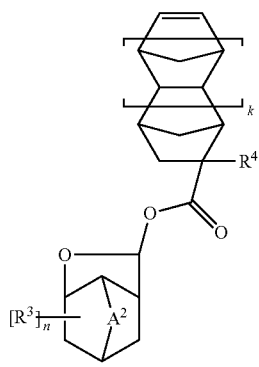
(12)

wherein $A^2$, $R^1$, $R^2$, $R^3$, $R^4$, and n are as defined above, and k is 0 or 1.

In a second aspect, the invention provides a method for preparing a polymerizable ester compound having the general formula (1) or (2), comprising the steps of reacting an imine compound having the general formula (21) with a compound having the general formula (22) or (23) to form a hydroxyl-containing imine compound having the general formula (24) or (25); subjecting the hydroxyl-containing imine compound to acid hydrolysis to form a hemiacetal compound having the general formula (17) or (18); and acylating the hemiacetal compound to form a polymerizable ester compound having the general formula (1) or (2).

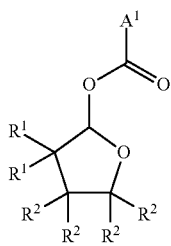
(1)

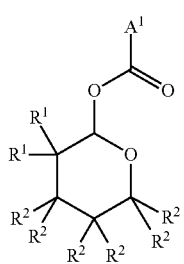
(2)

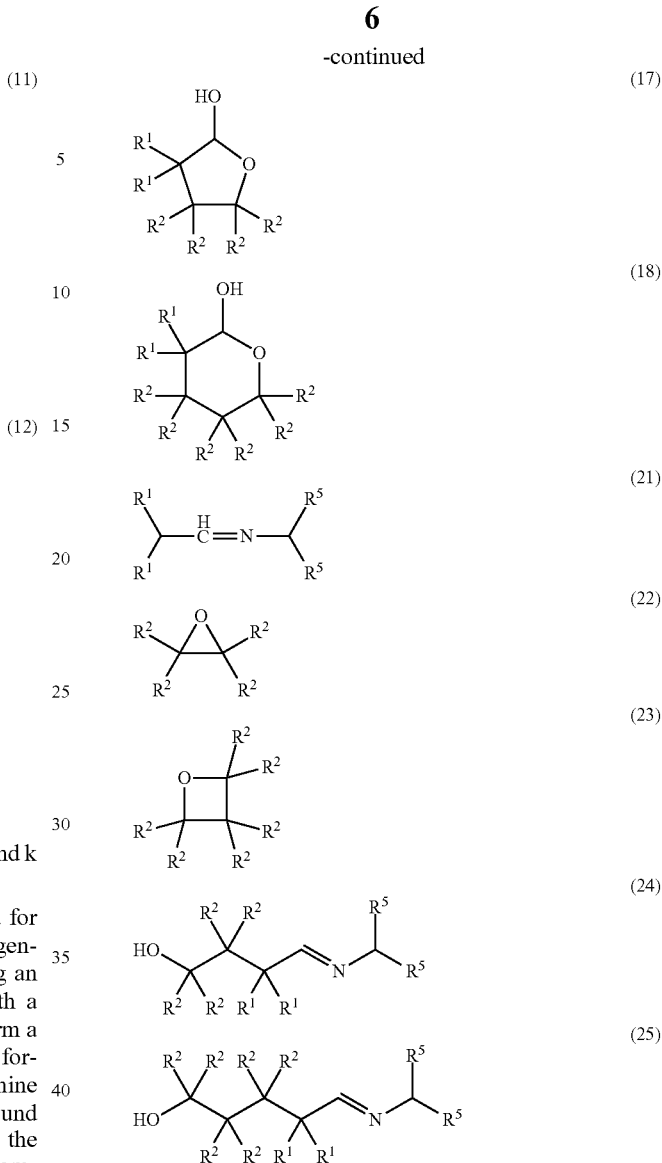

Herein $A^1$ is a polymerizable functional group having a carbon-carbon double bond, $R^1$ is each independently a straight, branched or cyclic monovalent hydrocarbon group of 1 to 10 carbon atoms, $R^2$ is each independently a hydrogen atom or a straight, branched or cyclic monovalent hydrocarbon group of 1 to 10 carbon atoms, or a combination of $R^1$, a combination of $R^2$, or a combination of $R^1$ and $R^2$ may bond together to form an aliphatic hydrocarbon ring with some carbon atoms in the oxygen heterocycle to which they are attached, and in that event, each of $R^1$ and $R^2$ is a straight, branched or cyclic alkylene group of 1 to 10 carbon atoms, and $R^5$ is each independently a straight, branched or cyclic monovalent hydrocarbon group of 1 to 10 carbon atoms, or a combination of $R^5$ may bond together to form an aliphatic hydrocarbon ring with the carbon atom to which they are attached.

In a third aspect, the invention provides a polymer comprising at least recurring units derived from the polymerizable ester compound defined above and having a weight average molecular weight of 2,000 to 100,000.

In a preferred embodiment, the polymer further comprises recurring units of at least one type selected from the following general formula (R1).

(R1)

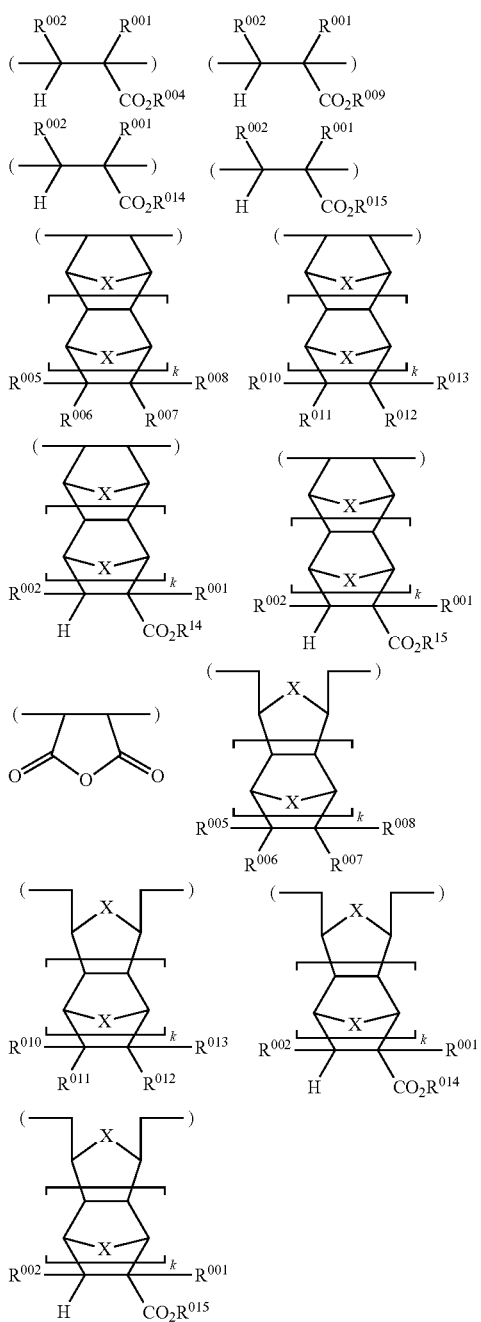

Herein $R^{001}$ is hydrogen, fluorine, methyl, trifluoromethyl or $CH_2CO_2R^{003}$. $R^{002}$ is hydrogen, methyl or $CO_2R^{003}$. $R^{003}$ is a straight, branched or cyclic $C_1$-$C_{15}$ alkyl group. $R^{004}$ is hydrogen or a monovalent hydrocarbon group of 1 to 15 carbon atoms having at least one group selected from among fluorinated substituent groups, carboxyl, hydroxyl and cyano groups. At least one of $R^{005}$ to $R^{008}$ is a carboxyl group or a monovalent hydrocarbon group of 1 to 15 carbon atoms having at least one group selected from among fluorinated substituent groups, carboxyl, hydroxyl and cyano groups while the remaining of $R^{005}$ to $R^{008}$ are each independently hydrogen or straight, branched or cyclic $C_1$-$C_{15}$ alkyl groups, or two of $R^{005}$ to $R^{008}$ may bond together to form an aliphatic hydrocarbon ring with the carbon atom(s) to which they are attached, and in that event, at least one of $R^{005}$ to $R^{008}$ is a divalent hydrocarbon group of 1 to 15 carbon atoms having at least one group selected from fluorinated substituent groups, carboxyl, hydroxyl and cyano groups while the remaining of $R^{005}$ to $R^{008}$ are each independently single bonds, hydrogen atoms or straight, branched or cyclic $C_1$-$C_{15}$ alkyl groups. $R^{009}$ is a monovalent hydrocarbon group of 3 to 15 carbon atoms containing a —$CO_2$— partial structure. At least one of $R^{010}$ to $R^{013}$ is a monovalent hydrocarbon group of 2 to 15 carbon atoms containing a —$CO_2$— partial structure while the remaining of $R^{010}$ to $R^{013}$ are each independently hydrogen atoms or straight, branched or cyclic $C_1$-$C_{15}$ alkyl groups, or two of $R^{010}$ to $R^{013}$ may bond together to form an aliphatic hydrocarbon ring with the carbon atom(s) to which they are attached, and in that event, at least one of $R^{010}$ to $R^{013}$ is a divalent hydrocarbon group of 1 to 15 carbon atoms having a —$CO_2$— partial structure while the remaining of $R^{010}$ to $R^{013}$ are each independently single bonds, hydrogen atoms or straight, branched or cyclic $C_1$-$C_{15}$ alkyl groups. $R^{014}$ is a polycyclic hydrocarbon group having 7 to 15 carbon atoms or an alkyl group containing such a polycyclic hydrocarbon group. $R^{015}$ is an acid labile group, X is $CH_2$ or an oxygen atom; and k is 0 or 1.

In the preferred polymer, the recurring units derived from the polymerizable ester compound of any one of formulae (1) to (4) are present in a molar fraction of at least 5%.

In a fourth aspect, the invention provides a resist composition comprising the polymer defined above; specifically, a resist composition comprising (A) the polymer, (B) an acid generator, and (C) an organic solvent; and more specifically a resist composition comprising (A) the polymer, (B) an acid generator, (C) an organic solvent, and (D) a sensitivity regulator.

In a fifth aspect, the invention provides a process for forming a pattern, comprising the steps of applying the resist composition defined above onto a substrate to form a resist coating; heat treating the coating and exposing to high-energy radiation or electron beam through a photomask; and optionally heat treating the exposed coating and developing with a developer.

It is noted that immersion lithography can be applied to the resist composition of the invention. The immersion lithography involves prebaking a resist film and exposing the resist film to light through a projection lens with a medium interposed between the resist film and the projection lens. The ArF immersion lithography uses deionized water as the immersion medium. This technology, combined with a projection lens having a numerical aperture of at least 1.0, is important for the ArF lithography to survive to the 65 nm node, with a further development thereof being accelerated.

The resist composition of the invention allows the feature size of the pattern after development to be reduced by various shrinkage techniques. For example, the hole size can be shrunk by such known techniques as thermal flow, RELACS, SAFIRE, and WASOOM. More effective shrinkage of hole size by thermal flow is possible particularly when the inventive polymer is blended with a hydrogenated cycloolefin ring-opening metathesis polymer (ROMP) having a low Tg.

BENEFITS OF THE INVENTION

A resist composition comprising a polymer resulting from the polymerizable ester compound of the invention as a base resin is thermally stable and sensitive to high-energy radiation, has excellent sensitivity and resolution, and lends itself to micropatterning with electron beam or deep-UV. Especially because of the minimized absorption at the exposure wavelength of an ArF or KrF excimer laser, a fine-feature pattern having sidewalls perpendicular to the substrate can easily be formed. Since no low-molecular-weight fractions are generated after deprotection, advantageously the level of outgassing is minimized.

DESCRIPTION OF THE PREFERRED EMBODIMENT

The singular forms "a," "an" and "the" include plural referents unless the context clearly dictates otherwise.

The notation (Cn-Cm) means a group containing from n to m carbon atoms per group.

Ester Compound

The ester compounds of the invention have the following general formulae (1) to (4):

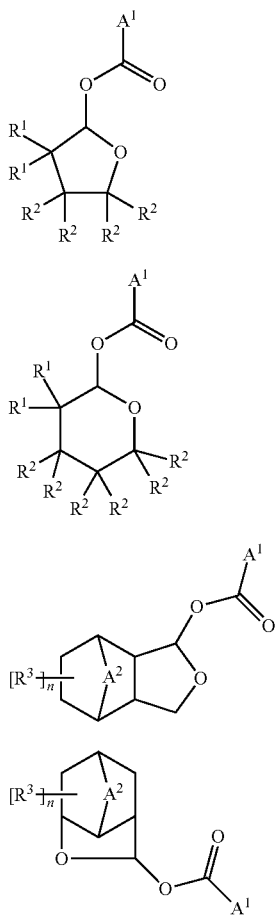

Herein $A^1$ is a polymerizable functional group having a carbon-carbon double bond, such as vinyl, allyl, 1-propenyl, isopropenyl, norbornenyl, and tetracyclo[4.4.0.1$^{2,5}$.1$^{7,10}$] dodecenyl. $A^2$ is an oxygen atom, methylene group or ethylene group. $R^1$ is each independently a straight, branched or cyclic monovalent hydrocarbon group of 1 to 10 carbon atoms, examples of which include methyl, ethyl, n-propyl, isopropyl, n-butyl, sec-butyl, tert-butyl, tert-amyl, n-pentyl, n-hexyl, cyclopentyl, cyclohexyl, bicyclo[2.2.1]heptyl, bicyclo[2.2.2]octyl, bicyclo[3.3.1]nonyl, bicyclo[4.4.0]decanyl, and adamantyl. $R^2$ is each independently a hydrogen atom or a straight, branched or cyclic monovalent hydrocarbon group of 1 to 10 carbon atoms, examples of which include hydrogen, methyl, ethyl, n-propyl, isopropyl, n-butyl, sec-butyl, tert-butyl, tert-amyl, n-pentyl, n-hexyl, cyclopentyl, cyclohexyl, bicyclo[2.2.1]heptyl, bicyclo[2.2.2]octyl, bicyclo[3.3.1]nonyl, bicyclo[4.4.0]decanyl, and adamantyl. Alternatively, a combination of $R^1$, a combination of $R^2$, or a combination of $R^1$ and $R^2$ may bond together to form an aliphatic hydrocarbon ring with some carbon atoms in the oxygen heterocycle to which they are attached, and in that event, each of $R^1$ and $R^2$ is a straight, branched or cyclic $C_1$-$C_{10}$ alkylene group. Examples of the hydrocarbon ring include cyclopropane, cyclobutane, cyclopentane, cyclohexane, bicyclo[2.2.1]heptane, bicyclo[2.2.2]octane, bicyclo[3.3.1]nonane, bicyclo[4.4.0]decane, and adamantane. $R^3$ is each independently a straight, branched or cyclic monovalent hydrocarbon group of 1 to 10 carbon atoms, examples of which include methyl, ethyl, n-propyl, isopropyl, n-butyl, sec-butyl, tert-butyl, tert-amyl, n-pentyl, n-hexyl, cyclopentyl, cyclohexyl, bicyclo [2.2.1]heptyl, bicyclo[2.2.2]octyl, bicyclo[3.3.1]nonyl, bicyclo[4.4.0]decanyl, and adamantyl. Alternatively, a combination of $R^3$ may bond together to form an aliphatic hydrocarbon ring with some carbon atoms in the ring to which they are attached, and in that event, each of $R^3$ is a straight, branched or cyclic $C_1$-$C_{10}$ alkylene group. Examples of the hydrocarbon ring include cyclopropane, cyclobutane, cyclopentane, cyclohexane, bicyclo[2.2.1]heptane, bicyclo[2.2.2] octane, bicyclo[3.3.1]nonane, bicyclo[4.4.0]decane, and adamantane. The subscript n is an integer of 0 to 6.

The ester compound of the invention is characterized in that deprotection occurs without beta-elimination. Provided that for formulae (1) to (4) and similar formulae, the acetal carbon atom sandwiched between two oxygen atoms is designated α-carbon, a carbon atom at a vicinal position to α-carbon is designated β-carbon, and a hydrogen atom on β-carbon is designated β-hydrogen, the term "β-elimination" as used herein means that deprotection occurs as a result of β-hydrogen being eliminated. For example, the following scheme illustrates the deprotection reaction of 2-tetrahydropyranyl ester by β-elimination mechanism.

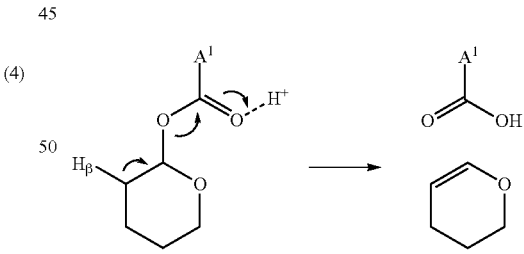

By contrast, in formulae (1) and (2), no hydrogen atoms are present on β-carbon. In formulae (3) and (4), hydrogen atoms may be present on β-carbon, but β-elimination cannot occur due to steric hindrance.

The deprotection mechanism other than the β-elimination that is deemed for the compounds of the invention and cyclic hemiacetal esters such as 2-tetrahydropyranyl esters to undergo is deprotection by hydrolysis or nucleophilic attack. For example, if a minute amount of water is present in the resist system, the compound of formula (1) undergoes acid hydrolysis into a carboxylic acid and a hemiacetal compound according to the scheme shown below.

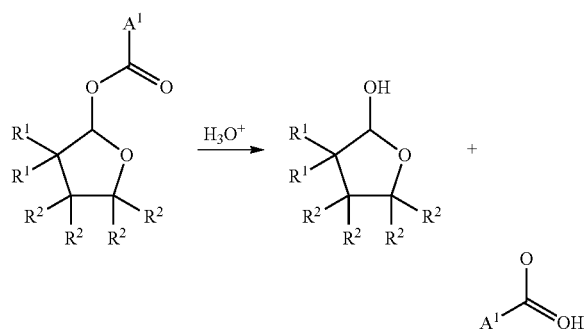

For the ester compounds of formulae (1) to (4), the probable deprotection mechanism is only deprotection by acid hydrolysis or nucleophilic attack. For 2-tetrahydropyranyl, 1-ethoxyethyl and analogous esters, not only deprotection by acid hydrolysis or nucleophilic attack, but also deprotection by the β-elimination mechanism can occur. Thus, the ester compounds of formulae (1) to (4) can be suppressed in reactivity for deprotection, as compared with the 2-tetrahydropyranyl, 1-ethoxyethyl and analogous esters.

The ester compounds of the invention are characterized by a cyclic hemiacetal ester structure, so that no low-molecular-weight fractions may be generated after deprotection. Therefore, when the ester compounds of the invention are used as a resist resin, an advantage of minimized outgassing is available.

Of the ester compounds having formulae (1) to (4), those having the following general formulae (5) to (8) are preferred.

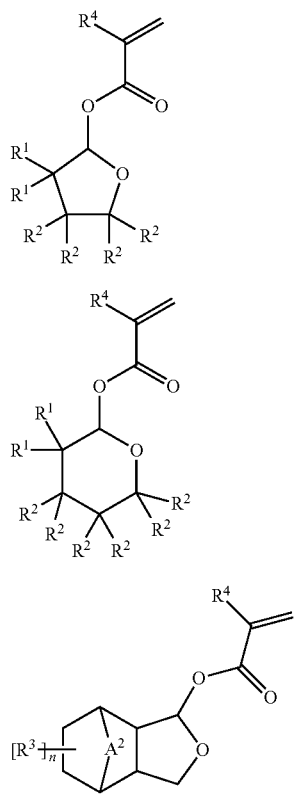

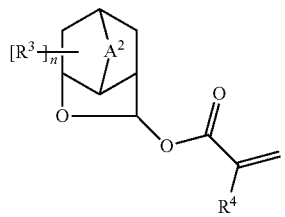

Herein $A^1$, $R^1$, $R^2$, $R^3$ and n are as defined above, and $R^4$ is a hydrogen atom, fluorine atom, methyl group or trifluoromethyl group.

Of the ester compounds having formulae (1) to (4), those having the following general formulae (9) to (12) are also preferred.

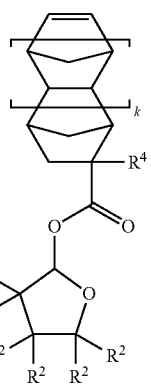

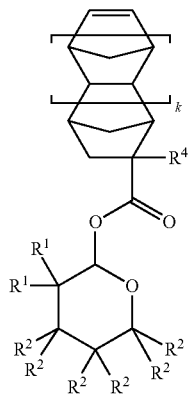

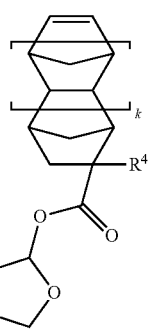

-continued
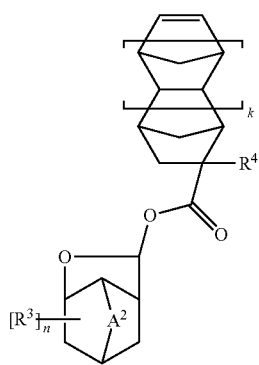
(12)
Herein $A^2$, $R^1$, $R^2$, $R^3$, $R^4$ and n are as defined above, and k is 0 or 1.
Illustrative non-limiting examples of the ester compounds having formulae (1) to (12) are given below.
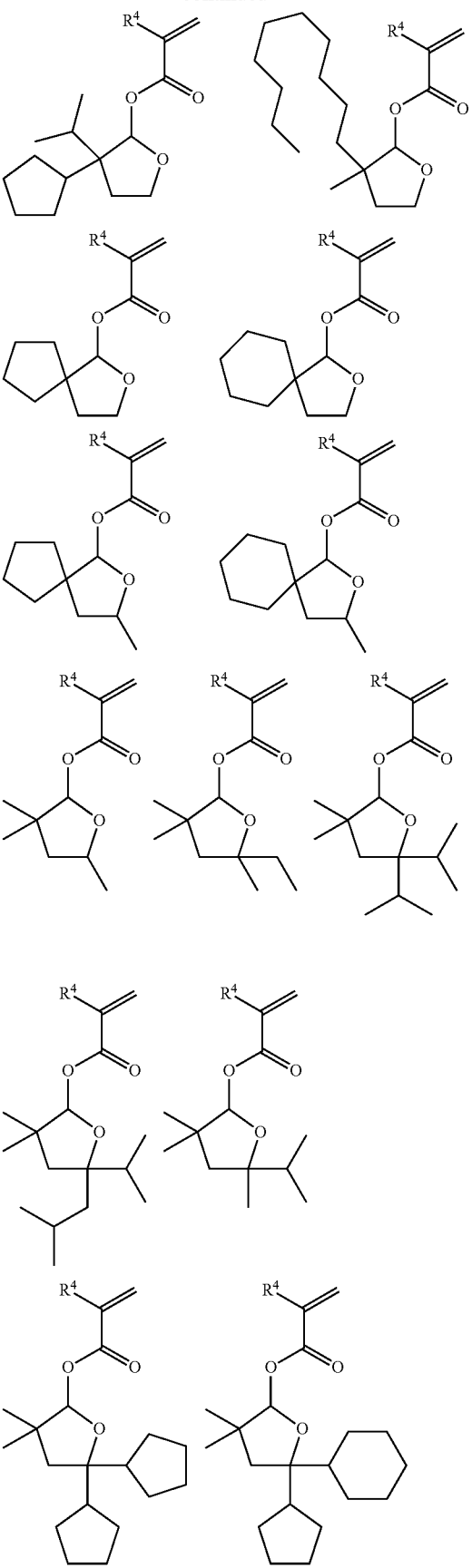

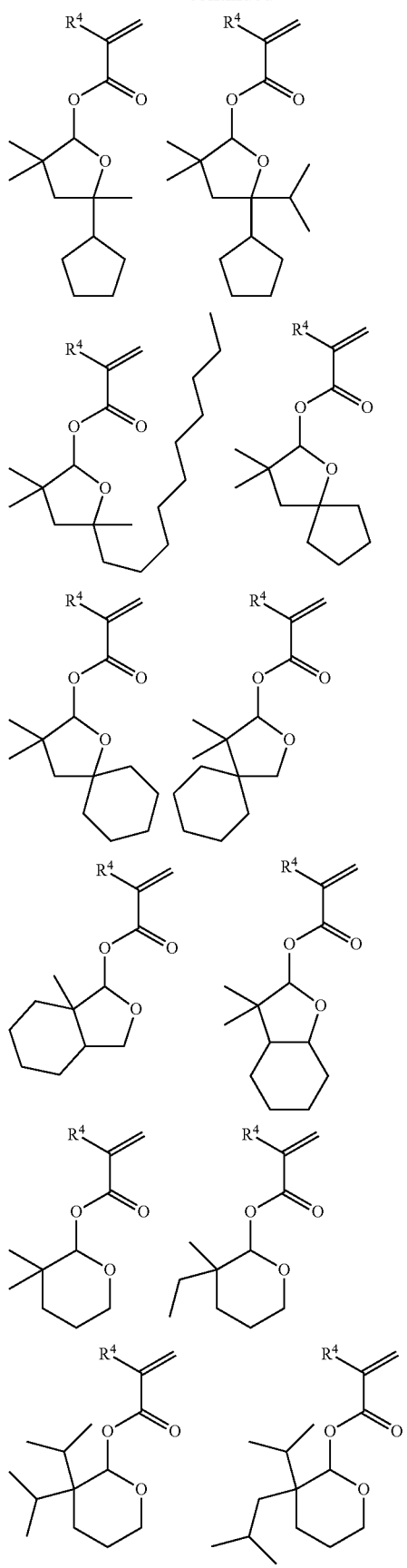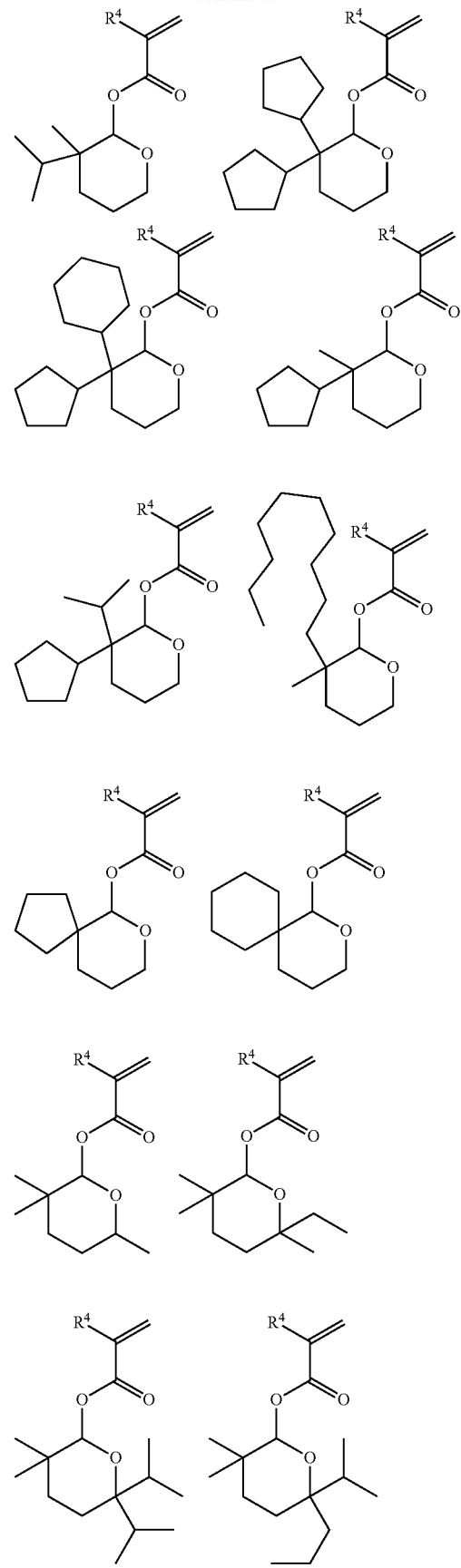

-continued
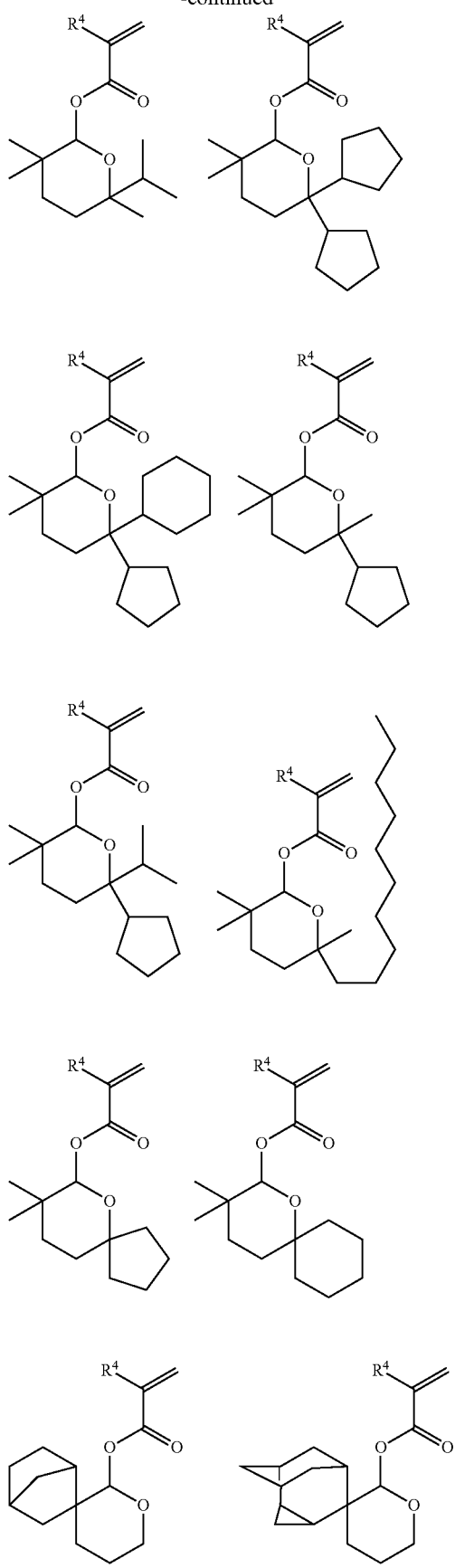
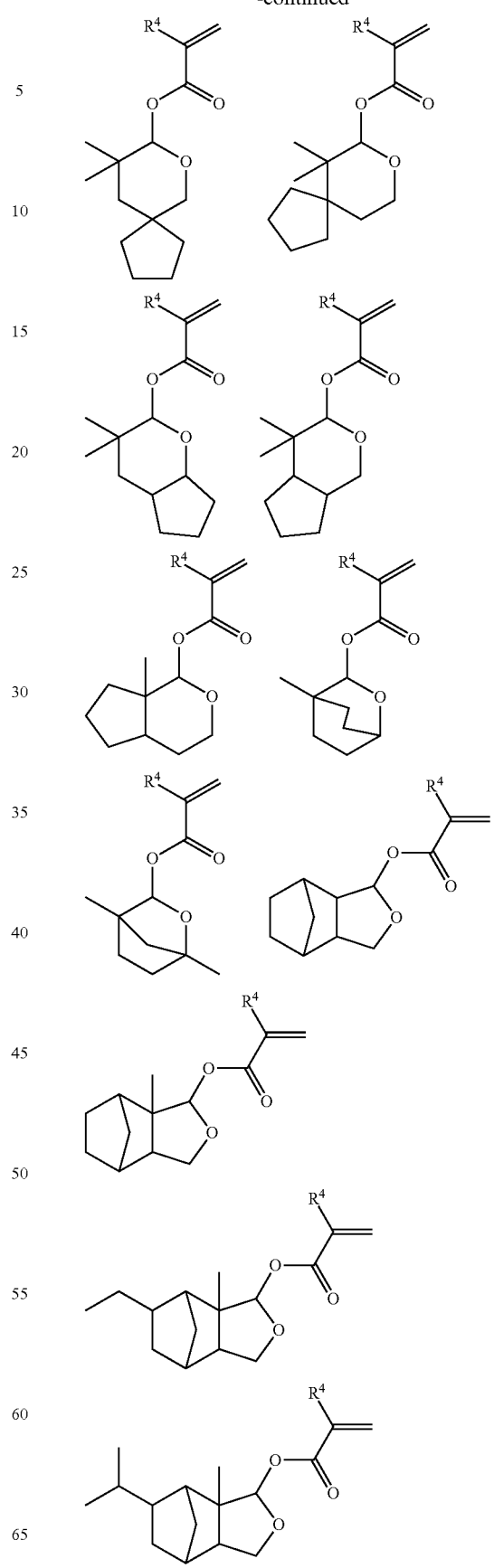

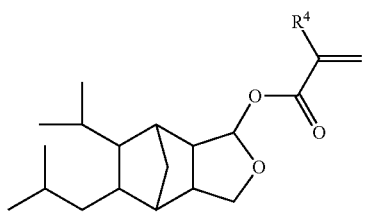
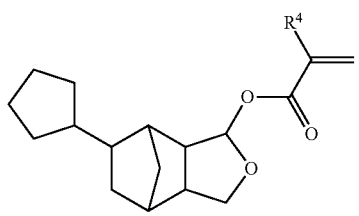
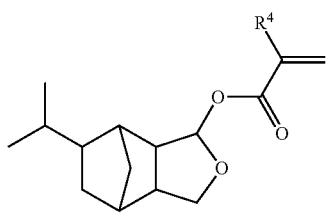
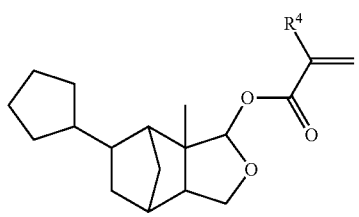
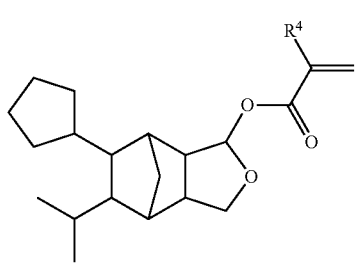
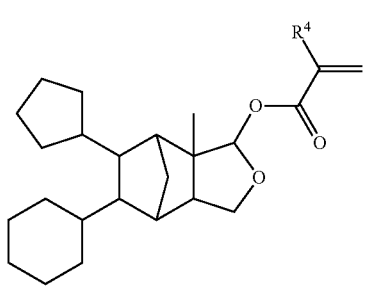
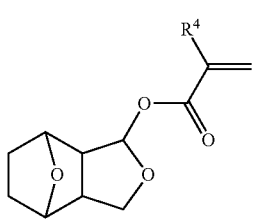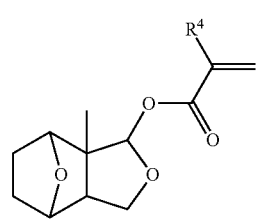
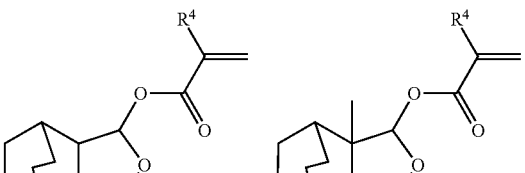
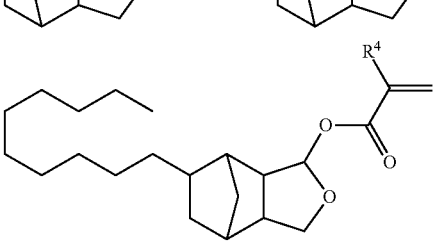
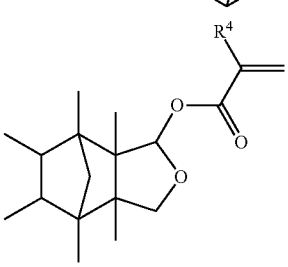
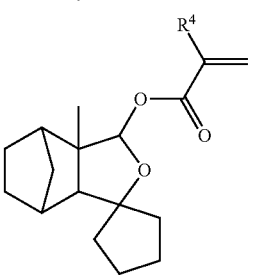
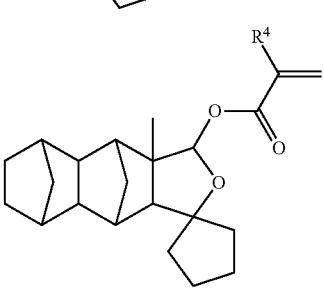
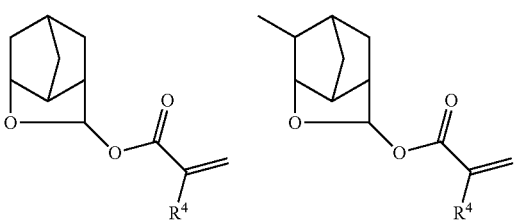
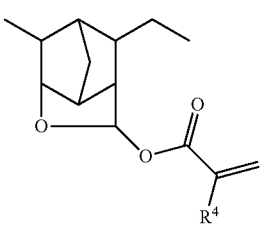

-continued
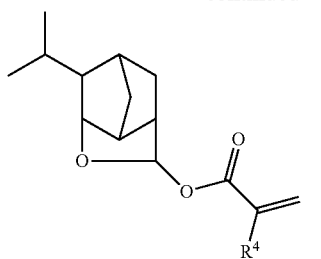
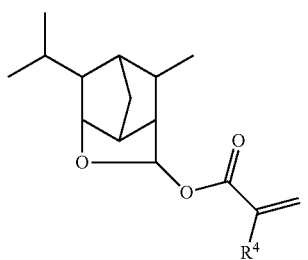
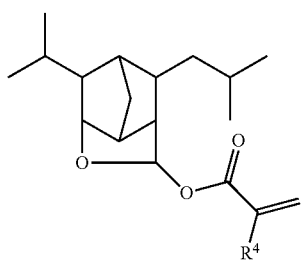
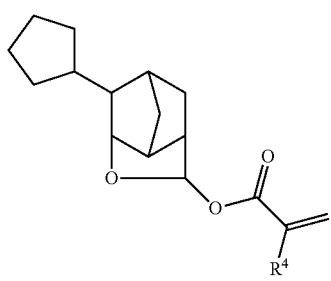
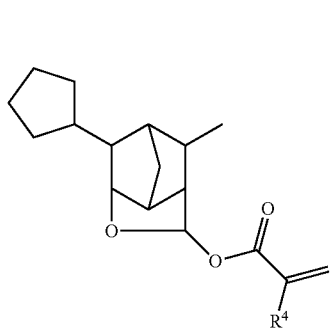
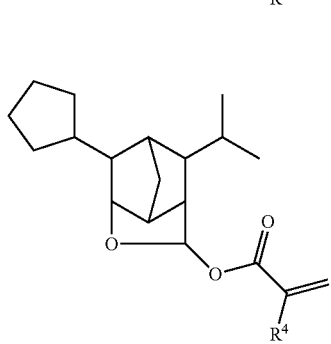
-continued
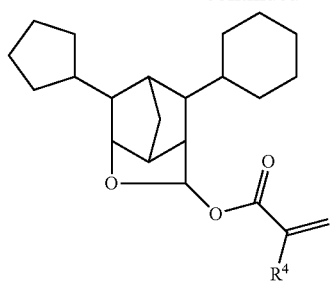
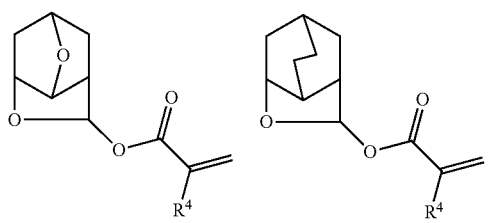
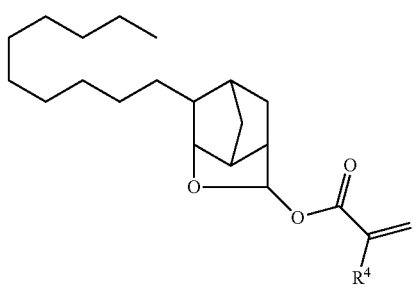
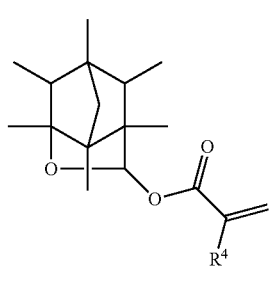
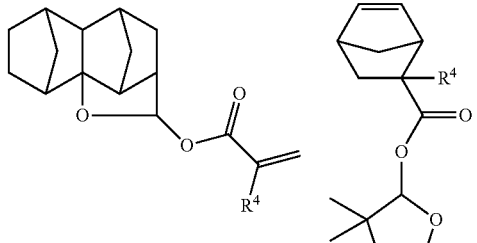
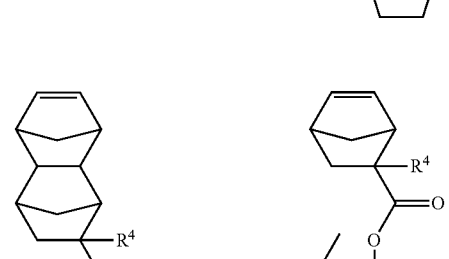
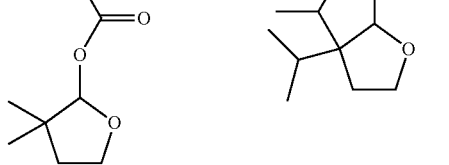

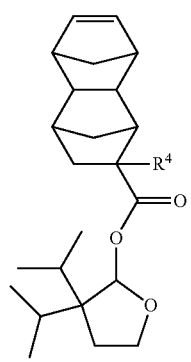
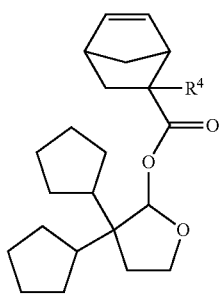
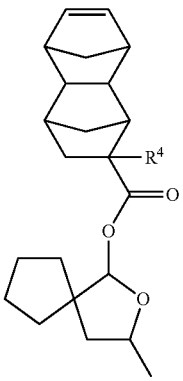
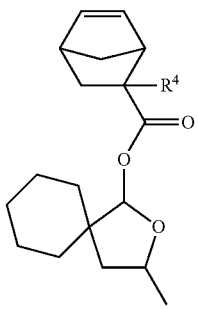
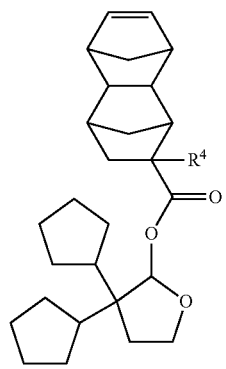
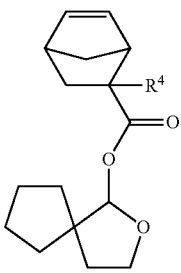
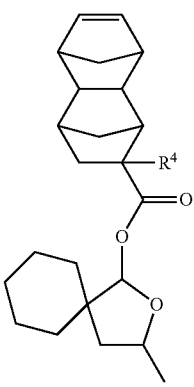
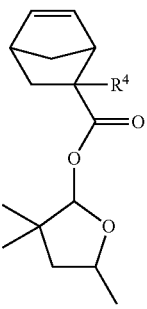
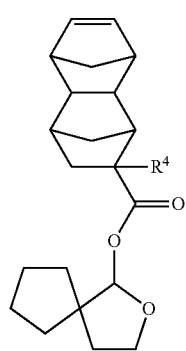
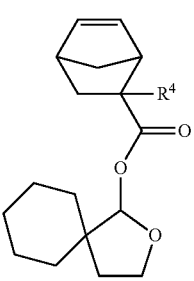
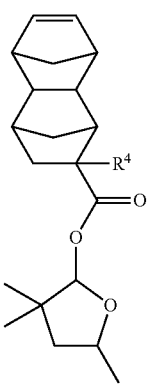
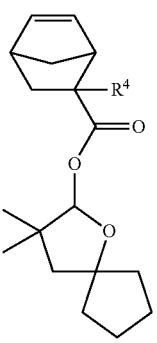
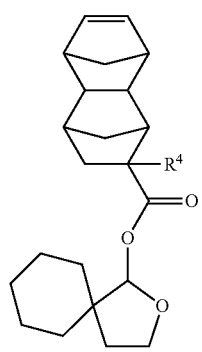
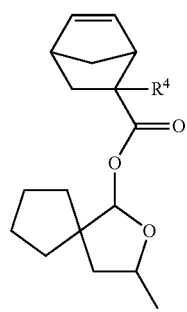
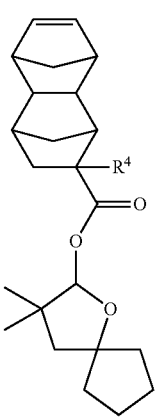
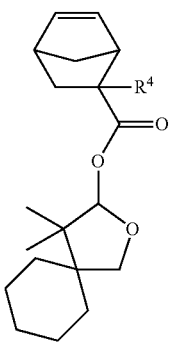

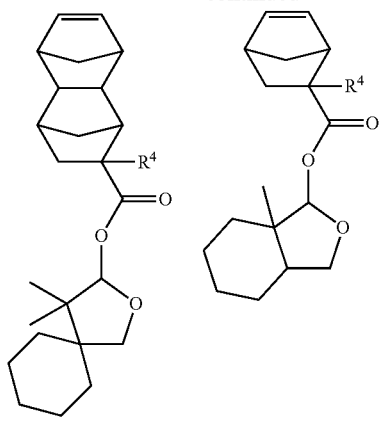
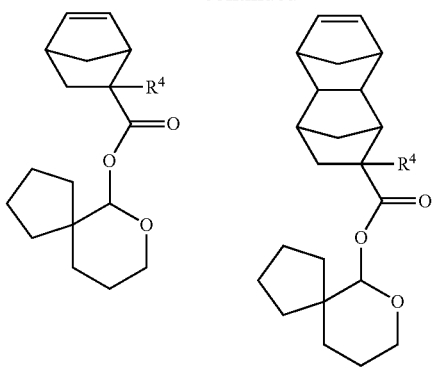
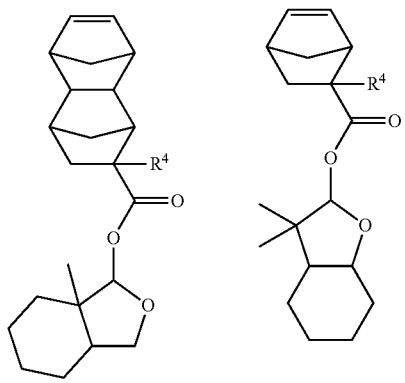
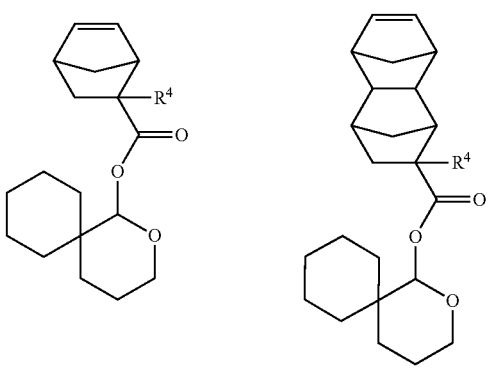
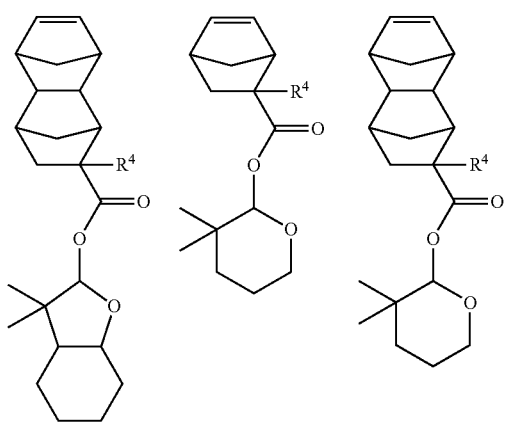
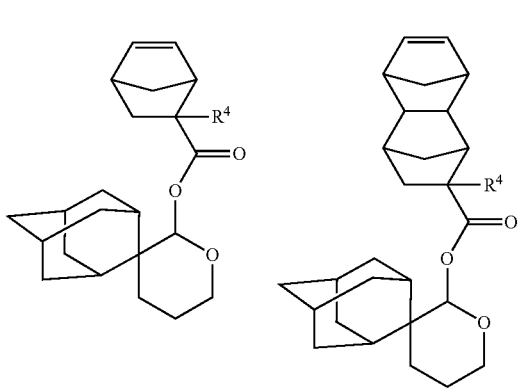
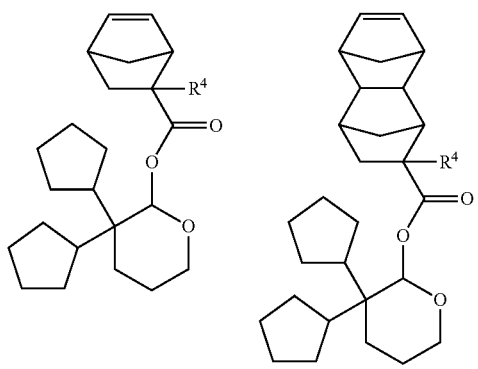
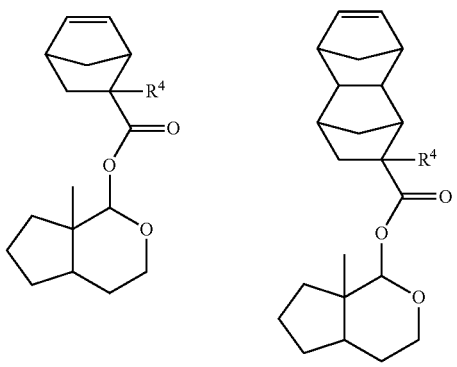

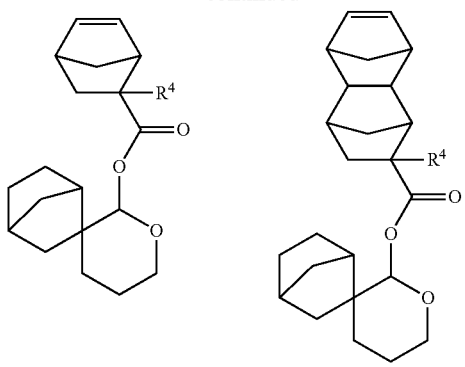
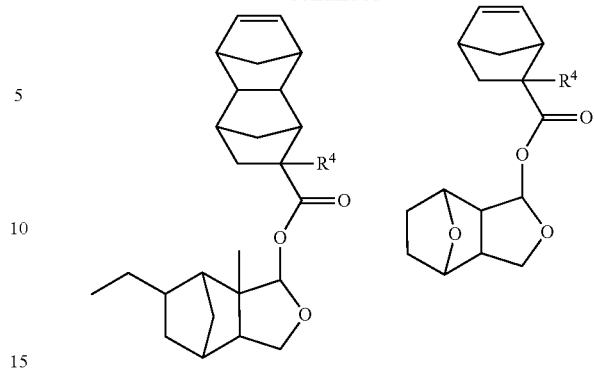
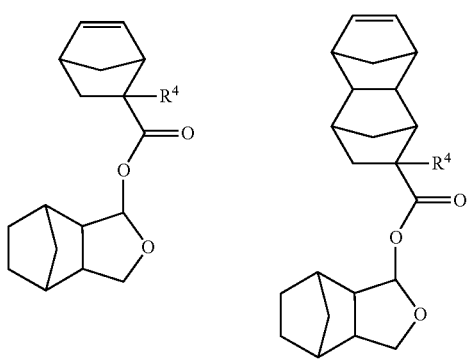
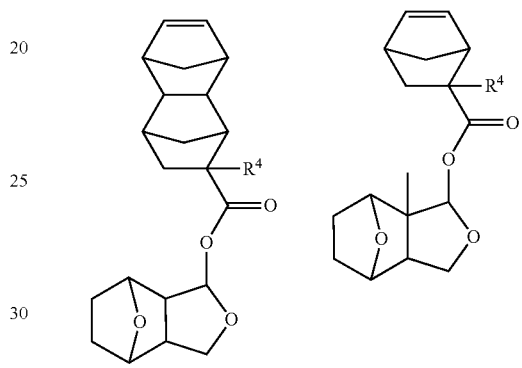
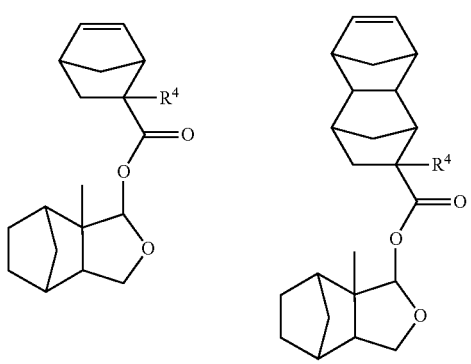
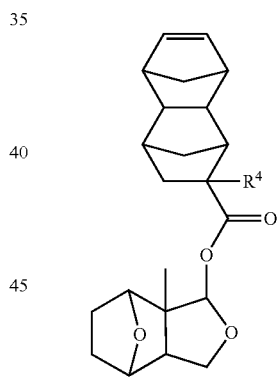
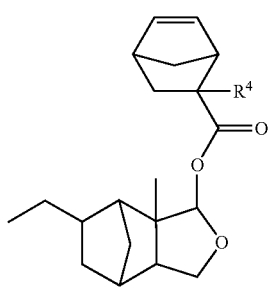

Herein $R^4$ is as defined above.

According to the invention, the ester compounds having formulae (1) and (2) may be synthesized, for example, as seen from the reaction scheme shown below, through the first step of synthesizing intermediate hemiacetal compounds having formulae (17) and (18) by procedure i) or ii), and the second step of acylating the hydroxyl group on the intermediate hemiacetal compounds by procedure iii) or iv). Also, the ester compounds having formulae (3) and (4) may be synthesized, for example, as seen from the reaction scheme shown below, through the first step of synthesizing intermediate hemiacetal compounds having formulae (19) and (20) by procedure i), and the second step of acylating the intermediate hemiacetal compounds by procedure iii) or iv). The method of preparing the ester compounds having formulae (1) to (4) is not limited to these.

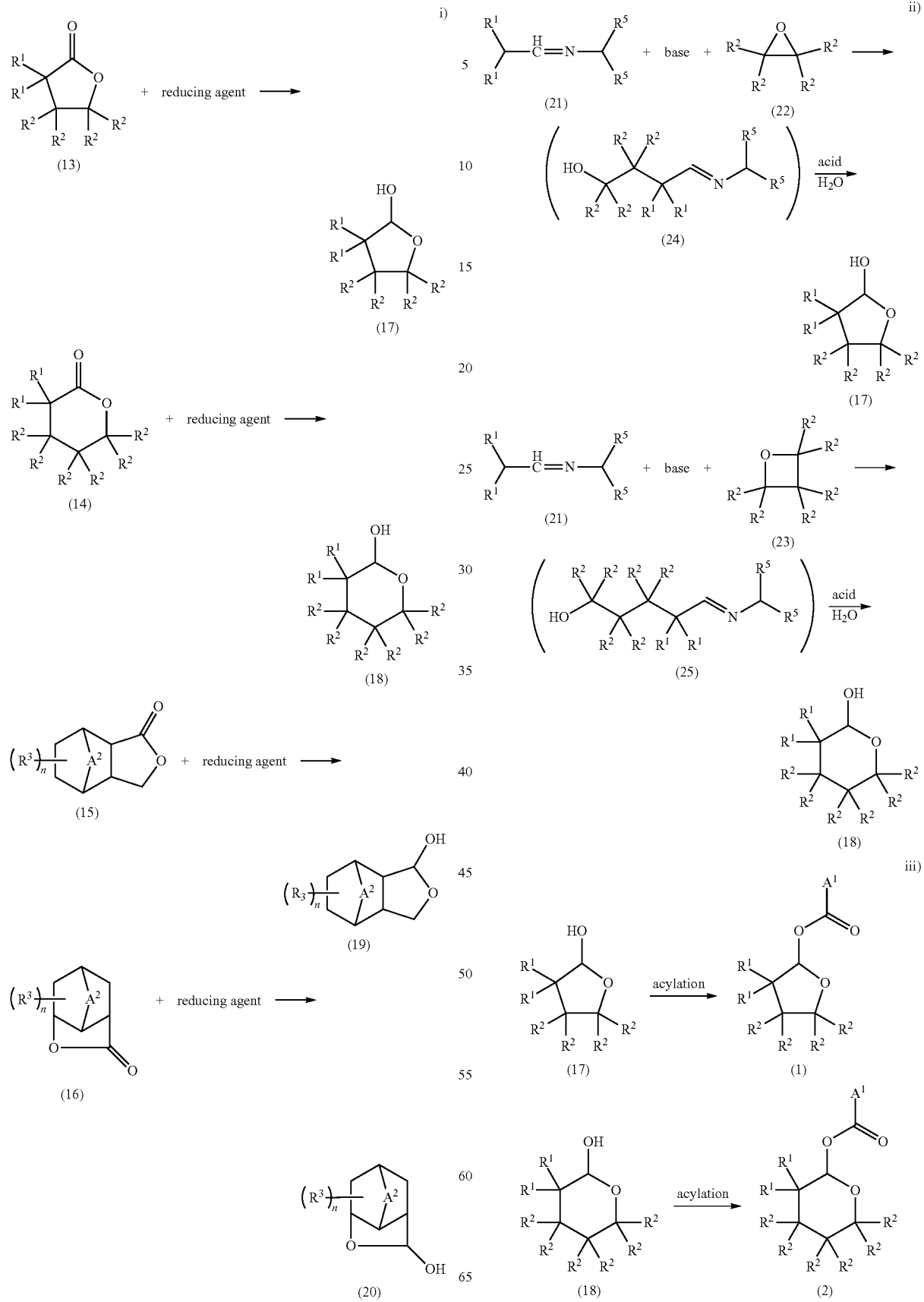

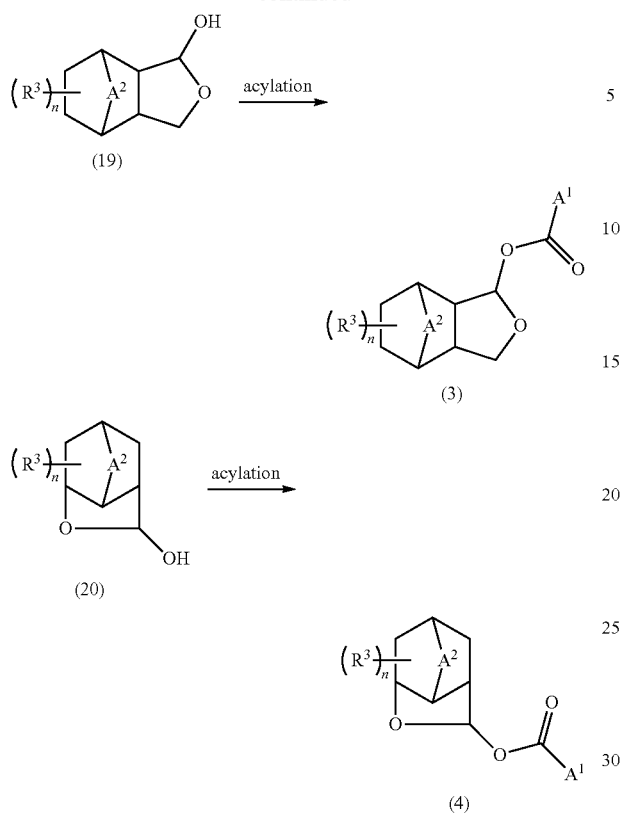
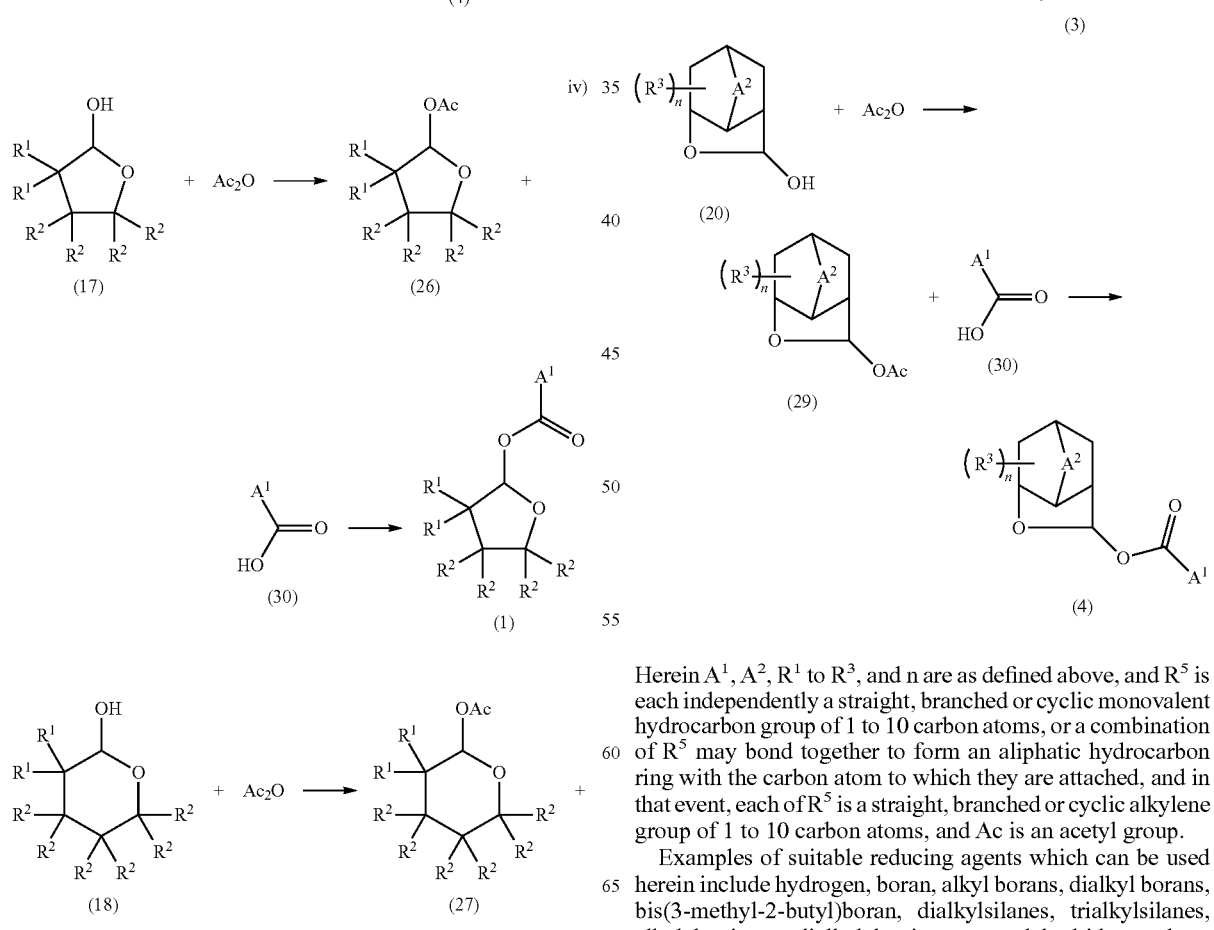

Herein $A^1$, $A^2$, $R^1$ to $R^3$, and n are as defined above, and $R^5$ is each independently a straight, branched or cyclic monovalent hydrocarbon group of 1 to 10 carbon atoms, or a combination of $R^5$ may bond together to form an aliphatic hydrocarbon ring with the carbon atom to which they are attached, and in that event, each of $R^5$ is a straight, branched or cyclic alkylene group of 1 to 10 carbon atoms, and Ac is an acetyl group.

Examples of suitable reducing agents which can be used herein include hydrogen, boran, alkyl borans, dialkyl borans, bis(3-methyl-2-butyl)boran, dialkylsilanes, trialkylsilanes, alkylaluminum, dialkylaluminum; metal hydrides such as sodium hydride, lithium hydride, potassium hydride and calcium hydride; and complex hydrides such as sodium borohydride, lithium borohydride, potassium borohydride, calcium borohydride, sodium aluminum hydride, lithium aluminum hydride, sodium trimethoxyborohydride, lithium trimethoxyaluminohydride, lithium diethoxyaluminohydride, lithium tri-tert-butoxyaluminohydride, sodium bis(2-methoxyethoxy)aluminohydride, lithium triethylborohydride, and diisobutylaluminum hydride, and alkoxy- or alkyl derivatives thereof. In the relevant reaction, use of diisobutylaluminum hydride or bis(3-methyl-2-butyl)boran is especially preferred.

Examples of suitable acids which can be used herein include mineral acids such as hydrochloric acid, hydrobromic acid, sulfuric acid, and nitric acid, and organic acids such as acetic acid, trifluoroacetic acid, oxalic acid, methanesulfonic acid, benzenesulfonic acid, and p-toluenesulfonic acid. The acids may be used alone or in admixture. In the relevant reaction, use of acetic acid is especially preferred.

Examples of suitable bases which can be used herein include alkoxides such as sodium methoxide, sodium ethoxide, lithium methoxide, lithium ethoxide, lithium tert-butoxide, and potassium tert-butoxide; organic amines such as pyridine, triethylamine, N,N-dimethylaniline, and 4-dimethylaminopyridine; inorganic hydroxides such as sodium hydroxide, lithium hydroxide, potassium hydroxide, barium hydroxide, and tetra-n-butylammonium hydroxide; inorganic carbonates such as sodium carbonate, sodium hydrogen carbonate, lithium carbonate, and potassium carbonate; alkyl metal compounds such as trityllithium, tritylsodium, tritylpotassium, methyl lithium, phenyllithium, n-butyllithium, sec-butyllithium, tert-butyllithium, and ethylmagnesium bromide; and metal amides such as sodium amide, potassium amide, lithium diisopropylamide, potassium diisopropylamide, lithium dicyclohexylamide, potassium dicyclohexylamide, lithium 2,2,6,6-tetramethylpiperidine, lithium bistrimethylsilylamide, sodium bistrimethylsilylamide, potassium bistrimethylsilylamide, lithium isopropylcyclohexylamide, and magnesium bromide diisopropylamide. In the relevant reaction, use of ethylmagnesium bromide or lithium diisopropylamide is especially preferred.

With regard to the first step included in the preparation method of ester compounds, procedure i) for the synthesis of intermediate hemiacetal compounds having formulae (17) to (20) and procedure ii) for the synthesis of intermediate hemiacetal compounds having formulae (17) and (18) are described below.

i) One procedure is to synthesize an intermediate hemiacetal compound (17) by reducing a lactone compound (13).

The amount of the reducing agent used varies with the identity of reducing agent used and reaction conditions and is generally 0.5 to 2.0 moles, especially 0.9 to 1.2 moles, per mole of lactone compound (13). Suitable solvents include hydrocarbons such as hexane, heptane, benzene, toluene, xylene, and cumene; and ethers such as dibutyl ether, diethylene glycol diethyl ether, diethylene glycol dimethyl ether, tetrahydrofuran, and 1,4-dioxane, which may be used alone or in admixture. The reaction temperature and time vary widely with other conditions. When diisobutylaluminum hydride is used as the reducing agent, for example, the reaction temperature is in a range from −79° C. to 25° C., and preferably from −70° C. to 0° C. The reaction time is determined as appropriate by monitoring the reaction process by gas chromatography (GC) or silica gel thin-layer chromatography (TLC) because it is desirable from the yield aspect to drive the reaction to completion. Usually the reaction time is about 0.5 to about 10 hours. Thereafter, water is added to the reaction mixture to quench the reaction. The organic layer is separated, dried, and concentrated, yielding intermediate hemiacetal compound (17). If necessary, the compound may be purified by standard techniques like distillation and chromatography. Likewise, intermediate hemiacetal compounds (18), (19) and (20) can be synthesized from lactone compounds (14), (15) and (16), respectively.

ii) In an alternative procedure, an imine compound (21) is converted into an N-metal enamine compound by withdrawing α-hydrogen therefrom with the aid of a base. The N-metal enamine compound is reacted with an oxirane compound (22) to form a hydroxyl-containing imine compound (24). Then the imine compound (24) is treated with an acid so that conversion from imine to aldehyde and cyclization reaction occur in sequence whereby the intermediate hemiacetal compound (17) is synthesized.

The amount of the base used varies with reaction conditions. When ethylmagnesium bromide is used as the base, for example, an appropriate amount is 0.8 to 3.0 moles, and especially 1.1 to 1.5 moles, per mole of imine compound (21). Suitable solvents include hydrocarbons such as hexane, heptane, benzene, toluene, xylene, and cumene; and ethers such as dibutyl ether, diethylene glycol diethyl ether, diethylene glycol dimethyl ether, tetrahydrofuran, and 1,4-dioxane, which may be used alone or in admixture. The reaction temperature is in a range from −20° C. to 80° C., and preferably from 0° C. to 50° C. The reaction time is preferably about 5 minutes to about 30 hours, more preferably about 10 minutes to about 5 hours. After the reaction with the base, oxirane compound (22) is added, desirably in an amount of 0.8 to 5.0 moles, more desirably 1.1 to 3.0 moles per mole of imine compound (21). The reaction temperature is in a range from −20° C. to 60° C., and preferably from 0° C. to 30° C. The reaction time is determined as appropriate by monitoring the reaction process by GC or silica gel TLC because it is desirable from the yield aspect to drive the reaction to completion. Usually the reaction time is about 0.5 to about 10 hours. From the reaction mixture, hydroxyl-containing imine compound (24) may be collected by ordinary aqueous workup. Thereafter, an acid is added to hydroxyl-containing imine compound (24). From the reaction mixture, hemiacetal compound (17) is collected by ordinary aqueous workup. The amount of the acid used is 0.5 to 3.0 moles, and preferably 0.8 to 1.5 moles, per mole of imine compound (21). The reaction time is determined as appropriate by monitoring the reaction process by GC or silica gel TLC because it is desirable from the yield aspect to drive the reaction to completion. Usually the reaction time is about 1 to about 30 hours. If necessary, the intermediate hemiacetal compound may be purified by standard techniques like distillation and chromatography. Likewise, intermediate hemiacetal compound (18) can be synthesized using oxetane compound (23) instead of oxirane compound (22).

With regard to the second step included in the preparation method of ester compounds, procedures iii) and iv) for the synthesis of ester compounds (1) to (4) are described below.

iii) The second step is the acylation of intermediate hemiacetal compound (17). For the acylation reaction, well-known ester forming methods including reaction with an acylating agent, reaction with a carboxylic acid, and transesterification reaction may be applicable.

In the case of reaction with an acylating agent, preferably the alcohol compound, an acylating agent, and a base are sequentially or simultaneously added to a solvent for reaction. The solvent used herein is selected from among chlorinated solvents such as methylene chloride, chloroform, and trichloroethylene; hydrocarbons such as hexane, heptane, benzene, toluene, xylene and cumene; ethers such as dibutyl ether, diethylene glycol diethyl ether, diethylene glycol dimethyl ether, tetrahydrofuran, and 1,4-dioxane; nitriles such as acetonitrile; ketones such as acetone and 2-butanone; esters such as ethyl acetate and n-butyl acetate; and aprotic polar solvents such as N,N-dimethylformamide, dimethyl sulfoxide and hexamethylphosphoric triamide, and mixtures thereof. The acylating agent is selected from among acid halides such as acrylic acid chloride, methacrylic acid chloride, acrylic acid bromide, methacrylic acid bromide, and α-trifluoromethylacrylic acid chloride; and acid anhydrides such as acrylic anhydride, methacrylic anhydride, α-trifluoromethylacrylic anhydride, acrylic/trifluoroacetic mixed acid anhydride, methacrylic/trifluoroacetic mixed acid anhydride, α-trifluoromethylacrylic/trifluoroacetic mixed acid anhydride, acrylic/p-nitrobenzoic mixed acid anhydride, methacrylic/p-nitrobenzoic mixed acid anhydride, ethyl acrylate/carbonic mixed acid anhydride, and ethyl methacrylate/carbonic mixed acid anhydride. The base is selected from among triethylamine, diisopropylethylamine, N,N-dimethylaniline, pyridine, and 4-dimethylaminopyridine. The reaction temperature may be selected as appropriate in accordance with the identity of acylating agent and other reaction conditions and is preferably in the range from −50° C. to approximately the boiling point of the solvent, and more preferably in the range from −20° C. to approximately room temperature. The amount of acylating agent used depends on the structure of alcohol compound used and is generally 1 to 40 moles, and preferably 1 to 5 moles per mole of the alcohol compound.

The reaction with a carboxylic acid is a dehydration reaction between the alcohol compound and a corresponding carboxylic acid such as acrylic acid, methacrylic acid or α-trifluoromethylacrylic acid, typically in the presence of an acid catalyst. The amount of the carboxylic acid used depends on the structure and is usually 1 to 40 moles, preferably 1 to 5 moles per mole of the alcohol compound. Examples of the acid catalyst include mineral acids such as hydrochloric acid, hydrobromic acid, sulfuric acid and nitric acid, and organic acids such as oxalic acid, trifluoroacetic acid, methanesulfonic acid, benzenesulfonic acid and p-toluenesulfonic acid, and mixtures thereof. The amount of the acid catalyst used is a catalytic amount in the range of 0.001 to 1 mole, preferably 0.01 to 0.05 mole per mole of the alcohol compound. The solvent used herein is as exemplified above for the reaction with acylating agent. The reaction temperature is preferably in a range from −50° C. to approximately the boiling point of the solvent. It is also preferable to carry out the reaction in a solvent comprising a hydrocarbon such as hexane, heptane, benzene, toluene, xylene or cumene, while azeotroping off the water of reaction. In this case, the water may be distilled off by refluxing under atmospheric pressure at the boiling point of the solvent, or under reduced pressure at a temperature below the boiling point.

In the case of transesterification reaction, the alcohol compound is reacted with a corresponding carboxylic acid ester, such as acrylate, methacrylate or α-trifluoromethylacrylate in the presence of a catalyst, and the resulting alcohol is removed. The carboxylic acid ester used herein is preferably selected from primary alkyl esters, with methyl, ethyl and n-propyl esters being preferred from the standpoints of cost and ease of reaction. The amount of carboxylic acid ester used depends on the structure and is in a range of 1 to 40 moles, and preferably 1 to 5 moles per mole of the alcohol compound. Examples of the catalyst used include mineral acids such as hydrochloric acid, hydrobromic acid, sulfuric acid and nitric acid; organic acids such as oxalic acid, trifluoroacetic acid, methanesulfonic acid, benzenesulfonic acid and p-toluenesulfonic acid; bases such as sodium methoxide, sodium ethoxide, potassium t-butoxide, and 4-dimethylaminopyridine; salts such as sodium cyanate, potassium cyanate, sodium acetate, potassium acetate, calcium acetate, tin acetate, aluminum acetate, aluminum acetoacetate, and alumina; Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, titanium (IV) ethoxide, titanium(IV) isopropoxide, and titanium oxide, which may be used alone or in admixture. The amount of catalyst used is in a range of 0.001 to 20 moles, and preferably 0.01 to 0.05 mole per mole of the alcohol compound. The reaction may be performed in a solventless system (the reactant carboxylic acid ester itself may be used as a solvent), which is preferable because of no need for extra operations like concentration and solvent recovery. A solvent may be used in an auxiliary manner for the purpose of preventing the end product and reactants from polymerization. Examples of the solvent, if used, include hydrocarbons such as hexane, heptane, benzene, toluene, xylene, and cumene; and ethers such as dibutyl ether, diethylene glycol diethyl ether, diethylene glycol dimethyl ether, tetrahydrofuran, and 1,4-dioxane, which may be used alone or in admixture. The reaction temperature may be selected as appropriate depending on the identity of carboxylic acid ester and other reaction conditions. Most often, the reaction is carried out while heating, typically at a temperature near the boiling point of the low-boiling alcohol formed by transesterification such as methanol, ethanol or 1-propanol. Better results are obtained by carrying out the reaction while distilling off the alcohol formed. The alcohol may be distilled off under reduced pressure and at a temperature lower than its boiling point.

If necessary, the resulting ester compound (1) may be purified by standard techniques such as chromatography, distillation and recrystallization. Using the known ester preparation methods described above, ester compounds (2), (3) and (4) can be synthesized from intermediate hemiacetal compounds (18), (19) and (20), respectively.

iv) In an alternative procedure of the second step, ester compound (1) can be synthesized by once acetylating the intermediate hemiacetal compound and then effecting acetal exchange reaction with a carboxylic acid. Acetylation of intermediate hemiacetal compound (17) may be performed by a standard technique using pyridine and acetic anhydride. If necessary, the resulting acetate (26) may be purified by standard techniques such as chromatography, distillation and recrystallization.

Subsequently, carboxylic acid (30), for example, acrylic acid, methacrylic acid or α-trifluoromethylacrylic acid is added to acetate (26) and optionally, an acid catalyst added. The amount of carboxylic acid used is desirably 1.0 to 20.0 moles, and more desirably 2.0 to 10.0 moles per mole of acetate (26). Examples of suitable acid catalysts which can be used herein include mineral acids such as hydrochloric acid, hydrobromic acid, sulfuric acid, and nitric acid, organic acids such as oxalic acid, trifluoroacetic acid, methanesulfonic acid, benzenesulfonic acid, and p-toluenesulfonic acid, organic salts such as pyridinium p-toluenesulfonate, and acidic ion-exchange resins. The amount of acid catalyst used is desirably 0 to 0.20 mole, and more desirably 0 to 0.10 moles per mole of acetate (26). Although the reaction generates an equilibrium mixture of acetate (26) and ester compound (1), the equilibrium can be biased toward the end product, ester compound (1) by distilling off the acetic acid formed under reduced pressure. From the reaction mixture, ester compound (1) may be collected by ordinary aqueous workup. If necessary, ester compound (1) may be purified by standard techniques such as chromatography, distillation and recrystallization. In some cases, the reaction mixture may be directly purified without the aqueous workup. Likewise, ester compounds (2), (3) and (4) can be synthesized from intermediate hemiacetal compounds (18), (19) and (20), respectively.

Polymer

The polymers of the invention are characterized by comprising recurring units derived from ester compounds having formulae (1) to (4).

The recurring units derived from ester compounds having formulae (1) to (4) include those having the following formulae (1a) to (4c). It is noted that units of formulae (1c), (2c), (3c), and (4c) are obtained by carrying out ring-opening metathesis polymerization (ROMP) and hydrogenation on a double bond.

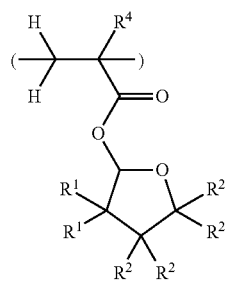
(1a)

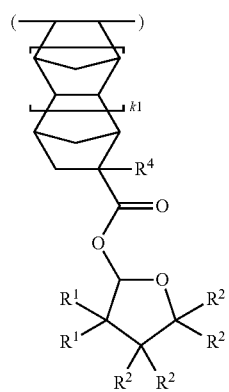
(1b)

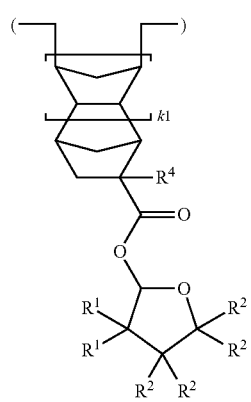
(1c)

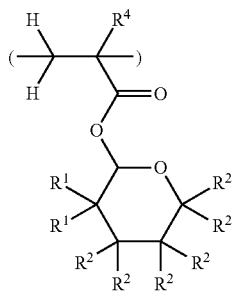
(2a)

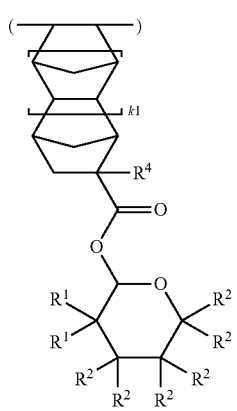
(2b)

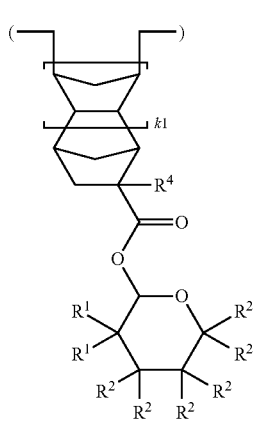
(2c)

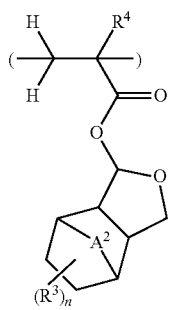
(3a)

(3b)
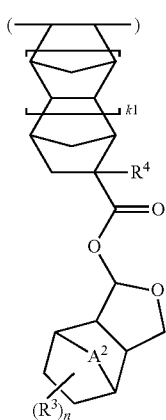

(3c)
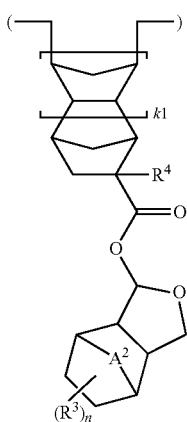

(4a)
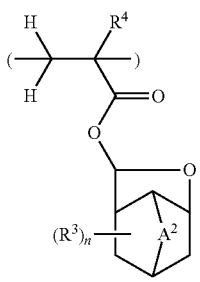

(4b)
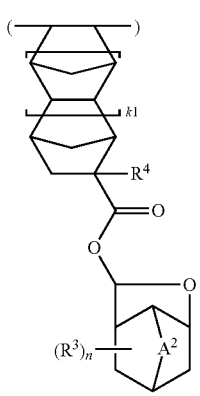

(4c)
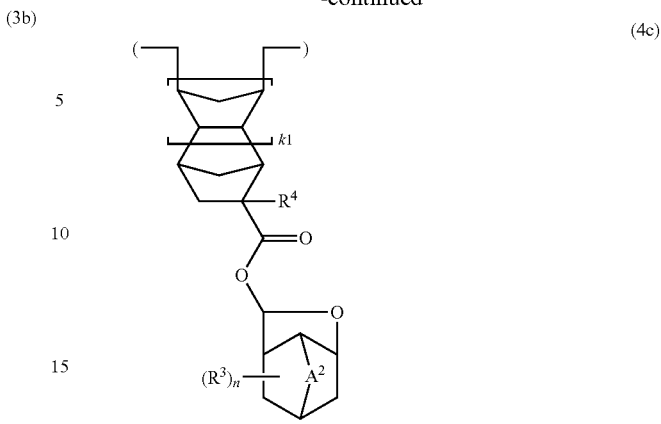

Herein, $A^2$, $R^1$ to $R^4$, and n are as defined above, and $k^1$ is 0 or 1.

In addition to the recurring units of formulae (1a) to (4c), the polymer may further comprise recurring units derived from another monomer having a polymerizable double bond.

The recurring units derived from the monomer having a polymerizable double bond include, but are not limited to, those having the following general formula (R1).

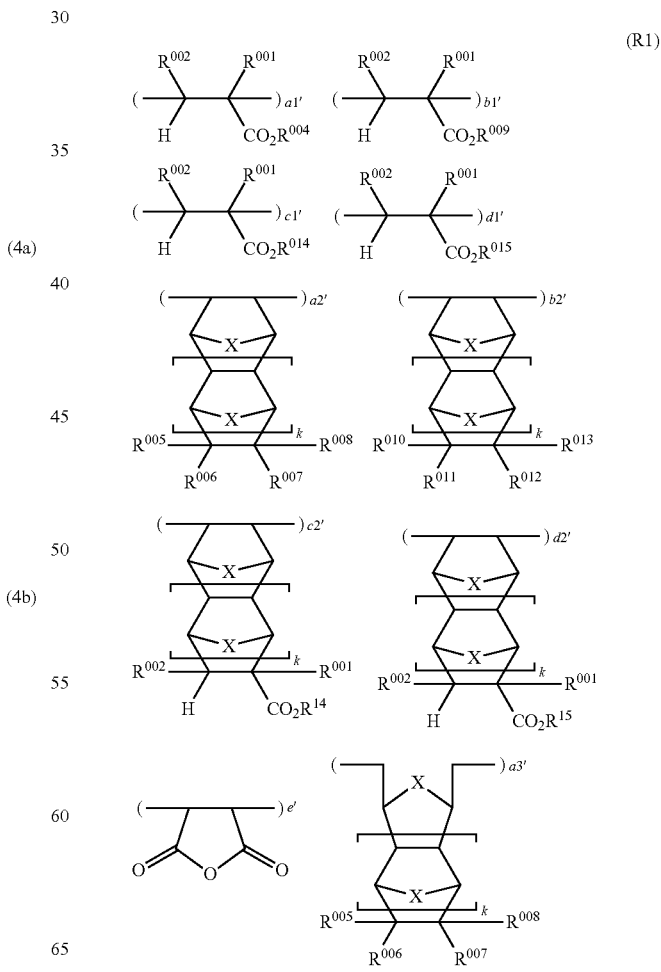
(R1)

-continued

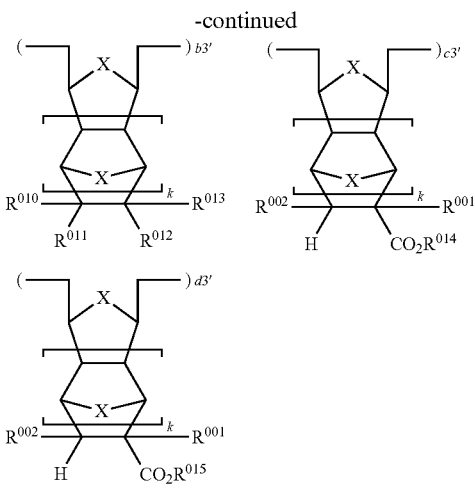

Herein $R^{001}$ is a hydrogen atom, fluorine atom, methyl group, trifluoromethyl group or $CH_2CO_2R^{003}$.

$R^{002}$ is a hydrogen atom, methyl group or $CO_2R^{003}$.

$R^{003}$ is a straight, branched or cyclic $C_1$-$C_{15}$ alkyl group, examples of which include methyl, ethyl, propyl, isopropyl, n-butyl, sec-butyl, tert-butyl, tert-amyl, n-pentyl, n-hexyl, cyclopentyl, cyclohexyl, ethylcyclopentyl, butylcyclopentyl, ethylcyclohexyl, butylcyclohexyl, adamantyl, ethyladamantyl, and butyladamantyl.

$R^{004}$ is a hydrogen atom or a monovalent hydrocarbon group of 1 to 15 carbon atoms having at least one group selected from among fluorinated substituent groups, carboxyl, hydroxyl and cyano groups. Examples include hydrogen, carboxyethyl, carboxybutyl, carboxycyclopentyl, carboxycyclohexyl, carboxynorbornyl, carboxyadamantyl, hydroxyethyl, hydroxybutyl, hydroxycyclopentyl, hydroxycyclohexyl, hydroxynorbornyl, hydroxyadamantyl, [2,2,2-trifluoro-1-hydroxy-1-(trifluoromethyl)ethyl]-cyclohexyl, and bis[2,2,2-trifluoro-1-hydroxy-1-(trifluoromethyl)ethyl]-cyclohexyl.

At least one of $R^{005}$ to $R^{008}$ is a carboxyl group or a monovalent hydrocarbon group of 1 to 15 carbon atoms having at least one group selected from among fluorinated substituent groups, carboxyl, hydroxyl and cyano groups while the remaining of $R^{005}$ to $R^{008}$ are each independently hydrogen or straight, branched or cyclic $C_1$-$C_{15}$ alkyl groups. Examples of suitable monovalent $C_1$-$C_{15}$ hydrocarbon groups having at least one group selected from among fluorinated substituent groups, carboxyl groups, hydroxyl groups and cyano groups include carboxymethyl, carboxyethyl, carboxybutyl, hydroxymethyl, hydroxyethyl, hydroxybutyl, 2-carboxyethoxycarbonyl, 4-carboxybutoxycarbonyl, 2-hydroxyethoxycarbonyl, 4-hydroxybutoxycarbonyl, carboxycyclopentyloxycarbonyl, carboxycyclohexyloxycarbonyl, carboxynorbornyloxycarbonyl, carboxyadamantyloxycarbonyl, hydroxycyclopentyloxycarbonyl, hydroxycyclohexyloxycarbonyl, hydroxynorbornyloxycarbonyl, hydroxyadamantyloxycarbonyl, [2,2,2-trifluoro-1-hydroxy-1-(trifluoromethyl)ethyl]-cyclohexyloxycarbonyl, and bis[2,2,2-trifluoro-1-hydroxy-1-(trifluoromethyl)ethyl]-cyclohexyloxycarbonyl. Suitable straight, branched or cyclic $C_1$-$C_{15}$ alkyl groups are as exemplified for $R^{003}$.

Two of $R^{005}$ to $R^{008}$ (for example, a pair of $R^{005}$ and $R^{006}$, $R^{006}$ and $R^{007}$, or $R^{007}$ and $R^{008}$) may bond together to form an aliphatic hydrocarbon ring with the carbon atom(s) to which they are attached, and in that event, at least one of $R^{005}$ to $R^{008}$ is a divalent hydrocarbon group of 1 to 15 carbon atoms having at least one group selected from fluorinated substituent groups, carboxyl, hydroxyl and cyano groups while the remaining of $R^{005}$ to $R^{008}$ are each independently single bonds, hydrogen atoms or straight, branched or cyclic $C_1$-$C_{15}$ alkyl groups. Suitable divalent $C_1$-$C_{15}$ hydrocarbon groups having at least one group selected from fluorinated substituent groups, carboxyl, hydroxyl and cyano groups include those exemplified above as the monovalent hydrocarbon groups having at least one group selected from fluorinated substituent groups, carboxyl, hydroxyl and cyano groups, with one hydrogen atom eliminated therefrom.

$R^{009}$ is a monovalent hydrocarbon group of 3 to 15 carbon atoms containing a —$CO_2$— partial structure. Examples include 2-oxooxolan-3-yl, 4,4-dimethyl-2-oxooxolan-3-yl, 4-methyl-2-oxooxan-4-yl, 2-oxo-1,3-dioxolan-4-ylmethyl, and 5-methyl-2-oxooxolan-5-yl.

At least one of $R^{010}$ to $R^{013}$ is a monovalent hydrocarbon group of 2 to 15 carbon atoms containing a —$CO_2$— partial structure while the remaining of $R^{010}$ to $R^{013}$ are each independently hydrogen atoms or straight, branched or cyclic $C_1$-$C_{15}$ alkyl groups. Illustrative examples of suitable monovalent $C_2$-$C_{15}$ hydrocarbon groups containing a —$CO_2$— partial structure include 2-oxooxolan-3-yloxycarbonyl, 4,4-dimethyl-2-oxooxolan-3-yloxycarbonyl, 4-methyl-2-oxooxan-4-yloxycarbonyl, 2-oxo-1,3-dioxolan-4-ylmethyloxycarbonyl, and 5-methyl-2-oxooxolan-5-yloxycarbonyl. Suitable straight, branched or cyclic $C_1$-$C_{15}$ alkyl groups are as exemplified for $R^{003}$.

Two of $R^{010}$ to $R^{013}$ (for example, a pair of $R^{010}$ and $R^{011}$, $R^{011}$ and $R^{012}$, or $R^{012}$ and $R^{013}$) may bond together to form an aliphatic hydrocarbon ring with the carbon atom(s) to which they are attached, and in that event, at least one of $R^{010}$ to $R^{013}$ is a divalent hydrocarbon group of 1 to 15 carbon atoms having a —$CO_2$— partial structure while the remaining of $R^{010}$ to $R^{013}$ are each independently single bonds, hydrogen atoms or straight, branched or cyclic $C_1$-$C_{15}$ alkyl groups. Illustrative examples of suitable divalent $C_1$-$C_{15}$ hydrocarbon groups containing a —$CO_2$— partial structure include 1-oxo-2-oxapropane-1,3-diyl, 1,3-dioxo-2-oxapropane-1,3-diyl, 1-oxo-2-oxabutane-1,4-diyl, and 1,3-dioxo-2-oxabutane-1,4-diyl, as well as those exemplified as the monovalent hydrocarbon groups containing a —$CO_2$— partial structure, with one hydrogen atom eliminated therefrom.

$R^{014}$ is a polycyclic hydrocarbon group having 7 to 15 carbon atoms or an alkyl group containing such a polycyclic hydrocarbon group. Examples include norbornyl, bicyclo[3.3.1]nonyl, tricyclo[5.2.1.0$^{2,6}$]decyl, adamantyl, norbornylmethyl, adamantylmethyl, and alkyl- or cycloalkyl-substituted derivatives thereof.

$R^{015}$ is an acid labile group, which will be described later in detail.

X is $CH_2$ or an oxygen atom, and k is 0 or 1.

The acid labile group represented by $R^{015}$ may be selected from a variety of such groups. It is a group to be deprotected by the acid generated from the photoacid generator to be described later and may be any of well-known acid labile groups which are commonly used in prior art resist materials, especially chemically amplified resist materials. Examples of the acid labile group are groups of the following general formulae (L1) to (L4), tertiary alkyl groups of 4 to 20 carbon atoms, preferably 4 to 15 carbon atoms, trialkylsilyl groups in which each alkyl moiety has 1 to 6 carbon atoms, and oxoalkyl groups of 4 to 20 carbon atoms.

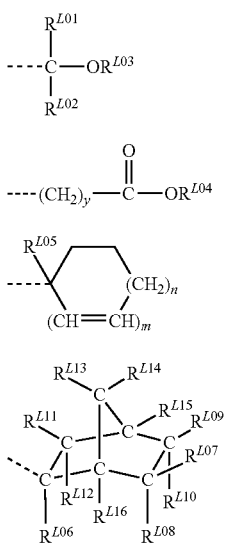

(L1)

(L2)

(L3)

(L4)

Herein the broken line denotes a valence bond. $R^{L01}$ and $R^{L02}$ are hydrogen or straight, branched or cyclic alkyl groups of 1 to 18 carbon atoms, preferably 1 to 10 carbon atoms. Exemplary alkyl groups include methyl, ethyl, propyl, isopropyl, n-butyl, sec-butyl, tert-butyl, cyclopentyl, cyclohexyl, 2-ethylhexyl, n-octyl, and adamantyl. $R^{L03}$ is a monovalent hydrocarbon group of 1 to 18 carbon atoms, preferably 1 to 10 carbon atoms, which may contain a hetero atom such as oxygen, examples of which include unsubstituted straight, branched or cyclic alkyl groups and substituted forms of such alkyl groups in which some hydrogen atoms are replaced by hydroxyl, alkoxy, oxo, amino, alkylamino or the like. Illustrative examples of the straight, branched or cyclic alkyl groups are as exemplified above for $R^{L01}$ and $R^{L02}$, and examples of the substituted alkyl groups are as shown below.

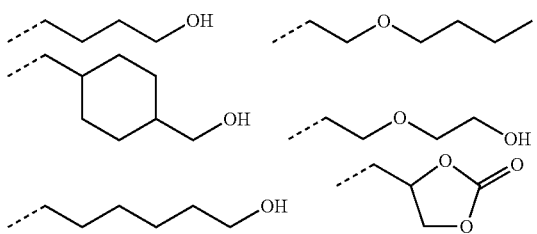

A pair of $R^{L01}$ and $R^{L02}$, $R^{L01}$ and $R^{L03}$, or $R^{L02}$ and $R^{L03}$ may together form an aliphatic ring with carbon and oxygen atoms to which they are attached. The cyclization group of $R^{L01}$, $R^{L02}$ and $R^{L03}$ is a straight or branched alkylene group of 1 to 18 carbon atoms, preferably 1 to 10 carbon atoms when they form a ring.

$R^{L04}$ is a tertiary alkyl group of 4 to 20 carbon atoms, preferably 4 to 15 carbon atoms, a trialkylsilyl group in which each alkyl moiety has 1 to 6 carbon atoms, an oxoalkyl group of 4 to 20 carbon atoms, or a group of formula (L1). Exemplary tertiary alkyl groups are tert-butyl, tert-amyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 2-(tricyclo[5.2.1.0$^{2,6}$]decan-8-yl)propan-2-yl, 2-(tetracyclo[4.4.0.1$^{2,5}$.1$^{7,10}$]dodecan-3-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, 2-ethyl-2-adamantyl, 8-methyl-8-tricyclo[5.2.1.0$^{2,6}$]decyl, 8-ethyl-8-tricyclo[5.2.1.0$^{2,6}$]decyl, 3-methyl-3-tetracyclo[4.4.0.1$^{2,5}$.1$^{7,10}$]dodecyl, 3-ethyl-3-tetracyclo[4.4.0.1$^{2,5}$.1$^{7,10}$]dodecyl, and the like. Exemplary trialkylsilyl groups are trimethylsilyl, triethylsilyl, and dimethyl-tert-butylsilyl. Exemplary oxoalkyl groups are 3-oxocyclohexyl, 4-methyl-2-oxooxan-4-yl, and 5-methyl-2-oxooxolan-5-yl. Letter y is an integer of 0 to 6.

In formula (L3), $R^{L05}$ is an optionally substituted, straight, branched or cyclic $C_1$-$C_{10}$ alkyl group or an optionally substituted $C_6$-$C_{20}$ aryl group. Examples of the optionally substituted alkyl groups include straight, branched or cyclic alkyl groups such as methyl, ethyl, propyl, isopropyl, n-butyl, sec-butyl, tert-butyl, tert-amyl, n-pentyl, n-hexyl, cyclopentyl, cyclohexyl, and bicyclo[2.2.1]heptyl, and substituted forms of such groups in which some hydrogen atoms are replaced by hydroxyl, alkoxy, carboxy, alkoxycarbonyl, oxo, amino, alkylamino, cyano, mercapto, alkylthio, sulfo or other groups or in which some methylene groups are replaced by oxygen or sulfur atoms. Examples of optionally substituted aryl groups include phenyl, methylphenyl, naphthyl, anthryl, phenanthryl, and pyrenyl. Letter m is equal to 0 or 1, n is equal to 0, 1, 2 or 3, and 2m+n is equal to 2 or 3.

In formula (L4), $R^{L06}$ is an optionally substituted, straight, branched or cyclic $C_1$-$C_{10}$ alkyl group or an optionally substituted $C_6$-$C_{20}$ aryl group. Examples of these groups are the same as exemplified for $R^{L05}$. $R^{L07}$ to $R^{L16}$ independently represent hydrogen or monovalent hydrocarbon groups of 1 to 15 carbon atoms. Exemplary hydrocarbon groups are straight, branched or cyclic alkyl groups such as methyl, ethyl, propyl, isopropyl, n-butyl, sec-butyl, tert-butyl, tert-amyl, n-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of these groups in which some hydrogen atoms are replaced by hydroxyl, alkoxy, carboxy, alkoxycarbonyl, oxo, amino, alkylamino, cyano, mercapto, alkylthio, sulfo or other groups. Alternatively, $R^{L07}$ to $R^{L16}$ may bond together to form a ring (for example, a pair of $R^{L07}$ and $R^{L08}$, $R^{L07}$ and $R^{L09}$, and $R^{L08}$ and $R^{L10}$, $R^{L09}$ and $R^{L10}$, $R^{L11}$ and $R^{L12}$, $R^{L13}$ and $R^{L14}$, or a similar pair form a ring). Each of $R^{L07}$ to $R^{L16}$ represents a divalent $C_1$-$C_{15}$ hydrocarbon group when they form a ring, examples of which are those exemplified above for the monovalent hydrocarbon groups, with one hydrogen atom being eliminated. Two of $R^{L07}$ to $R^{L16}$ which are attached to vicinal carbon atoms may bond together directly to form a double bond (for example, a pair of $R^{L07}$ and $R^{L09}$, $R^{L09}$ and $R^{L15}$, $R^{L13}$ and $R^{L15}$, or a similar pair).

Of the acid labile groups of formula (L1), the straight and branched ones are exemplified by the following groups.

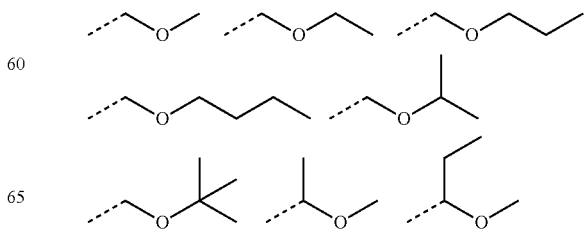

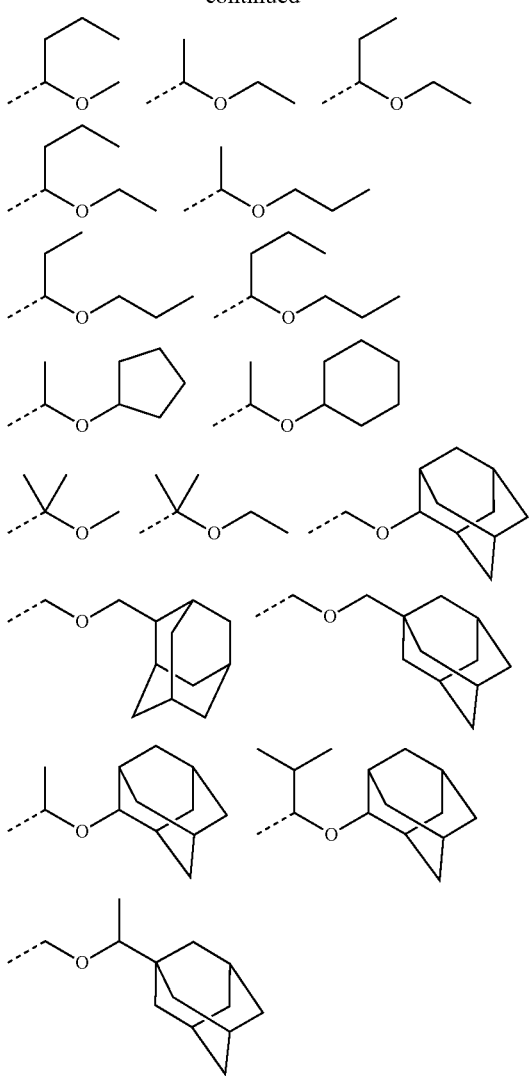

Of the acid labile groups of formula (L1), the cyclic ones are, for example, tetrahydrofuran-2-yl, 2-methyltetrahydrofuran-2-yl, tetrahydropyran-2-yl, and 2-methyltetrahydropyran-2-yl.

Examples of the acid labile groups of formula (L2) include tert-butoxycarbonyl, tert-butoxycarbonylmethyl, tert-amyloxycarbonyl, tert-amyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl groups.

Examples of the acid labile groups of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-cyclohexylcyclopentyl, 1-(4-methoxybutyl)cyclopentyl, 1-(bicyclo[2.2.1]heptan-2-yl)cyclopentyl, 1-(7-oxabicyclo[2.2.1]heptan-2-yl)cyclopentyl, 1-methylcyclohexyl, 1-ethylcyclohexyl, 1-methyl-2-cyclopentenyl, 1-ethyl-2-cyclopentenyl, 1-methyl-2-cyclohexenyl, and 1-ethyl-2-cyclohexenyl groups.

Of the acid labile groups of formula (L4), those groups of the following formulae (L4-1) to (L4-4) are preferred.

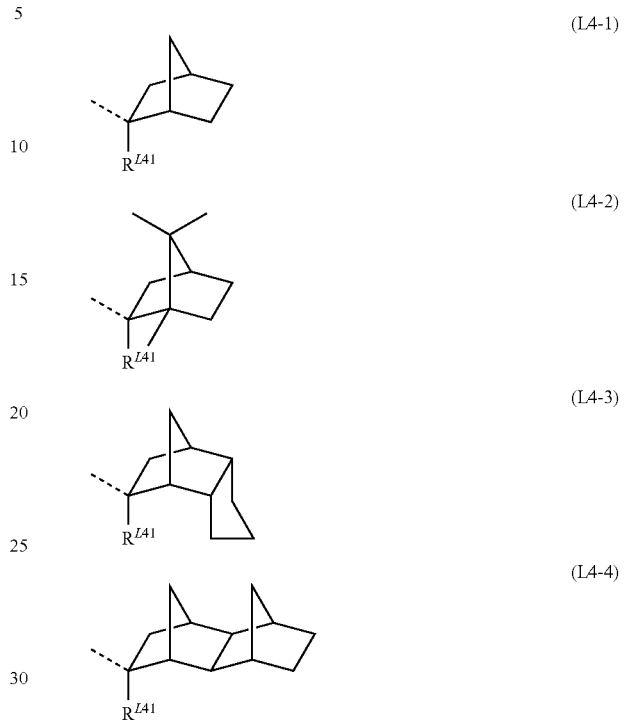

In formulas (L4-1) to (L4-4), the broken line denotes a bonding site and direction. $R^{L41}$ is each independently a monovalent hydrocarbon group, typically a straight, branched or cyclic $C_1$-$C_{10}$ alkyl group, such as methyl, ethyl, propyl, isopropyl, n-butyl, sec-butyl, tert-butyl, tert-amyl, n-pentyl, n-hexyl, cyclopentyl and cyclohexyl.

For formulas (L4-1) to (L4-4), there can exist enantiomers and diastereomers. Each of formulae (L4-1) to (L4-4) collectively represents all such stereoisomers. Such stereoisomers may be used alone or in admixture.

For example, the general formula (L4-3) represents one or a mixture of two or more selected from groups having the following general formulas (L4-3-1) and (L4-3-2).

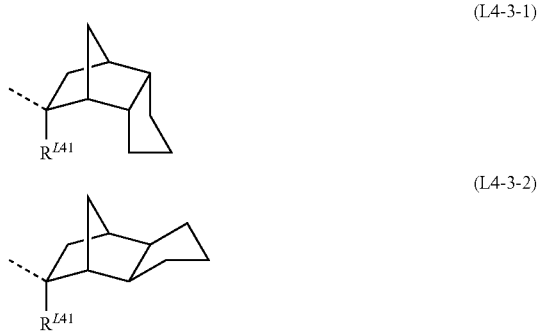

Similarly, the general formula (L4-4) represents one or a mixture of two or more selected from groups having the following general formulas (L4-4-1) to (L4-4-4).

(L4-4-1)
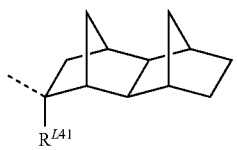

(L4-4-2)
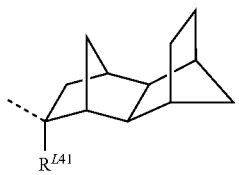

(L4-4-3)
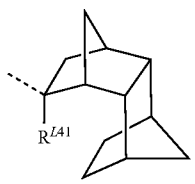

(L4-4-4)
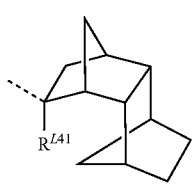

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the bond direction is on the exo side relative to the bicyclo[2.2.1]heptane ring, which ensures high reactivity for acid catalyzed elimination reaction (see JP-A 2000-336121). In preparing these monomers having a tertiary exo-alkyl group of bicyclo[2.2.1]heptane skeleton as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

(L4-1-endo)
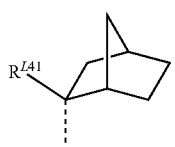

(L4-2-endo)
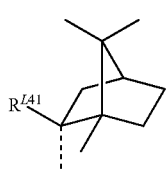

(L4-3-endo)
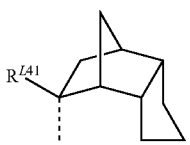

(L4-4-endo)
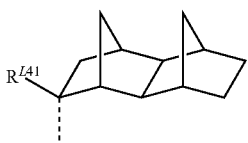

Illustrative examples of the acid labile group of formula (L4) are given below

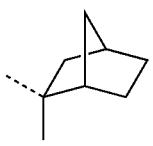 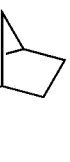 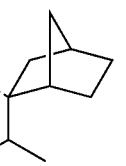

 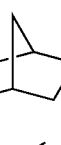 

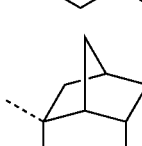 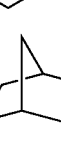 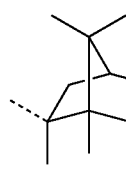

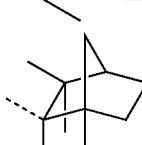 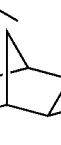 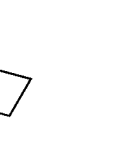

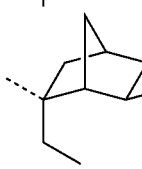 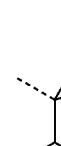 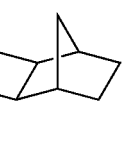

Examples of the tertiary $C_4$-$C_{20}$ alkyl groups, trialkylsilyl groups in which each alkyl moiety has 1 to 6 carbon atoms, and $C_4$-$C_{20}$ oxoalkyl groups are as exemplified for $R^{LO4}$ and the like.

In formula (R1), letters a1', a2', a3', b1', b2', b3', c1', c2', c3', d1', d2', d3', and e' are numbers from 0 to less than 1 and indicate proportions of corresponding recurring units relative to the entire recurring units of a polymer.

The polymer of the invention should preferably have a weight average molecular weight of 1,000 to 500,000, more preferably 3,000 to 100,000, as measured by gel permeation chromatography (GPC) versus polystyrene standards. Outside the range, there may arise problems such as an extreme lowering of etching resistance and a lowering of resolution due to a failure to have a difference in dissolution rate before and after exposure.

In the polymers of the invention, the preferred proportion of recurring units based on the respective monomers is in the following range (in mol %), though not limited thereto. The polymers contain:

(I) from 5 mol % to 100 mol %, preferably 5 mol % to 60 mol % of constituent units having one or more of formulae (1a) to (4c) derived from the monomers of formulae (1) to (4), and (II) from 0 mol % to less than 100 mol %, preferably 1 mol % to 95 mol %, and more preferably 40 mol % to 95 mol % of constituent units of one or more types in formula (R1).

The polymers of the invention can be prepared through copolymerization reaction using one or more compounds of formulae (1) to (4) as a first monomer and compounds having a polymerizable double bond as second and subsequent monomers. While a variety of copolymerization reaction methods may be used in preparing the polymers of the invention, radical polymerization, anionic polymerization and coordination polymerization are preferred.

For radical polymerization, preferred reaction conditions include (a) a solvent selected from among hydrocarbons such as benzene, ethers such as tetrahydrofuran, alcohols such as ethanol, ketones such as methyl isobutyl ketone and methyl ethyl ketone, esters such as propylene glycol monomethyl ether acetate, propylene glycol monoethyl ether acetate, and ethyl lactate, and lactones such as γ-butyrolactone, (b) a polymerization initiator selected from azo compounds such as 2,2'-azobisisobutyronitrile and peroxides such as benzoyl peroxide and lauroyl peroxide, (c) a temperature of about 0° C. to about 100° C., and (d) a time of about 0.5 to about 48 hours. Reaction conditions outside the described range may be employed if desired.

For anionic polymerization, preferred reaction conditions include (a) a solvent selected from among hydrocarbons such as benzene, ethers such as tetrahydrofuran, and liquid ammonia, (b) a polymerization initiator selected from metals such as sodium and potassium, alkyl metals such as n-butyllithium and sec-butyllithium, ketyl, and Grignard reagents, (c) a temperature of about −78° C. to about 0° C., (d) a time of about 0.5 to about 48 hours, and (e) a stopper selected from among proton-donative compounds such as methanol, halides such as methyl iodide, and electrophilic compounds. Reaction conditions outside the described range may be employed if desired.

For coordination polymerization, preferred reaction conditions include (a) a solvent selected from among hydrocarbons such as n-heptane and toluene, (b) a catalyst selected from Ziegler-Natta catalysts comprising a transition metal (e.g., titanium) and alkylaluminum, Phillips catalysts of metal oxides having chromium or nickel compounds carried thereon, and olefin-metathesis mixed catalysts as typified by tungsten and rhenium mixed catalysts, (c) a temperature of about 0° C. to about 100° C., and (d) a time of about 0.5 to about 48 hours. Reaction conditions outside the described range may be employed if desired.

Resist Composition

Since the polymer of the invention is useful as the base resin of a resist composition, the other aspect of the invention provides a resist composition, especially a chemically amplified positive resist composition, comprising the polymer. Typically, the resist composition contains the polymer, a photoacid generator, and an organic solvent, and other optional components.

The polymer is not limited to one type and a mixture of two or more polymers may be added. The use of plural polymers allows for easy adjustment of resist properties.

Photoacid Generator

The resist composition of the invention also comprises a compound which generates an acid in response to actinic light or radiation (referred to as "photoacid generator"). The photoacid generator may be any compound which generates an acid upon exposure to high-energy radiation and specifically, any of well-known photoacid generators which are commonly used in prior art resist compositions, especially chemically amplified resist compositions. Suitable photoacid generators include sulfonium salts, iodonium salts, sulfonyldiazomethane, N-sulfonyloxyimide, and oxime-O-sulfonate acid generators. Exemplary acid generators are given below while they may be used alone or in admixture of two or more.

Sulfonium salts are salts of sulfonium cations with sulfonates, bis(substituted alkylsulfonyl)imides and tris(substituted alkylsulfonyl)methides. Exemplary sulfonium cations include triphenylsulfonium, (4-tert-butoxyphenyl)diphenylsulfonium, bis(4-tert-butoxyphenyl)phenylsulfonium, tris(4-tert-butoxyphenyl)sulfonium, (3-tert-butoxyphenyl)diphenylsulfonium, bis(3-tert-butoxyphenyl)phenylsulfonium, tris(3-tert-butoxyphenyl)sulfonium, (3,4-di-tert-butoxyphenyl)diphenylsulfonium, bis(3,4-di-tert-butoxyphenyl)phenylsulfonium, tris(3,4-di-tert-butoxyphenyl)sulfonium, diphenyl(4-thiophenoxyphenyl)sulfonium, (4-tert-butoxycarbonylmethyloxyphenyl)diphenylsulfonium, tris(4-tert-butoxycarbonylmethyloxyphenyl)sulfonium, (4-tert-butoxyphenyl)bis(4-dimethylaminophenyl)sulfonium, tris(4-dimethylaminophenyl)sulfonium, 2-naphthyldiphenylsulfonium, dimethyl-2-naphthylsulfonium, 4-hydroxyphenyldimethylsulfonium, 4-methoxyphenyldimethylsulfonium, trimethylsulfonium, 2-oxocyclohexylcyclohexylmethylsulfonium, trinaphthylsulfonium, tribenzylsulfonium, diphenylmethylsulfonium, dimethylphenylsulfonium, 2-oxo-2-phenylethylthiacyclopentanium, 4-n-butoxynaphthyl-1-thiacyclopentanium, and 2-n-butoxynaphthyl-1-thiacyclopentanium. Exemplary sulfonates include trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, 4-(4'-toluenesulfonyloxy)benzenesulfonate, naphthalenesulfonate, camphorsulfonate, octanesulfonate, dodecylbenzenesulfonate, butanesulfonate, methanesulfonate, 1,1-difluoro-2-naphthylethanesulfonate, 1,1,2,2-tetrafluoro-2-(norbornan-2-yl)ethanesulfonate, 1,1,2,2-tetrafluoro-2-(tetracyclo[4.4.0.1$^{2,5}$.1$^{7,10}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H- cyclopenta[b]furan-6-yloxycarbonyl)difluoromethanesulfonate, and 4-oxo-1-adamantyloxycarbonyldifluoromethanesulfonate.

Exemplary bis(substituted alkylsulfonyl)imides include bistrifluoromethylsulfonylimide, bispentafluoroethylsulfonylimide, bisheptafluoropropylsulfonylimide, and perfluoro-1,3-propylenebissulfonylimide. A typical tris(substituted alkylsulfonyl)methide is tristrifluoromethylsulfonylmethide. Sulfonium salts based on combination of the foregoing examples are included.

Iodonium salts are salts of iodonium cations with sulfonates, bis(substituted alkylsulfonyl)imides and tris(substituted alkylsulfonyl)methides. Exemplary iodonium cations are aryliodonium cations including diphenyliodinium, bis(4-tert-butylphenyl)iodonium, 4-tert-butoxyphenylphenyliodonium, and 4-methoxyphenylphenyliodonium. Exemplary sulfonates include trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, 4-(4-toluenesulfonyloxy)benzenesulfonate, naphthalenesulfonate, camphorsulfonate, octanesulfonate, dodecylbenzenesulfonate, butanesulfonate, methanesulfonate, 1,1-difluoro-2-naphthylethanesulfonate, 1,1,2,2-tetrafluoro-2-(norbornan-2-yl)ethanesulfonate, 1,1,2,2-tetrafluoro-2-(tetracyclo[4.4.0.1$^{2,5}$.1$^{7,10}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, adamantanemethoxycarbonyldifluoromethanesulfonate, 1-(3-hydroxymethyladamantane) methoxycarbonyldifluoromethanesulfonate, methoxycarbonyldifluoromethanesulfonate, 1-(hexahydro-2-oxo-3,5-methano-2H-cyclopenta[b]furan-6-yloxycarbonyl)difluoromethanesulfonate, and 4-oxo-1-adamantyloxycarbonyldifluoromethanesulfonate.

Exemplary bis(substituted alkylsulfonyl)imides include bistrifluoromethylsulfonylimide, bispentafluoroethylsulfonylimide, bisheptafluoropropylsulfonylimide, and perfluoro-1,3-propylenebissulfonylimide. A typical tris(substituted alkylsulfonyl)methide is tristrifluoromethylsulfonylmethide. Iodonium salts based on combination of the foregoing examples are included.

Exemplary sulfonyldiazomethane compounds include bissulfonyldiazomethane compounds and sulfonylcarbonyldiazomethane compounds such as bis(ethylsulfonyl)diazomethane, bis(1-methylpropylsulfonyl)diazomethane, bis(2-methylpropylsulfonyl)diazomethane, bis(1,1-dimethylethylsulfonyl)diazomethane, bis(cyclohexylsulfonyl)diazomethane, bis(perfluoroisopropylsulfonyl)diazomethane, bis(phenylsulfonyl)diazomethane, bis(4-methylphenylsulfonyl)diazomethane, bis(2,4-dimethylphenylsulfonyl)diazomethane, bis(2-naphthylsulfonyl)diazomethane, bis(4-acetyloxyphenylsulfonyl)diazomethane, bis(4-methanesulfonyloxyphenylsulfonyl)diazomethane, bis(4-(4-toluenesulfonyloxy)phenylsulfonyl)diazomethane, bis(4-(n-hexyloxy)phenylsulfonyl)diazomethane, bis(2-methyl-4-(n-hexyloxy)phenylsulfonyl)diazomethane, bis(2,5-dimethyl-4-(n-hexyloxy)phenylsulfonyl)diazomethane, bis(3,5-dimethyl-4-(n-hexyloxy)phenylsulfonyl)diazomethane, bis(2-methyl-5-isopropyl-4-(n-hexyloxy)phenylsulfonyl)diazomethane, 4-methylphenylsulfonylbenzoyldiazomethane, tert-butylcarbonyl-4-methylphenylsulfonyldiazomethane, 2-naphthylsulfonylbenzoyldiazomethane, 4-methylphenylsulfonyl-2-naphthoyldiazomethane, methylsulfonylbenzoyldiazomethane, and tert-butoxycarbonyl-4-methylphenylsulfonyldiazomethane.

N-sulfonyloxyimide photoacid generators include combinations of imide skeletons with sulfonates. Exemplary imide skeletons are succinimide, naphthalene dicarboxylic acid imide, phthalimide, cyclohexyldicarboxylic acid imide, 5-norbornene-2,3-dicarboxylic acid imide, and 7-oxabicyclo[2.2.1]-5-heptene-2,3-dicarboxylic acid imide. Exemplary sulfonates include trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, mesitylenesulfonate, 2,4,6-triisopropylbenzenesulfonate, toluenesulfonate, benzenesulfonate, naphthalenesulfonate, camphorsulfonate, octanesulfonate, dodecylbenzenesulfonate, butanesulfonate, methanesulfonate, 1,1-difluoro-2-naphthylethanesulfonate, 1,1,2,2-tetrafluoro-2-(norbornan-2-yl)ethanesulfonate, 1,1,2,2-tetrafluoro-2-(tetracyclo[4.4.0.1$^{2,5}$.1$^{7,10}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yloxycarbonyl)difluoromethanesulfonate, and 4-oxo-1-adamantyloxycarbonyldifluoromethanesulfonate.

Benzoinsulfonate photoacid generators include benzoin tosylate, benzoin mesylate, and benzoin butanesulfonate.

Pyrogallol trisulfonate photoacid generators include pyrogallol, phloroglucinol, catechol, resorcinol, and hydroquinone, in which all the hydroxyl groups are substituted by trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, methanesulfonate, 1,1-difluoro-2-naphthylethanesulfonate, 1,1,2,2-tetrafluoro-2-(norbornan-2-yl)ethanesulfonate, 1,1,2,2-tetrafluoro-2-(tetracyclo[4.4.0.1$^{2,5}$.1$^{7,10}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropanesulfonate, 2-adamantanecarbonyloxy-1,1,3,3,3-pentafluoropropane-sulfonate, 2-acetyloxy-1,1,3,3,3-pentafluoropropane-sulfonate, 1,1,3,3,3-pentafluoro-2-hydroxypropane-sulfonate, 1,1,3,3,3-pentafluoro-2-tosyloxypropanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yloxycarbonyl)difluoromethanesulfonate, and 4-oxo-1-adamantyloxycarbonyldifluoromethanesulfonate.

Nitrobenzyl sulfonate photoacid generators include 2,4-dinitrobenzyl sulfonate, 2-nitrobenzyl sulfonate, and 2,6-dinitrobenzyl sulfonate, with exemplary sulfonates including trifluoromethanesulfonate, pentafluoroethanesulfonate, nonafluorobutanesulfonate, dodecafluorohexanesulfonate, pentafluoroethylperfluorocyclohexanesulfonate, heptadecafluorooctanesulfonate, 2,2,2-trifluoroethanesulfonate, pentafluorobenzenesulfonate, 4-trifluoromethylbenzenesulfonate, 4-fluorobenzenesulfonate, toluenesulfonate, benzenesulfonate, naphthalenesulfonate, camphorsulfonate, octanesulfonate, dodecylbenzenesulfonate, butanesulfonate, methanesulfonate, 1,1-difluoro-2-naphthylethanesulfonate, 1,1,2,2-tetrafluoro-2-(norbornan-2-yl)ethanesulfonate, 1,1,2,2-tetrafluoro-2-(tetracyclo[4.4.0.1$^{2,5}$.1$^{7,10}$]dodec-3-en-8-yl)ethanesulfonate, 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-adamantanecarbonyloxy-1,1,3,3,3-pentafluoropropane-sulfonate, 2-acetyloxy-1,1,3,3,3-pentafluoropropane-sulfonate, 1,1,3,3,3-pentafluoro-2-hydroxypropane-sulfonate, 1,1,3,3,3-pentafluoro-2-tosyloxypropanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yl-oxycarbonyl)difluoromethanesulfonate, and 4-oxo-1-adamantyloxycarbonyldifluoromethanesulfonate. Also useful are analogous nitrobenzyl sulfonate compounds in which the nitro group on the benzyl side is substituted by a trifluoromethyl group.

Sulfone photoacid generators include bis(phenylsulfonyl)methane, bis(4-methylphenylsulfonyl)methane, bis(2-naphthylsulfonyl)methane, 2,2-bis(phenylsulfonyl)propane, 2,2-bis(4-methylphenylsulfonyl)propane, 2,2-bis(2-naphthylsulfonyl)propane, 2-methyl-2-(p-toluenesulfonyl)propiophenone, 2-cyclohexylcarbonyl-2-(p-toluenesulfonyl)propane, and 2,4-dimethyl-2-(p-toluenesulfonyl)pentan-3-one.

Photoacid generators in the form of glyoxime derivatives are described in Japanese Patent No. 2,906,999 and JP-A 9-301948 and include bis-O-(p-toluenesulfonyl)-α-dimethylglyoxime, bis-O-(p-toluenesulfonyl)-α-diphenylglyoxime, bis-O-(p-toluenesulfonyl)-α-dicyclohexylglyoxime, bis-O-(p-toluenesulfonyl)-2,3-pentanedioneglyoxime, bis-O-(n-butanesulfonyl)-α-dimethylglyoxime, bis-O-(n-butanesulfonyl)-α-diphenylglyoxime, bis-O-(n-butanesulfonyl)-α-dicyclohexylglyoxime, bis-O-(methanesulfonyl)-α-dimethylglyoxime, bis-O-(trifluoromethanesulfonyl)-α-dimethylglyoxime, bis-O-(2,2,2-trifluoroethanesulfonyl)-α-dimethylglyoxime, bis-O-(10-camphorsulfonyl)-α-dimethylglyoxime, bis-O-(benzenesulfonyl)-α-dimethylglyoxime, bis-O-(p-fluorobenzenesulfonyl)-α-dimethylglyoxime, bis-O-(p-trifluoromethylbenzenesulfonyl)-α-dimethylglyoxime, bis-O-(xylenesulfonyl)-α-dimethylglyoxime, bis-O-(trifluoromethanesulfonyl)-nioxime, bis-O-(2,2,2-trifluoroethanesulfonyl)-nioxime, bis-O-(10-camphorsulfonyl)-nioxime, bis-O-(benzenesulfonyl)-nioxime, bis-O-(p-fluorobenzenesulfonyl)-nioxime, bis-O-(p-trifluoromethylbenzenesulfonyl)-nioxime, and bis-O-(xylenesulfonyl)-nioxime. Also included are compounds of the foregoing skeleton having substituted thereon 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropane-sulfonate, 1,1,3,3,3-pentafluoro-2-furoyloxypropane-sulfonate, 2-naphthoyloxy-1,1,3,3,3-pentafluoropropane-sulfonate, 2-(4-tert-butylbenzoyloxy)-1,1,3,3,3-pentafluoropropane-sulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yl-oxycarbonyl)difluoromethanesulfonate, and 4-oxo-1-adamantyloxycarbonyldifluoromethanesulfonate.

Also included are the oxime sulfonates described in U.S. Pat. No. 6,004,724, for example, (5-(4-toluenesulfonyl)oxyimino-5H-thiophen-2-ylidene)phenylacetonitrile, (5-(10-camphorsulfonyl)oxyimino-5H-thiophen-2-ylidene)phenylacetonitrile, (5-n-octanesulfonyloxyimino-5H-thiophen-2-ylidene)phenylacetonitrile, (5-(4-toluenesulfonyl)oxyimino-5H-thiophen-2-ylidene)(2-methylphenyl)acetonitrile, (5-(10-camphorsulfonyl)oxyimino-5H-thiophen-2-ylidene)(2-methylphenyl)acetonitrile, (5-n-octanesulfonyloxyimino-5H-thiophen-2-ylidene)(2-methylphenyl)acetonitrile, etc.

Also included are the oxime sulfonates described in U.S. Pat. No. 6,916,591, for example, (5-(4-(4-toluenesulfonyloxy)benzenesulfonyl)oxyimino-5H-thiophen-2-ylidene)phenylacetonitrile and (5-(2,5-bis(4-toluenesulfonyloxy)benzenesulfonyl)oxyimino-5H-thiophen-2-ylidene)phenylacetonitrile. Also included are compounds of the foregoing skeleton having substituted thereon 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropane-sulfonate, 1,1,3,3,3-pentafluoro-2-furoyloxypropane-sulfonate, 2-naphthoyloxy-1,1,3,3,3-pentafluoropropane-sulfonate, 2-(4-tert-butylbenzoyloxy)-1,1,3,3,3- pentafluoropropane-sulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yl-oxycarbonyl)difluoromethanesulfonate, and 4-oxo-1-adamantyloxycarbonyldifluoromethanesulfonate.

Also included are the oxime sulfonates described in U.S. Pat. No. 6,261,738 and JP-A 2000-314956, for example, 2,2,2-trifluoro-1-phenyl-ethanone oxime-O-methylsulfonate; 2,2,2-trifluoro-1-phenyl-ethanone oxime-O-(10-camphorylsulfonate); 2,2,2-trifluoro-1-phenyl-ethanone oxime-O-(4-methoxyphenylsulfonate); 2,2,2-trifluoro-1-phenyl-ethanone oxime-O-(1-naphthylsulfonate); 2,2,2-trifluoro-1-phenyl-ethanone oxime-O-(2-naphthylsulfonate); 2,2,2-trifluoro-1-phenyl-ethanone oxime-O-(2,4,6-trimethylphenylsulfonate); 2,2,2-trifluoro-1-(4-methylphenyl)-ethanone oxime-O-(10-camphorylsulfonate); 2,2,2-trifluoro-1-(4-methylphenyl)-ethanone oxime-O-(methylsulfonate); 2,2,2-trifluoro-1-(2-methylphenyl)-ethanone oxime-O-(10-camphorylsulfonate); 2,2,2-trifluoro-1-(2,4-dimethylphenyl)-ethanone oxime-O-(10-camphorylsulfonate); 2,2,2-trifluoro-1-(2,4-dimethylphenyl)-ethanone oxime-O-(1-naphthylsulfonate); 2,2,2-trifluoro-1-(2,4-dimethylphenyl)-ethanone oxime-O-(2-naphthylsulfonate); 2,2,2-trifluoro-1-(2,4,6-trimethylphenyl)-ethanone oxime-O-(10-camphorylsulfonate); 2,2,2-trifluoro-1-(2,4,6-trimethylphenyl)-ethanone oxime-O-(1-naphthylsulfonate); 2,2,2-trifluoro-1-(2,4,6-trimethylphenyl)-ethanone oxime-O-2-naphthylsulfonate); 2,2,2-trifluoro-1-(4-methoxyphenyl)-ethanone oxime-O-methylsulfonate; 2,2,2-trifluoro-1-(4-methylthiophenyl)-ethanone oxime-O-methylsulfonate; 2,2,2-trifluoro-1-(3,4-dimethoxyphenyl)-ethanone oxime-O-methylsulfonate; 2,2,3,3,4,4,4-heptafluoro-1-phenyl-butanone oxime-O-(10-camphorylsulfonate); 2,2,2-trifluoro-1-(phenyl)-ethanone oxime-O-methylsulfonate; 2,2,2-trifluoro-1-(phenyl)-ethanone oxime-O-10-camphorylsulfonate; 2,2,2-trifluoro-1-(phenyl)-ethanone oxime-O-(4-methoxyphenyl)sulfonate; 2,2,2-trifluoro-1-(phenyl)-ethanone oxime-O-(1-naphthyl)sulfonate; 2,2,2-trifluoro-1-(phenyl)-ethanone oxime-O-(2-naphthyl)sulfonate; 2,2,2-trifluoro-1-(phenyl)-ethanone oxime-O-(2,4,6-trimethylphenyl)sulfonate; 2,2,2-trifluoro-1-(4-methylphenyl)-ethanone oxime-O-(10-camphoryl)sulfonate; 2,2,2-trifluoro-1-(4-methylphenyl)-ethanone oxime-O-methylsulfonate; 2,2,2-trifluoro-1-(2-methylphenyl)-ethanone oxime-O-(10-camphoryl)sulfonate; 2,2,2-trifluoro-1-(2,4-dimethylphenyl)-ethanone oxime-O-(1-naphthyl)sulfonate; 2,2,2-trifluoro-1-(2,4-dimethylphenyl)-ethanone oxime-O-(2-naphthyl)sulfonate; 2,2,2-trifluoro-1-(2,4,6-trimethyl-phenyl)-ethanone oxime-O-(10-camphoryl) sulfonate; 2,2,2-trifluoro-1-(2,4,6-trimethylphenyl)-ethanone oxime-O-(1-naphthyl)sulfonate; 2,2,2-trifluoro-1-(2,4,6-trimethyl-phenyl)-ethanone oxime-O-(2-naphthyl) sulfonate; 2,2,2-trifluoro-1-(4-methoxyphenyl)-ethanone oxime-O-methylsulfonate; 2,2,2-trifluoro-1-(4-thiomethylphenyl)-ethanone oxime-O-methylsulfonate; 2,2,2-trifluoro-1-(3,4-dimethoxyphenyl)-ethanone oxime-O-methylsulfonate; 2,2,2-trifluoro-1-(4-methoxyphenyl)-ethanone oxime-O-(4-methylphenyl)sulfonate; 2,2,2-trifluoro-1-(4-methoxyphenyl)-ethanone oxime-O-(4-methoxyphenyl)sulfonate; 2,2,2-trifluoro-1-(4-methoxyphenyl)-ethanone oxime-O-(4-dodecylphenyl)-sulfonate; 2,2,2-trifluoro-1-(4-methoxyphenyl)-ethanone oxime-O-octylsulfonate; 2,2,2-trifluoro-1-(4-thiomethyl-phenyl)-ethanone oxime-O-(4-methoxyphenyl)sulfonate; 2,2,2-trifluoro-1-(4-thiomethylphenyl)-ethanone oxime-O-(4-dodecylphenyl) sulfonate; 2,2,2-trifluoro-1-(4-thiomethyl-phenyl)-ethanone oxime-O-octylsulfonate; 2,2,2-trifluoro-1-(4-thiomethylphenyl)-ethanone oxime-O-(2-naphthyl)sulfonate; 2,2,2-trifluoro-1-(2-methylphenyl)-ethanone oxime-O-methylsulfonate; 2,2,2-trifluoro-1-(4-methylphenyl)ethanone oxime-O-phenylsulfonate; 2,2,2-trifluoro-1-(4-chlorophenyl)-ethanone oxime-O-phenylsulfonate; 2,2,3,3,4,4,4-heptafluoro-1-(phenyl)-butanone oxime-O-(10-camphoryl) sulfonate; 2,2,2-trifluoro-1-naphthyl-ethanone oxime-O-methylsulfonate; 2,2,2-trifluoro-2-naphthyl-ethanone oxime-O-methylsulfonate; 2,2,2-trifluoro-1-[4-benzylphenyl]-ethanone oxime-O-methylsulfonate; 2,2,2-trifluoro-1-[4-(phenyl-1,4-dioxa-but-1-yl)phenyl]-ethanone oxime-O-methylsulfonate; 2,2,2-trifluoro-1-naphthyl-ethanone oxime-O-propylsulfonate; 2,2,2-trifluoro-2-naphthyl-ethanone oxime-O-propylsulfonate; 2,2,2-trifluoro-1-[4-benzylphenyl]-ethanone oxime-O-propylsulfonate; 2,2,2-trifluoro-1-[4-methylsulfonylphenyl]-ethanone oxime-O-propylsulfonate; 1,3-bis[1-(4-phenoxy-phenyl)-2,2,2-trifluoroethanone oxime-O-sulfonyl]phenyl; 2,2,2-trifluoro-1-[4-methylsulfonyloxyphenyl]-ethanone oxime-O-propylsulfonate; 2,2,2-trifluoro-1-[4-methylcarbonyloxyphenyl]-ethanone oxime-O-propylsulfonate; 2,2,2-trifluoro-1-[6H,7H-5,8-dioxonaphth-2-yl]-ethanone oxime-O-propylsulfonate; 2,2,2-trifluoro-1-[4-methoxycarbonylmethoxyphenyl]-ethanone oxime-O-propylsulfonate; 2,2,2-trifluoro-1-[4-(methoxycarbonyl)-(4-amino-1-oxa-pent-1-yl)-phenyl]-ethanone oxime-O-propylsulfonate; 2,2,2-trifluoro-1-[3,5-dimethyl-4-ethoxyphenyl]-ethanone oxime-O-propylsulfonate; 2,2,2-trifluoro-1-[4-benzyloxyphenyl]-ethanone oxime-O-propylsulfonate; 2,2,2-trifluoro-1-[2-thiophenyl]-ethanone oxime-O-propylsulfonate; 2,2,2-trifluoro-1-[1-dioxa-thiophen-2-yl)]-ethanone oxime-O-propylsulfonate; 2,2,2-trifluoro-1-(4-(3-(4-(2,2,2-trifluoro-1-(trifluoromethanesulfonyloxyimino)-ethyl)-phenoxy)-propoxy)-phenyl)ethanone oxime (trifluoromethanesulfonate); 2,2,2-trifluoro-1-(4-(3-(4-(2,2,2-trifluoro-1-(1-propanesulfonyloxyimino)-ethyl)-phenoxy)-propoxy)-phenyl)-ethanone oxime(1-propanesulfonate); and 2,2,2-trifluoro-1-(4-(3-(4-(2,2,2-trifluoro-1-(1-butanesulfonyloxyimino)-ethyl)-phenoxy)-propoxy)-phenyl)ethanone oxime(1-butanesulfonate). Also included are the oxime sulfonates described in U.S. Pat. No. 6,916,591, for example, 2,2,2-trifluoro-1-(4-(3-(4-(2,2,2-trifluoro-1-(4-(4-methylphenylsulfonyloxy)-phenylsulfonyloxyimino)-ethyl)-phenoxy)-propoxy)-phenyl)ethanone oxime(4-(4-methylphenylsulfonyloxy)-phenylsulfonate) and 2,2,2-trifluoro-1-(4-(3-(4-(2,2,2-trifluoro-1-(2,5-bis(4-methylphenylsulfonyloxy)-benzenesulfonyloxy)phenylsulfonyloxyimino)-ethyl)-phenoxy)-propoxy)-phenyl)ethanone oxime(2,5-bis(4-methylphenyl-sulfonyloxy)benzenesulfonyloxy)phenylsulfonate). Also included are compounds of the foregoing skeleton having substituted thereon 2-benzoyloxy-1,1,3,3,3-pentafluoropropane-sulfonate, 1,1,3,3,3-pentafluoro-2-(4-phenylbenzoyl-oxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1, 1,3,3,3-pentafluoropropanesulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, adamantanemethoxycarbonyldifluoromethanesulfonate, 1-(3-hydroxymethyladamantane)methoxycarbonyldifluoromethanesulfonate, methoxycarbonyldifluoromethanesulfonate, 1-(hexahydro-2-oxo-3,5-methano-2H-cyclopenta[b]furan-6-yl-oxycarbonyl)difluoromethanesulfonate, and 4-oxo-1-adamantyloxycarbonyldifluoromethanesulfonate.

Also included are the oxime sulfonates described in JP-A 9-95479 and JP-A 9-230588 and the references cited therein, for example, α-(p-toluenesulfonyloxyimino)-phenylacetonitrile, α-(p-chlorobenzenesulfonyloxyimino)-phenylacetonitrile, α-(4-nitrobenzenesulfonyloxyimino)-phenylacetonitrile, α-(4-nitro-2-trifluoromethylbenzenesulfonyloxyimino)-phenylacetonitrile, α-(benzenesulfonyloxyimino)-4-chlorophenylacetonitrile, α-(benzenesulfonyloxyimino)-2,4-dichlorophenylacetonitrile, α-(benzenesulfonyloxyimino)-2,6-dichlorophenylacetonitrile, α-(benzenesulfonyloxyimino)-4-methoxyphenylacetonitrile, α-(2-chlorobenzenesulfonyloxyimino)-4-methoxyphenylacetonitrile, α-(benzenesulfonyloxyimino)-2-thienylacetonitrile, α-(4-dodecylbenzenesulfonyloxyimino)-phenylacetonitrile, α-[(4-toluenesulfonyloxyimino)-4-methoxyphenyl]acetonitrile, α-[(dodecylbenzenesulfonyloxyimino)-4-methoxyphenyl]acetonitrile, α-(tosyloxyimino)-3-thienylacetonitrile, α-(methylsulfonyloxyimino)-1-cyclopentenylacetonitrile, α-(ethylsulfonyloxyimino)-1-cyclopentenylacetonitrile, α-(isopropylsulfonyloxyimino)-1-cyclopentenylacetonitrile, α-(n-butylsulfonyloxyimino)-1-cyclopentenylacetonitrile, α-(ethylsulfonyloxyimino)-1-cyclohexenylacetonitrile, α-(isopropylsulfonyloxyimino)-1-cyclohexenylacetonitrile, and α-(n-butylsulfonyloxyimino)-1-cyclohexenylacetonitrile. Also included are compounds of the foregoing skeleton having substituted thereon 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-cyclopenta[b]furan-6-yl-oxycarbonyl)difluoromethanesulfonate, and 4-oxo-1-adamantyloxycarbonyldifluoromethanesulfonate.

Also included are oxime sulfonates having the formula:

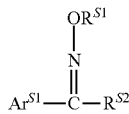

wherein $R^{s1}$ is a substituted or unsubstituted haloalkylsulfonyl or halobenzenesulfonyl group of 1 to 10 carbon atoms, $R^{s2}$ is a haloalkyl group of 1 to 11 carbon atoms, and $Ar^{s1}$ is substituted or unsubstituted aromatic or hetero-aromatic group, as described in WO 2004/074242. Examples include 2-[2,2,3,3,4,4,5,5-octafluoro-1-(nonafluoro-butylsulfonyloxyimino)-pentyl]-fluorene, 2-[2,2,3,3,4,4-pentafluoro-1-(nonafluorobutylsulfonyloxy-imino)-butyl]-fluorene, 2-[2,2,3,3,4,4,5,5,6,6-decafluoro-1-(nonafluorobutylsulfonyl-oxyimino)-hexyl]-fluorene, 2-[2,2,3,3,4,4,5,5-octafluoro-1-(nonafluorobutylsulfonyloxy-imino)-pentyl]-4-biphenyl, 2-[2,2,3,3,4,4-pentafluoro-1-(nonafluorobutylsulfonyloxy-imino)-butyl]-4-biphenyl, and 2-[2,2,3,3,4,4,5,5,6,6-decafluoro-1-(nonafluorobutylsulfonyl-oxyimino)-hexyl]-4-biphenyl. Also included are compounds of the foregoing skeleton having substituted thereon 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, adamantanemethoxycarbonyldifluoromethanesulfonate, 1-(3-hydroxymethyladamantane)methoxycarbonyldifluoromethane-sulfonate, methoxycarbonyldifluoromethanesulfonate, 1-(hexahydro-2-oxo-3,5-methano-2H-

Suitable bisoxime sulfonates include those described in JP-A 9-208554, for example, bis(α-(4-toluenesulfonyloxy)imino)-p-phenylenediacetonitrile, bis(α-(benzenesulfonyloxy)imino)-p-phenylenediacetonitrile, bis(α-(methanesulfonyloxy)imino)-p-phenylenediacetonitrile, bis(α-(butanesulfonyloxy)imino)-p-phenylenediacetonitrile, bis(α-(10-camphorsulfonyloxy)imino)-p-phenylenediacetonitrile, bis(α-(4-toluenesulfonyloxy)imino)-p-phenylenediacetonitrile, bis(α-(trifluoromethanesulfonyloxy)imino)-p-phenylenediacetonitrile, bis(α-(4-methoxybenzenesulfonyloxy)imino)-p-phenylenediaceto-nitrile, bis(α-(4-toluenesulfonyloxy)imino)-m-phenylenediacetonitrile, bis(α-(benzenesulfonyloxy)imino)-m-phenylenediacetonitrile, bis(α-(methanesulfonyloxy)imino)-m-phenylenediacetonitrile, bis(α-(butanesulfonyloxy)imino)-m-phenylenediacetonitrile, bis(α-(10-camphorsulfonyloxy)imino)-m-phenylenediacetonitrile, bis(α-(4-toluenesulfonyloxy)imino)-m-phenylenediacetonitrile, bis(α-(trifluoromethanesulfonyloxy)imino)-m-phenylenediaceto-nitrile, and bis(α-(4-methoxybenzenesulfonyloxy)imino)-m-phenylenediaceto-nitrile. Also included are compounds of the foregoing skeleton having substituted thereon 2-benzoyloxy-1,1,3,3,3-pentafluoropropanesulfonate, 1,1,3,3,3-pentafluoro-2-(4-phenylbenzoyloxy)propanesulfonate, 1,1,3,3,3-pentafluoro-2-pivaloyloxypropanesulfonate, 2-cyclohexanecarbonyloxy-1,1,3,3,3-pentafluoropropanesulfonate, 1,1,3,3,3-pentafluoro-2-furoyloxypropanesulfonate, 2-naphthoyloxy-1,1,3,3,3-pentafluoropropanesulfonate, 2-(4-tert-butylbenzoyloxy)-1,1,3,3,3-pentafluoropropane-sulfonate, 2-adamantanecarbonyloxy-1,1,3,3,3-pentafluoropropanesulfonate, 2-acetyloxy-1,1,3,3,3-pentafluoropropanesulfonate, 1,1,3,3,3-pentafluoro-2-hydroxypropanesulfonate, 1,1,3,3,3-pentafluoro-2-tosyloxypropanesulfonate, adamantanemethoxycarbonyldifluoromethanesulfonate, 1-(3-hydroxymethyladamantane) methoxycarbonyldifluoromethane-sulfonate, methoxycarbonyldifluoromethanesulfonate, 1-(hexahydro-2-oxo-3,5-methano-2H- cyclopenta[b]furan-6-yl-oxycarbonyl)difluoromethanesulfonate, and 4-oxo-1-adamantyloxycarbonyldifluoromethanesulfonate.

Of these, preferred photoacid generators are sulfonium salts, bissulfonyldiazomethanes, N-sulfonyloxyimides, oxime-O-sulfonates and glyoxime derivatives. More preferred photoacid generators are sulfonium salts, bissulfonyldiazomethanes, N-sulfonyloxyimides, and oxime-O-sulfonates. Typical examples include triphenylsulfonium p-toluenesulfonate, triphenylsulfonium camphorsulfonate, triphenylsulfonium pentafluorobenzenesulfonate, triphenylsulfonium nonafluorobutanesulfonate, triphenylsulfonium 4-(4'-toluenesulfonyloxy)benzenesulfonate, triphenylsulfonium 2,4,6-triisopropylbenzenesulfonate, 4-tert-butoxyphenyldiphenylsulfonium p-toluenesulfonate, 4-tert-butoxyphenyldiphenylsulfonium camphorsulfonate, 4-tert-butoxyphenyldiphenylsulfonium 4-(4'-toluenesulfonyl-oxy)benzenesulfonate, tris(4-methylphenyl)sulfonium camphorsulfonate, tris(4-tert-butylphenyl)sulfonium camphorsulfonate, 4-tert-butylphenyldiphenylsulfonium camphorsulfonate, 4-tert-butylphenyldiphenylsulfonium nonafluoro-1-butanesulfonate, 4-tert-butylphenyldiphenylsulfonium pentafluoroethylperfluorocyclohexanesulfonate, 4-tert-butylphenyldiphenylsulfonium perfluoro-1-octanesulfonate, triphenylsulfonium 1,1-difluoro-2-naphthylethanesulfonate, triphenylsulfonium 1,1,2,2-tetrafluoro-2-(norbornan-2-yl)-ethanesulfonate, triphenylsulfonium 2-benzoyloxy-1,1,3,3,3-pentafluoropropanesulfonate, triphenylsulfonium 1,1,3,3,3-pentafluoro-2-(pivaloyloxy)-propanesulfonate, triphenylsulfonium 2-cyclohexanecarbonyloxy-1,1,3,3,3-pentafluoropropanesulfonate, triphenylsulfonium 2-(2-naphthoyloxy)-1,1,3,3,3-pentafluoropropanesulfonate, triphenylsulfonium adamantanemethoxycarbonyldifluoromethanesulfonate, triphenylsulfonium 1-(3-hydroxymethyladamantane)methoxycarbonyldifluoromethanesulfonate, triphenylsulfonium methoxycarbonyldifluoromethanesulfonate, 4-tert-butylphenyldiphenylsulfonium 2-benzoyloxy-1,1,3,3,3-pentafluoropropanesulfonate, 4-tert-butylphenyldiphenylsulfonium 1,1,3,3,3-pentafluoro-2-(pivaloyloxy)propanesulfonate, 4-tert-butylphenyldiphenylsulfonium 2-cyclohexanecarbonyloxy-1,1,3,3,3-pentafluoropropanesulfonate, 4-tert-butylphenyldiphenylsulfonium 2-(2-naphthoyloxy)-1,1,3,3,3-pentafluoropropanesulfonate, 4-tert-butylphenyldiphenylsulfonium adamantanemethoxycarbonyldifluoromethanesulfonate, 4-tert-butylphenyldiphenylsulfonium 1-(3-hydroxymethyladamantane)methoxycarbonyldifluoromethanesulfonate, 4-tert-butylphenyldiphenylsulfonium methoxycarbonyldifluoromethanesulfonate, 2-oxo-2-phenylethylthiacyclopentanium 2-benzoyloxy-1,1,3,3,3-pentafluoropropanesulfonate, 2-oxo-2-phenylethylthiacyclopentanium 2-cyclohexanecarbonyloxy-1,1,3,3,3-pentafluoropropanesulfonate, triphenylsulfonium perfluoro-1,3-propylenebissulfonylimide, triphenylsulfonium bispentafluoroethylsulfonylimide, bis(tert-butylsulfonyl)diazomethane, bis(cyclohexylsulfonyl)diazomethane, bis(2,4-dimethylphenylsulfonyl)diazomethane, bis(4-(n-hexyloxy)phenylsulfonyl)diazomethane, bis(2-methyl-4-(n-hexyloxy)phenylsulfonyl)diazomethane, bis(2,5-dimethyl-4-(n-hexyloxy)phenylsulfonyl)diazomethane, bis(3,5-dimethyl-4-(n-hexyloxy)phenylsulfonyl)diazomethane, bis(2-methyl-5-isopropyl-4-(n-hexyloxy)phenylsulfonyl)-diazomethane, bis(4-tert-butylphenylsulfonyl)diazomethane, N-camphorsulfonyloxy-5-norbornene-2,3-dicarboxylic acid imide, N-p-toluenesulfonyloxy-5-norbornene-2,3-dicarboxylic acid imide, 2-[2,2,3,3,4,4,5,5-octafluoro-1-(nonafluorobutylsulfonyloxy-imino)-pentyl]-fluorene, 2-[2,2,3,3,4,4-pentafluoro-1-(nonafluorobutylsulfonyloxy-imino)-butyl]-fluorene, 2-[2,2,3,3,4,4,5,5,6,6-decafluoro-1-(nonafluorobutylsulfonyl-oxyimino)-hexyl]-fluorene, 2-[2,2,3,3,4,4,5,5-octafluoro-1-(2-(cyclohexanecarbonyloxy)-1,1,3,3,3-pentafluoropropanesulfonyloxyimino)-pentyl]-fluorene, 2-[2,2,3,3,4,4-pentafluoro-1-(2-(cyclohexanecarbonyloxy)-1,1,3,3,3-pentafluoropropanesulfonyloxyimino)-butyl]-fluorene, and 2-[2,2,3,3,4,4,5,5,6,6-decafluoro-1-(nonafluorobutyl-sulfonyloxyimino)-hexyl]-fluorene.

In the resist composition, an appropriate amount of the photoacid generator is, but not limited to, 0.1 to 10 parts, and especially 0.1 to 5 parts by weight per 100 parts by weight of the base resin. Too high a proportion of the photoacid generator may give rise to problems of degraded resolution and foreign matter upon development and resist film peeling. The photoacid generators may be used alone or in admixture of two or more. The transmittance of the resist film can be controlled by using a photoacid generator having a low transmittance at the exposure wavelength and adjusting the amount of the photoacid generator added.

It is noted that an acid diffusion controlling function may be provided when two or more photoacid generators are used in admixture provided that one photoacid generator is an onium salt capable of generating a weak acid. Specifically, in a system using a mixture of a photoacid generator capable of generating a strong acid (e.g., fluorinated sulfonic acid) and an onium salt capable of generating a weak acid (e.g., non-fluorinated sulfonic acid), if the strong acid generated from the photoacid generator upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If an onium salt capable of generating a strong acid and an onium salt capable of generating a weak acid are used in admixture, an exchange from the strong acid to the weak acid as above can take place, but it never happens that the weak acid collides with the unreacted onium salt capable of generating a strong acid to induce a salt exchange. This is because of a likelihood of an onium cation forming an ion pair with a stronger acid anion.

In the resist composition, there may be added a compound which is decomposed with an acid to generate another acid, that is, acid-amplifier compound. For these compounds, reference should be made to J. Photopolym. Sci. and Tech., 8, 43-44, 45-46 (1995), and ibid., 9, 29-30 (1996).

Examples of the acid-amplifier compound include tert-butyl-2-methyl-2-tosyloxymethyl acetoacetate and 2-phenyl-2-(2-tosyloxyethyl)-1,3-dioxolane, but are not limited thereto. Of well-known photoacid generators, many of those compounds having poor stability, especially poor thermal stability exhibit an acid amplifier-like behavior.

In the resist composition, an appropriate amount of the acid-amplifier compound is up to 2 parts, and especially up to 1 part by weight per 100 parts by weight of the base resin. Excessive amounts of the acid-amplifier compound make diffusion control difficult, leading to degradation of resolution and pattern profile.

Organic Solvent

The organic solvent used herein may be any organic solvent in which the base resin, acid generator, and additives are soluble. Illustrative, non-limiting, examples of the organic solvent include ketones such as cyclohexanone and methyl amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone. These solvents may be used alone or in combinations of two or more thereof. Of the above organic solvents, it is recommended to use diethylene glycol dimethyl ether, 1-ethoxy-2-propanol, propylene glycol monomethyl ether acetate, and mixtures thereof because the acid generator is most soluble therein.

An appropriate amount of the organic solvent used is about 200 to 1,000 parts, especially about 400 to 800 parts by weight per 100 parts by weight of the base resin in the resist composition.

Nitrogen-Containing Compound

In the resist composition, an organic nitrogen-containing compound or compounds may be compounded as a sensitivity regulator. The organic nitrogen-containing compound used herein is preferably a compound capable of suppressing the rate of diffusion when the acid generated by the photoacid generator diffuses within the resist film. The inclusion of organic nitrogen-containing compound holds down the rate of acid diffusion within the resist film, resulting in better resolution. In addition, it suppresses changes in sensitivity following exposure and reduces substrate and environment dependence, as well as improving the exposure latitude and the pattern profile.

The organic nitrogen-containing compound used herein may be any of well-known organic nitrogen-containing compounds which are commonly used in prior art resist compositions, especially chemically amplified resist compositions. Suitable organic nitrogen-containing compounds include primary, secondary, and tertiary aliphatic amines, mixed amines, aromatic amines, heterocyclic amines, nitrogen-containing compounds having carboxyl group, nitrogen-containing compounds having sulfonyl group, nitrogen-containing compounds having hydroxyl group, nitrogen-containing compounds having hydroxyphenyl group, alcoholic nitrogen-containing compounds, amide derivatives, imide derivatives, and carbamate derivatives.

Examples of suitable primary aliphatic amines include ammonia, methylamine, ethylamine, n-propylamine, isopropylamine, n-butylamine, isobutylamine, sec-butylamine, tert-butylamine, pentylamine, tert-amylamine, cyclopentylamine, hexylamine, cyclohexylamine, heptylamine, octylamine, nonylamine, decylamine, dodecylamine, cetylamine, methylenediamine, ethylenediamine, and tetraethylenepentamine. Examples of suitable secondary aliphatic amines include dimethylamine, diethylamine, di-n-propylamine, diisopropylamine, di-n-butylamine, diisobutylamine, di-sec-butylamine, dipentylamine, dicyclopentylamine, dihexylamine, dicyclohexylamine, diheptylamine, dioctylamine, dinonylamine, didecylamine, didodecylamine, dicetylamine, N,N-dimethylmethylenediamine, N,N-dimethylethylenediamine, and N,N-dimethyltetraethylenepentamine. Examples of suitable tertiary aliphatic amines include trimethylamine, triethylamine, tri-n-propylamine, triisopropylamine, tri-n-butylamine, triisobutylamine, tri-sec-butylamine, tripentylamine, tricyclopentylamine, trihexylamine, tricyclohexylamine, triheptylamine, trioctylamine, trinonylamine, tridecylamine, tridodecylamine, tricetylamine, N,N,N',N'-tetramethylmethylenediamine, N,N,N',N'-tetramethylethylenediamine, and N,N,N',N'-tetramethyltetraethylenepentamine.

Examples of suitable mixed amines include dimethylethylamine, methylethylpropylamine, benzylamine, phenethylamine, and benzyldimethylamine. Examples of suitable aromatic and heterocyclic amines include aniline derivatives (e.g., aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, pyrrole derivatives (e.g., pyrrole, 2H-pyrrole, 1-methylpyrrole, 2,4-dimethylpyrrole, 2,5-dimethylpyrrole, and N-methylpyrrole), oxazole derivatives (e.g., oxazole and isooxazole), thiazole derivatives (e.g., thiazole and isothiazole), imidazole derivatives (e.g., imidazole, 4-methylimidazole, and 4-methyl-2-phenylimidazole), pyrazole derivatives, furazan derivatives, pyrroline derivatives (e.g., pyrroline and 2-methyl-1-pyrroline), pyrrolidine derivatives (e.g., pyrrolidine, N-methylpyrrolidine, pyrrolidinone, and N-methylpyrrolidone), imidazoline derivatives, imidazolidine derivatives, pyridine derivatives (e.g., pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 4-pyrrolidinopyridine, 2-(1-ethylpropyl)pyridine, aminopyridine, and dimethylaminopyridine), pyridazine derivatives, pyrimidine derivatives, pyrazine derivatives, pyrazoline derivatives, pyrazolidine derivatives, piperidine derivatives, piperazine derivatives, morpholine derivatives, indole derivatives, isoindole derivatives, 1H-indazole derivatives, indoline derivatives, quinoline derivatives (e.g., quinoline and 3-quinolinecarbonitrile), isoquinoline derivatives, cinnoline derivatives, quinazoline derivatives, quinoxaline derivatives, phthalazine derivatives, purine derivatives, pteridine derivatives, carbazole derivatives, phenanthridine derivatives, acridine derivatives, phenazine derivatives, 1,10-phenanthroline derivatives, adenine derivatives, adenosine derivatives, guanine derivatives, guanosine derivatives, uracil derivatives, and uridine derivatives.

Examples of suitable nitrogen-containing compounds having carboxyl group include aminobenzoic acid, indolecarboxylic acid, and amino acid derivatives (e.g. nicotinic acid, alanine, alginine, aspartic acid, glutamic acid, glycine, histidine, isoleucine, glycylleucine, leucine, methionine, phenylalanine, threonine, lysine, 3-aminopyrazine-2-carboxylic acid, and methoxyalanine). Examples of suitable nitrogen-containing compounds having sulfonyl group include 3-pyridinesulfonic acid and pyridinium p-toluenesulfonate. Examples of suitable nitrogen-containing compounds having hydroxyl group, nitrogen-containing compounds having hydroxyphenyl group, and alcoholic nitrogen-containing compounds include 2-hydroxypyridine, aminocresol, 2,4-quinolinediol, 3-indolemethanol hydrate, monoethanolamine, diethanolamine, triethanolamine, N-ethyldiethanolamine, N,N-diethylethanolamine, triisopropanolamine, 2,2'-iminodiethanol, 2-aminoethanol, 3-amino-1-propanol, 4-amino-1-butanol, 4-(2-hydroxyethyl)morpholine, 2-(2-hydroxyethyl)pyridine, 1-(2-hydroxyethyl)piperazine, 1-[2-(2-hydroxyethoxy)ethyl]piperazine, piperidine ethanol, 1-(2- hydroxyethyl)pyrrolidine, 1-(2-hydroxyethyl)-2-pyrrolidinone, 3-piperidino-1,2-propanediol, 3-pyrrolidino-1,2-propanediol, 8-hydroxyjulolidine, 3-quinuclidinol, 3-tropanol, 1-methyl-2-pyrrolidine ethanol, 1-aziridine ethanol, N-(2-hydroxyethyl)phthalimide, and N-(2-hydroxyethyl)isonicotinamide. Examples of suitable amide derivatives include formamide, N-methylformamide, N,N-dimethylformamide, acetamide, N-methylacetamide, N,N-dimethylacetamide, propionamide, benzamide, and 1-cyclohexylpyrrolidone. Suitable imide derivatives include phthalimide, succinimide, and maleimide. Suitable carbamate derivatives include N-t-butoxycarbonyl-N,N-dicyclohexylamine, N-t-butoxycarbonylbenzimidazole and oxazolidinone.

In addition, organic nitrogen-containing compounds of the following general formula (B)-1 may also be included alone or in admixture.

$$N(X)_n(Y)_{3-n} \quad (B)-1$$

In the formula, n is equal to 1, 2 or 3; side chain Y is independently hydrogen or a straight, branched or cyclic $C_1$-$C_{20}$ alkyl group which may contain an ether or hydroxyl group; and side chain X is independently selected from groups of the following general formulas (X)-1 to (X)-3, and two or three X's may bond together to form a ring.

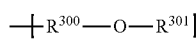

(X)-1

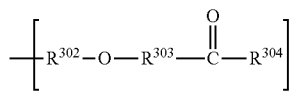

(X)-2

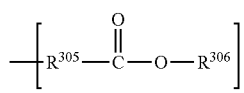

(X)-3

In the formulas, $R^{300}$, $R^{302}$ and $R^{305}$ are independently straight or branched $C_1$-$C_4$ alkylene groups; $R^{301}$ and $R^{304}$ are independently hydrogen, or straight, branched or cyclic $C_1$-$C_{20}$ alkyl groups which may contain at least one hydroxyl, ether, ester group or lactone ring; $R^{303}$ is a single bond or a straight or branched $C_1$-$C_4$ alkylene group; and $R^{306}$ is a straight, branched or cyclic $C_1$-$C_{20}$ alkyl group which may contain at least one hydroxyl, ether, ester group or lactone ring.

Illustrative examples of the compounds of formula (B)-1 include tris(2-methoxymethoxyethyl)amine, tris{2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, tris[2-{2-(2-hydroxyethoxy)ethoxy}ethyl]amine, 4,7,13,16,21,24-hexaoxa-1,10-diazabicyclo[8.8.8]hexacosane, 4,7,13,18-tetraoxa-1,10-diazabicyclo[8.5.5]eicosane, 1,4,10,13-tetraoxa-7,16-diazabicyclooctadecane, 1-aza-12-crown-4, 1-aza-15-crown-5, 1-aza-18-crown-6, tris(2-formyloxyethyl)amine, tris(2-acetoxyethyl)amine, tris(2-propionyloxyethyl)amine, tris(2-butyryloxyethyl)amine, tris(2-isobutyryloxyethyl)amine, tris(2-valeryloxyethyl)amine, tris(2-pivaloyloxyethyl)amine, N,N-bis(2-acetoxyethyl)-2-(acetoxyacetoxy)ethylamine, tris(2-methoxycarbonyloxyethyl)amine, tris(2-tert-butoxycarbonyloxyethyl)amine, tris[2-(2-oxopropoxy)ethyl]amine, tris[2-(methoxycarbonylmethyloxy)ethyl]amine, tris[2-(tert-butoxycarbonylmethyloxy)ethyl]amine, tris[2-(cyclohexyloxycarbonylmethyloxy)ethyl]amine, tris(2-methoxycarbonylethyl)amine, tris(2-ethoxycarbonylethyl)amine, N,N-bis(2-hydroxyethyl)-2-(methoxycarbonyl)ethylamine, N,N-bis(2-acetoxyethyl)-2-(methoxycarbonyl)ethylamine, N,N-bis(2-hydroxyethyl)-2-(ethoxycarbonyl)ethylamine, N,N-bis(2-acetoxyethyl)-2-(ethoxycarbonyl)ethylamine, N,N-bis(2-hydroxyethyl)-2-(2-methoxyethoxycarbonyl)ethylamine, N,N-bis(2-acetoxyethyl)-2-(2-methoxyethoxycarbonyl)ethylamine, N,N-bis(2-hydroxyethyl)-2-(2-hydroxyethoxycarbonyl)ethylamine, N,N-bis(2-acetoxyethyl)-2-(2-acetoxyethoxycarbonyl)ethylamine, N,N-bis(2-hydroxyethyl)-2-[(methoxycarbonyl)methoxycarbonyl]-ethylamine, N,N-bis(2-acetoxyethyl)-2-[(methoxycarbonyl)methoxycarbonyl]-ethylamine, N,N-bis(2-hydroxyethyl)-2-(2-oxopropoxycarbonyl)ethylamine, N,N-bis(2-acetoxyethyl)-2-(2-oxopropoxycarbonyl)ethylamine, N,N-bis(2-hydroxyethyl)-2-(tetrahydrofurfuryloxycarbonyl)-ethylamine, N,N-bis(2-acetoxyethyl)-2-(tetrahydrofurfuryloxycarbonyl)-ethylamine, N,N-bis(2-hydroxyethyl)-2-[(2-oxotetrahydrofuran-3-yl)oxy-carbonyl]ethylamine, N,N-bis(2-acetoxyethyl)-2-[(2-oxotetrahydrofuran-3-yl)oxy-carbonyl]ethylamine, N,N-bis(2-hydroxyethyl)-2-(4-hydroxybutoxycarbonyl)ethylamine, N,N-bis(2-formyloxyethyl)-2-(4-formyloxybutoxycarbonyl)-ethylamine, N,N-bis(2-formyloxyethyl)-2-(2-formyloxyethoxycarbonyl)-ethylamine, N,N-bis(2-methoxyethyl)-2-(methoxycarbonyl)ethylamine, N-(2-hydroxyethyl)-bis[2-(methoxycarbonyl)ethyl]amine, N-(2-acetoxyethyl)-bis[2-(methoxycarbonyl)ethyl]amine, N-(2-hydroxyethyl)-bis[2-(ethoxycarbonyl)ethyl]amine, N-(2-acetoxyethyl)-bis[2-(ethoxycarbonyl)ethyl]amine, N-(3-hydroxy-1-propyl)-bis[2-(methoxycarbonyl)ethyl]amine, N-(3-acetoxy-1-propyl)-bis[2-(methoxycarbonyl)ethyl]amine, N-(2-methoxyethyl)-bis[2-(methoxycarbonyl)ethyl]amine, N-butyl-bis[2-(methoxycarbonyl)ethyl]amine, N-butyl-bis[2-(2-methoxyethoxycarbonyl)ethyl]amine, N-methyl-bis(2-acetoxyethyl)amine, N-ethyl-bis(2-acetoxyethyl)amine, N-methyl-bis(2-pivaloyloxyethyl)amine, N-ethyl-bis[2-(methoxycarbonyloxy)ethyl]amine, N-ethyl-bis[2-(tert-butoxycarbonyloxy)ethyl]amine, tris(methoxycarbonylmethyl)amine, tris(ethoxycarbonylmethyl)amine, N-butyl-bis(methoxycarbonylmethyl)amine, N-hexyl-bis(methoxycarbonylmethyl)amine, and β-(diethylamino)-δ-valerolactone.

Also useful are one or more organic nitrogen-containing compounds having cyclic structure represented by the following general formula (B)-2.

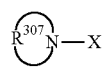

(B)-2

Herein X is as defined above, and $R^{307}$ is a straight or branched $C_2$-$C_{20}$ alkylene group which may contain one or more carbonyl, ether, ester or sulfide groups.

Illustrative examples of the organic nitrogen-containing compounds having formula (B)-2 include 1-[2-(methoxymethoxy)ethyl]pyrrolidine, 1-[2-(methoxymethoxy)ethyl]piperidine, 4-[2-(methoxymethoxy)ethyl]morpholine, 1-[2-[(2-methoxyethoxy)methoxy]ethyl]pyrrolidine, 1-[2-[(2-methoxyethoxy)methoxy]ethyl]piperidine, 4-[2-[(2-methoxyethoxy)methoxy]ethyl]morpholine, 2-(1-pyrrolidinyl)ethyl acetate, 2-piperidinoethyl acetate, 2-morpholinoethyl acetate, 2-(1-pyrrolidinyl)ethyl formate, 2-piperidinoethyl propionate, 2-morpholinoethyl acetoxyacetate, 2-(1-pyrrolidinyl)ethyl methoxyacetate, 4-[2-(methoxycarbonyloxy)ethyl]morpholine, 1-[2-(t-butoxycarbonyloxy)ethyl]piperidine, 4-[2-(2-methoxyethoxycarbonyloxy)ethyl]morpholine, methyl 3-(1-pyrrolidinyl)propionate, methyl 3-piperidinopropionate, methyl 3-morpholinopropionate, methyl 3-(thiomorpholino)propionate, methyl 2-methyl-3-(1-pyrrolidinyl)propionate, ethyl 3-morpholinopropionate, methoxycarbonylmethyl 3-piperidinopropionate, 2-hydroxyethyl 3-(1-pyrrolidinyl)propionate, 2-acetoxyethyl 3-morpholinopropionate, 2-oxotetrahydrofuran-3-yl 3-(1-pyrrolidinyl)propionate, tetrahydrofurfuryl 3-morpholinopropionate, glycidyl 3-piperidinopropionate, 2-methoxyethyl 3-morpholinopropionate, 2-(2-methoxyethoxy)ethyl 3-(1-pyrrolidinyl)propionate, butyl 3-morpholinopropionate, cyclohexyl 3-piperidinopropionate, α-(1-pyrrolidinyl)methyl-γ-butyrolactone, β-piperidino-γ-butyrolactone, β-morpholino-δ-valerolactone, methyl 1-pyrrolidinylacetate, methyl piperidinoacetate, methyl morpholinoacetate, methyl thiomorpholinoacetate, ethyl 1-pyrrolidinylacetate, 2-methoxyethyl morpholinoacetate, 2-morpholinoethyl 2-methoxyacetate, 2-morpholinoethyl 2-(2-methoxyethoxy)acetate, 2-morpholinoethyl 2-[2-(2-methoxyethoxy)ethoxy]acetate, 2-morpholinoethyl hexanoate, 2-morpholinoethyl octanoate, 2-morpholinoethyl decanoate, 2-morpholinoethyl laurate, 2-morpholinoethyl myristate, 2-morpholinoethyl palmitate, and 2-morpholinoethyl stearate.

Also, one or more organic nitrogen-containing compounds having cyano group represented by the following general formulae (B)-3 to (B)-6 may be blended.

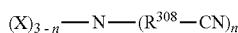  (B)-3

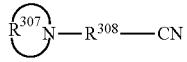  (B)-4

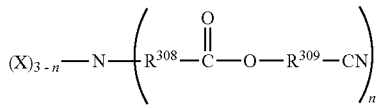  (B)-5

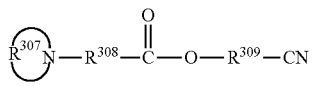  (B)-6

Herein, X, $R^{307}$ and n are as defined above, and $R^{308}$ and $R^{309}$ are each independently a straight or branched $C_1$-$C_4$ alkylene group.

Illustrative examples of the organic nitrogen-containing compounds having cyano represented by formulae (B)-3 to (B)-6 include 3-(diethylamino)propiononitrile, N,N-bis(2-hydroxyethyl)-3-aminopropiononitrile, N,N-bis(2-acetoxyethyl)-3-aminopropiononitrile, N,N-bis(2-formyloxyethyl)-3-aminopropiononitrile, N,N-bis(2-methoxyethyl)-3-aminopropiononitrile, N,N-bis[2-(methoxymethoxy)ethyl]-3-aminopropiononitrile, methyl N-(2-cyanoethyl)-N-(2-methoxyethyl)-3-aminopropionate, methyl N-(2-cyanoethyl)-N-(2-hydroxyethyl)-3-aminopropionate, methyl N-(2-acetoxyethyl)-N-(2-cyanoethyl)-3-aminopropionate, N-(2-cyanoethyl)-N-ethyl-3-aminopropiononitrile, N-(2-cyanoethyl)-N-(2-hydroxyethyl)-3-aminopropiononitrile, N-(2-acetoxyethyl)-N-(2-cyanoethyl)-3-aminopropiononitrile, N-(2-cyanoethyl)-N-(2-formyloxyethyl)-3-aminopropiononitrile, N-(2-cyanoethyl)-N-(2-methoxyethyl)-3-aminopropiononitrile, N-(2-cyanoethyl)-N-[2-(methoxymethoxy)ethyl]-3-aminopropiononitrile, N-(2-cyanoethyl)-N-(3-hydroxy-1-propyl)-3-aminopropiononitrile, N-(3-acetoxy-1-propyl)-N-(2-cyanoethyl)-3-aminopropiononitrile, N-(2-cyanoethyl)-N-(3-formyloxy-1-propyl)-3-aminopropiononitrile, N-(2-cyanoethyl)-N-tetrahydrofurfuryl-3-aminopropiononitrile, N,N-bis(2-cyanoethyl)-3-aminopropiononitrile, diethylaminoacetonitrile, N,N-bis(2-hydroxyethyl)aminoacetonitrile, N,N-bis(2-acetoxyethyl)aminoacetonitrile, N,N-bis(2-formyloxyethyl)aminoacetonitrile, N,N-bis(2-methoxyethyl)aminoacetonitrile, N,N-bis[2-(methoxymethoxy)ethyl]aminoacetonitrile, methyl N-cyanomethyl-N-(2-methoxyethyl)-3-aminopropionate, methyl N-cyanomethyl-N-(2-hydroxyethyl)-3-aminopropionate, methyl N-(2-acetoxyethyl)-N-cyanomethyl-3-aminopropionate, N-cyanomethyl-N-(2-hydroxyethyl)aminoacetonitrile, N-(2-acetoxyethyl)-N-(cyanomethyl)aminoacetonitrile, N-cyanomethyl-N-(2-formyloxyethyl)aminoacetonitrile, N-cyanomethyl-N-(2-methoxyethyl)aminoacetonitrile, N-cyanomethyl-N-[2-(methoxymethoxy)ethyl)aminoacetonitrile, N-cyanomethyl-N-(3-hydroxy-1-propyl)aminoacetonitrile, N-(3-acetoxy-1-propyl)-N-(cyanomethyl)aminoacetonitrile, N-cyanomethyl-N-(3-formyloxy-1-propyl)aminoacetonitrile, N,N-bis(cyanomethyl)aminoacetonitrile, 1-pyrrolidinepropiononitrile, 1-piperidinepropiononitrile, 4-morpholinepropiononitrile, 1-pyrrolidineacetonitrile, 1-piperidineacetonitrile, 4-morpholineacetonitrile, cyanomethyl 3-diethylaminopropionate, cyanomethyl N,N-bis(2-hydroxyethyl)-3-aminopropionate, cyanomethyl N,N-bis(2-acetoxyethyl)-3-aminopropionate, cyanomethyl N,N-bis(2-formyloxyethyl)-3-aminopropionate, cyanomethyl N,N-bis(2-methoxyethyl)-3-aminopropionate, cyanomethyl N,N-bis[2-(methoxymethoxy)ethyl]-3-aminopropionate, 2-cyanoethyl 3-diethylaminopropionate, 2-cyanoethyl N,N-bis(2-hydroxyethyl)-3-aminopropionate, 2-cyanoethyl N,N-bis(2-acetoxyethyl)-3-aminopropionate, 2-cyanoethyl N,N-bis(2-formyloxyethyl)-3-aminopropionate, 2-cyanoethyl N,N-bis(2-methoxyethyl)-3-aminopropionate, 2-cyanoethyl N,N-bis[2-(methoxymethoxy)ethyl]-3-aminopropionate, cyanomethyl 1-pyrrolidinepropionate, cyanomethyl 1-piperidinepropionate, cyanomethyl 4-morpholinepropionate, 2-cyanoethyl 1-pyrrolidinepropionate, 2-cyanoethyl 1-piperidinepropionate, and 2-cyanoethyl 4-morpholinepropionate.

Also included are organic nitrogen-containing compounds having an imidazole structure and a polar functional group, represented by the general formula (B)-7.

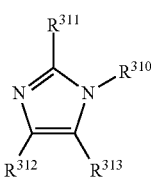  (B)-7

Herein, $R^{310}$ is a straight, branched or cyclic $C_2$-$C_{20}$ alkyl group bearing at least one polar functional group selected from among hydroxyl, carbonyl, ester, ether, sulfide, carbonate, cyano and acetal groups; $R^{311}$, $R^{312}$ and $R^{313}$ are each independently a hydrogen atom, a straight, branched or cyclic $C_1$-$C_{10}$ alkyl group, aryl group or aralkyl group.

Also included are organic nitrogen-containing compounds having a benzimidazole structure and a polar functional group, represented by the general formula (B)-8.

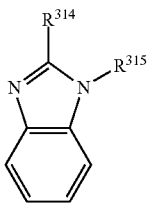
(B)-8

Herein, $R^{314}$ is a hydrogen atom, a straight, branched or cyclic $C_1$-$C_{10}$ alkyl group, aryl group or aralkyl group. $R^{315}$ is a polar functional group-bearing, straight, branched or cyclic $C_1$-$C_{20}$ alkyl group, and the alkyl group contains as the polar functional group at least one group selected from among ester, acetal and cyano groups, and may additionally contain at least one group selected from among hydroxyl, carbonyl, ether, sulfide and carbonate groups.

Further included are heterocyclic nitrogen-containing compounds having a polar functional group, represented by the general formulae (B)-9 and (B)-10.

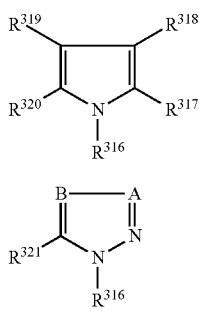
(B)-9

(B)-10

Herein, A is a nitrogen atom or $=$C—$R^{322}$, B is a nitrogen atom or $=$C—$R^{323}$, $R^{316}$ is a straight, branched or cyclic $C_2$-$C_{20}$ alkyl group bearing at least one polar functional group selected from among hydroxyl, carbonyl, ester, ether, sulfide, carbonate, cyano and acetal groups; $R^{317}$, $R^{318}$, $R^{319}$ and $R^{320}$ are each independently a hydrogen atom, a straight, branched or cyclic $C_1$-$C_{10}$ alkyl group or aryl group, or a pair of $R^{317}$ and $R^{318}$ and a pair of $R^{319}$ and $R^{320}$, taken together, may form a benzene, naphthalene or pyridine ring; $R^{321}$ is a hydrogen atom, a straight, branched or cyclic $C_1$-$C_{10}$ alkyl group or aryl group; $R^{322}$ and $R^{323}$ each are a hydrogen atom, a straight, branched or cyclic $C_1$-$C_{10}$ alkyl group or aryl group, or a pair of $R^{321}$ and $R^{323}$, taken together, may form a benzene or naphthalene ring.

Also included are organic nitrogen-containing compounds of aromatic carboxylic ester structure having the general formulae (B)-11 to (B)-14.

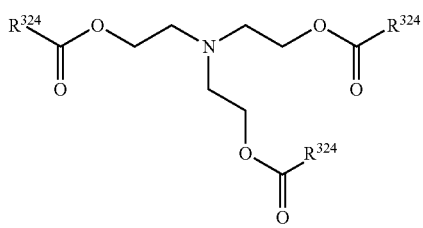
(B)-11

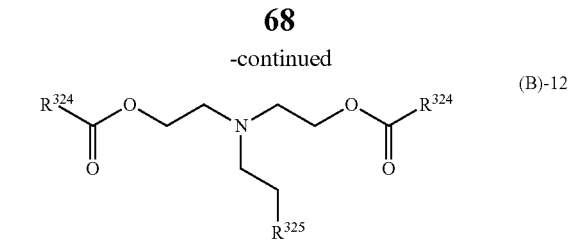
(B)-12

(B)-13

(B)-14

Herein $R^{324}$ is a $C_6$-$C_{20}$ aryl group or $C_4$-$C_{20}$ hetero-aromatic group, in which some or all of hydrogen atoms may be replaced by halogen atoms, straight, branched or cyclic $C_1$-$C_{20}$ alkyl groups, $C_6$-$C_{20}$ aryl groups, $C_7$-$C_{20}$ aralkyl groups, $C_1$-$C_{10}$ alkoxy groups, $C_1$-$C_{10}$ acyloxy groups or $C_1$-$C_{10}$ alkylthio groups. $R^{325}$ is $CO_2R^{326}$, $OR^{327}$ or cyano group. $R^{326}$ is a $C_1$-$C_{10}$ alkyl group, in which some methylene groups may be replaced by oxygen atoms. $R^{327}$ is a $C_1$-$C_{10}$ alkyl or acyl group, in which some methylene groups may be replaced by oxygen atoms. $R^{328}$ is a single bond, methylene, ethylene, sulfur atom or —O($CH_2CH_2O$)$_n$— group wherein n is 0, 1, 2, 3 or 4. $R^{329}$ is hydrogen, methyl, ethyl or phenyl. X is a nitrogen atom or $CR^{330}$. Y is a nitrogen atom or $CR^{331}$. Z is a nitrogen atom or $CR^{332}$. $R^{330}$, $R^{331}$ and $R^{332}$ are each independently hydrogen, methyl or phenyl. Alternatively, a pair of $R^{330}$ and $R^{331}$ or a pair of $R^{331}$ and $R^{332}$ may bond together to form a $C_6$-$C_{20}$ aromatic ring or $C_2$-$C_{20}$ hetero-aromatic ring.

Further included are organic nitrogen-containing compounds of 7-oxanorbornane-2-carboxylic ester structure having the general formula (B)-15.

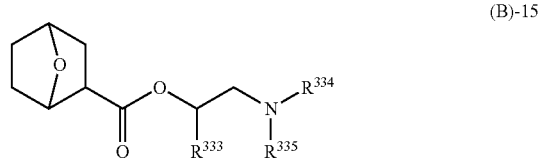
(B)-15

Herein $R^{333}$ is hydrogen or a straight, branched or cyclic $C_1$-$C_{10}$ alkyl group. $R^{334}$ and $R^{335}$ are each independently a $C_1$-$C_{20}$ alkyl group, $C_6$-$C_{20}$ aryl group or $C_7$-$C_{20}$ aralkyl group, which may contain one or more polar functional groups selected from among ether, carbonyl, ester, alcohol, sulfide, nitrile, amine, imine, and amide and in which some hydrogen atoms may be replaced by halogen atoms. $R^{334}$ and $R^{335}$, taken together, may form a heterocyclic or hetero-aromatic ring of 2 to 20 carbon atoms.

The organic nitrogen-containing compounds may be used alone or in admixture of two or more. The organic nitrogen-containing compound is preferably formulated in an amount of 0.001 to 2 parts, and especially 0.01 to 1 part by weight, per 100 parts by weight of the base resin. Less than 0.001 part of the nitrogen-containing compound achieves no or little addition effect whereas more than 2 parts would result in too low a sensitivity.

Other Components

The resist composition of the invention may include optional ingredients, for example, a surfactant which is commonly used for improving the coating characteristics. Optional ingredients may be added in conventional amounts so long as this does not compromise the objects of the invention.

Nonionic surfactants are preferred, examples of which include perfluoroalkylpolyoxyethylene ethanols, fluorinated alkyl esters, perfluoroalkylamine oxides, perfluoroalkyl EO-addition products, and fluorinated organosiloxane compounds. Useful surfactants are commercially available under the trade names Fluorad FC-430 and FC-431 from Sumitomo 3M, Ltd., Surflon S-141, S-145, KH-10, KH-20, KH-30 and KH-40 from Asahi Glass Co., Ltd., Unidyne DS-401, DS-403 and DS-451 from Daikin Industry Co., Ltd., Megaface F-8151 from Dai-Nippon Ink & Chemicals, Inc., and X-70-092 and X-70-093 from Shin-Etsu Chemical Co., Ltd. Preferred surfactants are Fluorad FC-430 from Sumitomo 3M, Ltd., KH-20 and KH-30 from Asahi Glass Co., Ltd., and X-70-093 from Shin-Etsu Chemical Co., Ltd.

To the resist composition of the invention, other components such as dissolution regulators, carboxylic acid compounds and acetylene alcohol derivatives may be added if necessary. Optional components may be added in conventional amounts so long as this does not compromise the objects of the invention.

The dissolution regulator which can be added to the resist composition is a compound having on the molecule at least two phenolic hydroxyl groups, in which an average of from 0 to 100 mol % of all the hydrogen atoms on the phenolic hydroxyl groups are replaced by acid labile groups or a compound having on the molecule at least one carboxyl group, in which an average of 50 to 100 mol % of all the hydrogen atoms on the carboxyl groups are replaced by acid labile groups, both the compounds having an average molecular weight within a range of 100 to 1,000, and preferably 150 to 800.

The degree of substitution of the hydrogen atoms on the phenolic hydroxyl groups with acid labile groups is on average at least 0 mol %, and preferably at least 30 mol %, of all the phenolic hydroxyl groups. The upper limit is 100 mol %, and preferably 80 mol %. The degree of substitution of the hydrogen atoms on the carboxyl groups with acid labile groups is on average at least 50 mol %, and preferably at least 70 mol %, of all the carboxyl groups, with the upper limit being 100 mol %.

Preferable examples of such compounds having two or more phenolic hydroxyl groups or compounds having a carboxyl group include those of formulas (D1) to (D14) below.

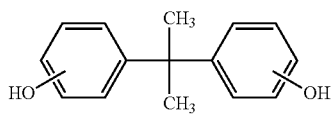
(D1)

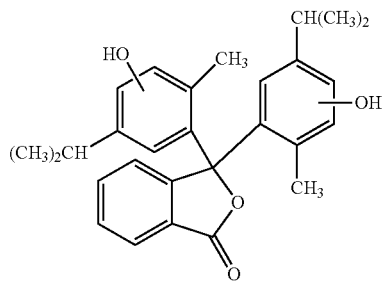
(D2)

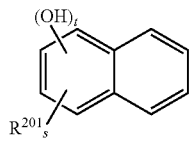
(D3)

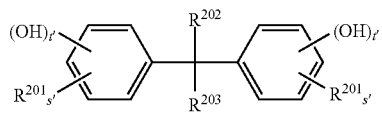
(D4)

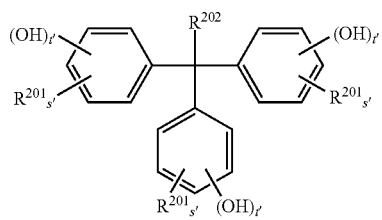
(D5)

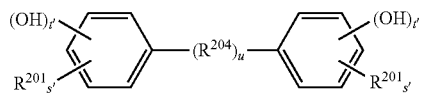
(D6)

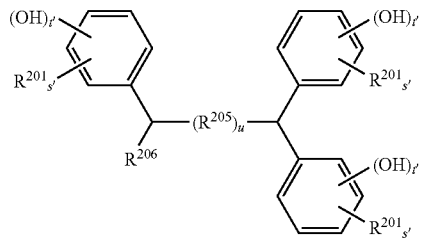
(D7)

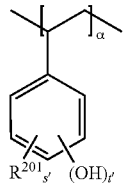
(D8)

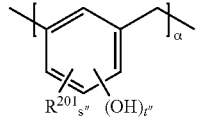
(D9)

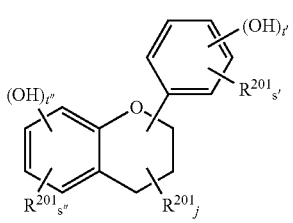

(D10)

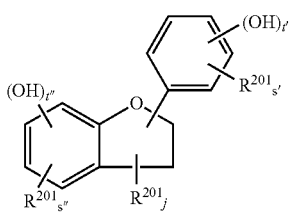

(D11)

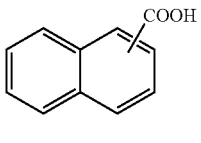

(D12)

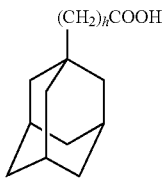

(D13)

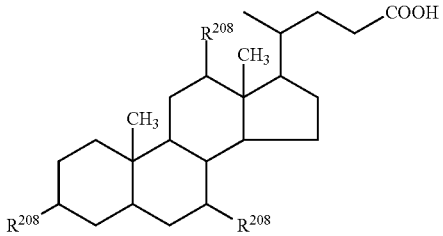

(D14)

In these formulas, $R^{201}$ and $R^{202}$ are each hydrogen or a straight or branched $C_1$-$C_8$ alkyl or alkenyl group, for example, hydrogen, methyl, ethyl, butyl, propyl, ethynyl and cyclohexyl.

$R^{203}$ is hydrogen, a straight or branched $C_1$-$C_8$ alkyl or alkenyl group, or —$(R^{207})_h$—COOH wherein $R^{207}$ is a straight or branched $C_1$-$C_{10}$ alkylene, for example, those exemplified for $R^{201}$ and $R^{202}$ and —COOH and —CH$_2$COOH.

$R^{204}$ is —(CH$_2$)$_i$— wherein i=2 to 10, $C_6$-$C_{10}$ arylene, carbonyl, sulfonyl, an oxygen atom, or a sulfur atom, for example, ethylene, phenylene, carbonyl, sulfonyl, oxygen atom or sulfur atom.

$R^{205}$ is a $C_1$-$C_{10}$ alkylene, a $C_6$-$C_{10}$ arylene, carbonyl, sulfonyl, an oxygen atom, or a sulfur atom, for example, methylene and those exemplified for $R^{204}$.

$R^{206}$ is hydrogen, a straight or branched $C_1$-$C_8$ alkyl or alkenyl, or a phenyl or naphthyl group in which at least one hydrogen atom is substituted by a hydroxyl group, for example, hydrogen, methyl, ethyl, butyl, propyl, ethynyl, cyclohexyl, hydroxyl-substituted phenyl, and hydroxyl-substituted naphthyl.

$R^{208}$ is hydrogen or hydroxyl.

The letter j is an integer from 0 to 5; u and h are each 0 or 1; s, t, s', t', s", and t" are each numbers which satisfy s+t=8, s'+t'=5, and s'+t'=4, and are such that each phenyl skeleton has at least one hydroxyl group; and α is a number such that the compounds of formula (D8) or (D9) have a weight average molecular weight of from 100 to 1,000.

Exemplary acid labile groups on the dissolution regulator include a variety of such groups, typically groups of the general formulae (L1) to (L4), tertiary $C_4$-$C_{20}$ alkyl groups, trialkylsilyl groups in which each of the alkyls has 1 to 6 carbon atoms, and $C_4$-$C_{20}$ oxoalkyl groups. Examples of the respective groups are as previously described.

The dissolution regulator may be formulated in an amount of 0 to 50 parts, preferably 0 to 40 parts, and more preferably 0 to 30 parts by weight, per 100 parts by weight of the base resin, and may be used singly or as a mixture of two or more thereof. The use of more than 50 parts of the dissolution regulator would lead to slimming of the patterned film, and thus a decline in resolution.

The dissolution regulator can be synthesized by introducing acid labile groups into a compound having phenolic hydroxyl or carboxyl groups in accordance with an organic chemical formulation.

In the resist composition, a carboxylic acid compound may be blended. The carboxylic acid compound used herein may be one or more compounds selected from Groups I and II below, but is not limited thereto. Including this compound improves the PED stability of the resist and ameliorates edge roughness on nitride film substrates.

Group I:

Compounds in which some or all of the hydrogen atoms on the phenolic hydroxyl groups of the compounds of general formulas (A1) to (A10) below are replaced by —$R^{401}$—COOH (wherein $R^{401}$ is a straight or branched $C_1$-$C_{10}$ alkylene group), and in which the molar ratio C/(C+D) of phenolic hydroxyl groups (C) to ≡C—COOH groups (D) in the molecule is from 0.1 to 1.0.

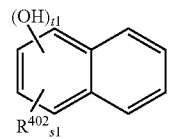

(A1)

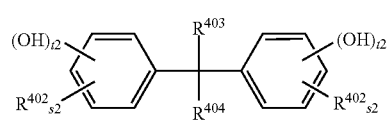

(A2)

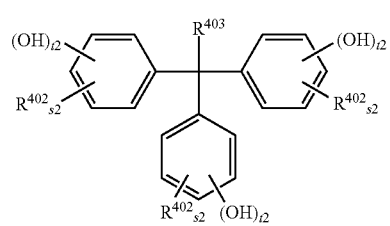

(A3)

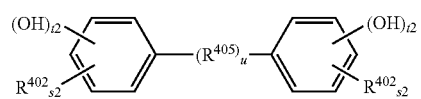

(A4)

-continued

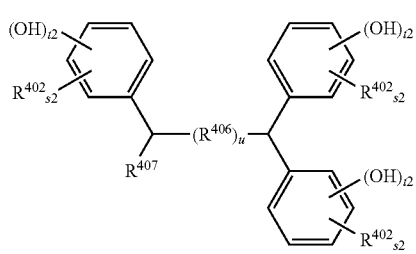
(A5)

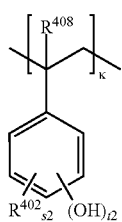
(A6)

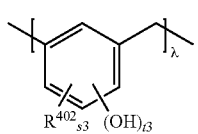
(A7)

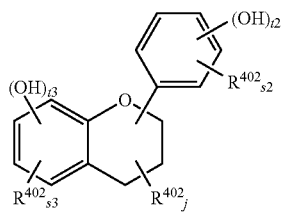
(A8)

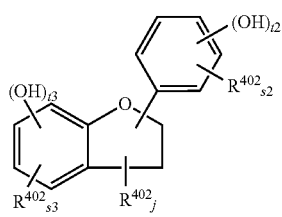
(A9)

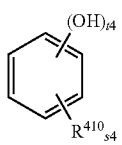
(A10)

In these formulas, $R^{402}$ and $R^{403}$ are each hydrogen or a straight or branched $C_1$-$C_8$ alkyl or alkenyl; $R^{404}$ is hydrogen, a straight or branched $C_1$-$C_8$ alkyl or alkenyl, or a $-(R^{409})_h-$COOR' group (R' being hydrogen or $-R^{409}-$COOH); $R^{405}$ is $-(CH_2)_i-$ (wherein i is 2 to 10), a $C_6$-$C_{10}$ arylene, carbonyl, sulfonyl, an oxygen atom, or a sulfur atom; $R^{406}$ is a $C_1$-$C_{10}$ alkylene, a $C_6$-$C_{10}$ arylene, carbonyl, sulfonyl, an oxygen atom, or a sulfur atom; $R^{407}$ is hydrogen, a straight or branched $C_1$-$C_8$ alkyl or alkenyl, or a hydroxyl-substituted phenyl or naphthyl; $R^{408}$ is hydrogen or methyl; $R^{409}$ is a straight or branched $C_1$-$C_{10}$ alkylene; $R^{410}$ is hydrogen, a straight or branched $C_1$-$C_8$ alkyl or alkenyl, or a $-R^{411}-$COOH group; $R^{411}$ is a straight or branched $C_1$-$C_{10}$ alkylene; the letter j is a number from 0 to 3; u is a number from 1 to 4; h is a number from 0 to 4; s1, t1, s2, t2, s3, t3, s4, and t4 are each numbers which satisfy s1+t1=8, s2+t2=5, s3+t3=4, and s4+t4=6, and are such that each phenyl structure has at least one hydroxyl group; κ is a number such that the compound of formula (A6) may have a weight average molecular weight of 1,000 to 5,000; and λ is a number such that the compound of formula (A7) may have a weight average molecular weight of 1,000 to 10,000.

Group II:

Compounds of general formulas (A11) to (A15) below.

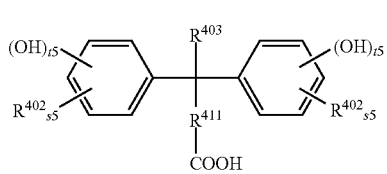
(A11)

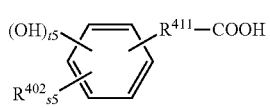
(A12)

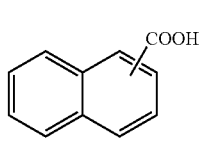
(A13)

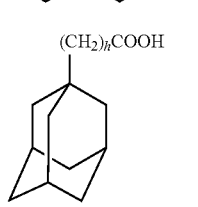
(A14)

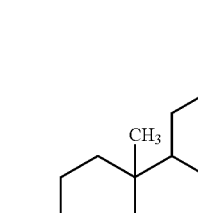
(A15)

In these formulas, $R^{402}$, $R^{403}$, and $R^{411}$ are as defined above; $R^{412}$ is hydrogen or hydroxyl; s5 and t5 are numbers which satisfy s5≧0, t5≧0, and s5+t5=5; and h is a number from 0 to 4.

Illustrative, non-limiting examples of the compound having a carboxyl group include compounds of the general formulas AI-1 to AI-14 and AII-1 to AII-10 below.

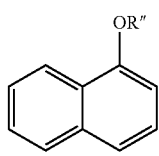
(AI-1)

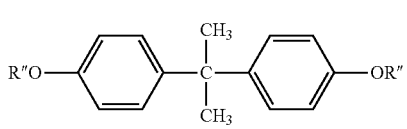
(AI-2)

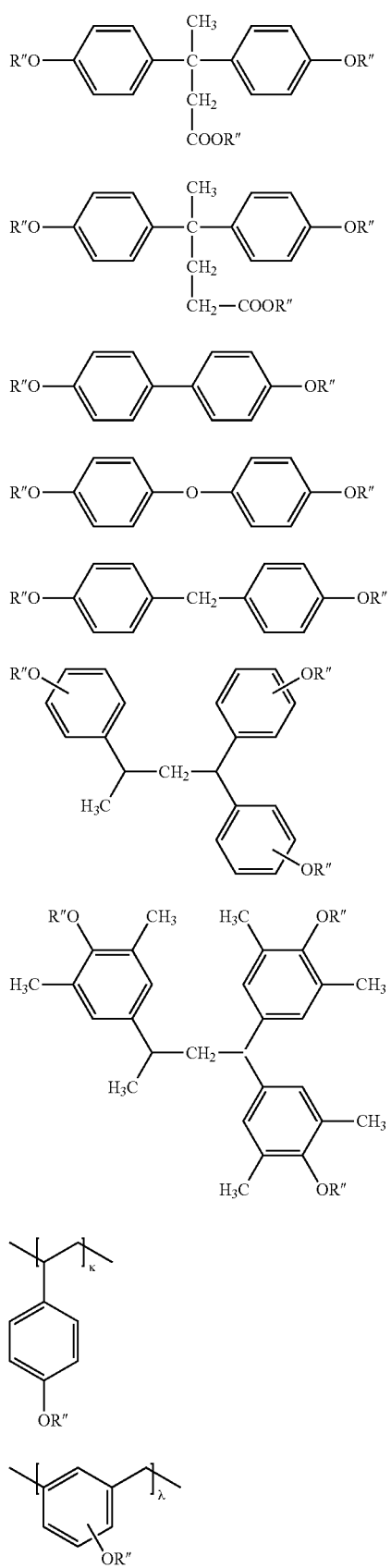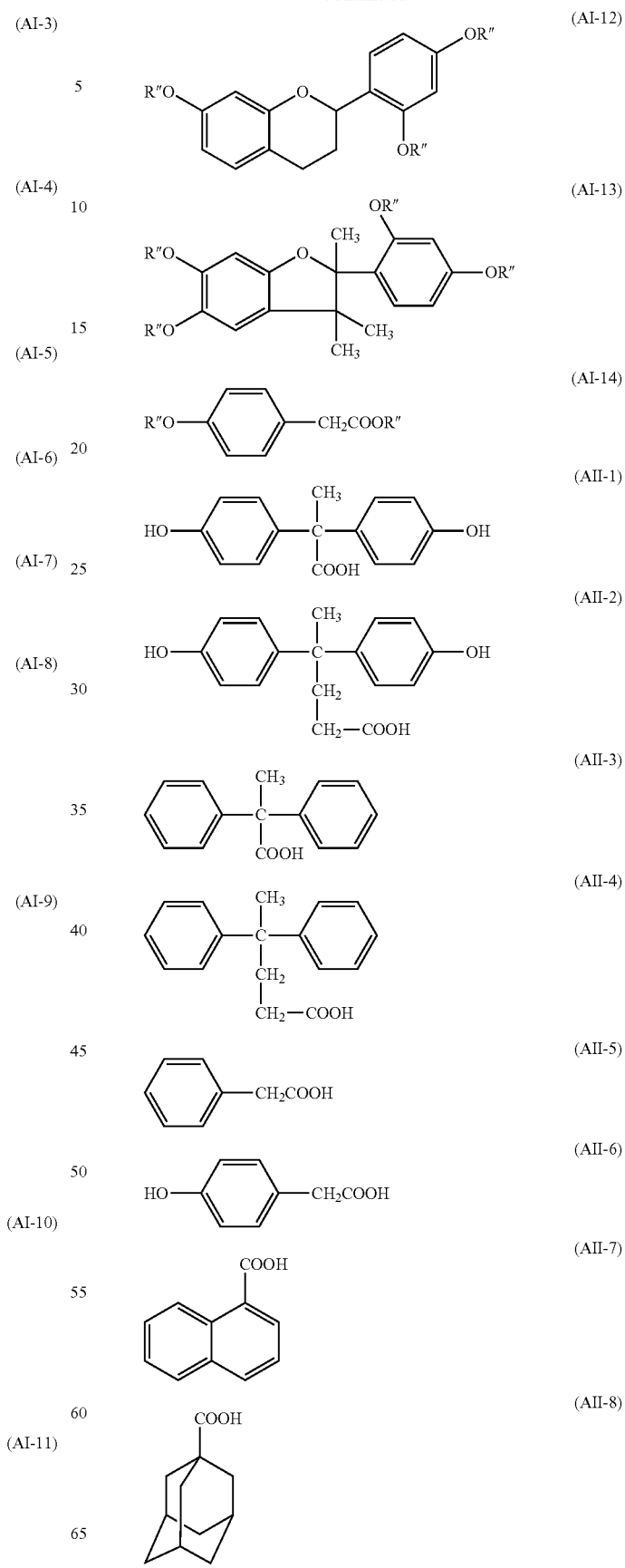

-continued

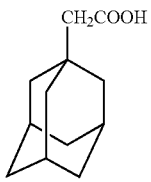
(AII-9)

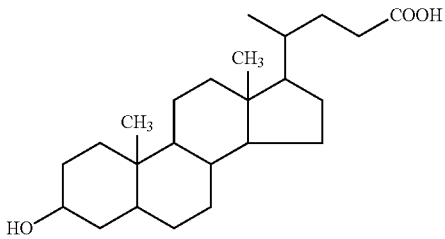
(AII-10)

In the above formulas, R" is hydrogen or a —CH$_2$COOH group such that the —CH$_2$COOH group accounts for 10 to 100 mol % of R" in each compound, κ and λ are as defined above.

The compound having a =C—COOH group may be used singly or as combinations of two or more thereof. The compound having a =C—COOH group is added in an amount ranging from 0 to 5 parts, preferably 0.1 to 5 parts, more preferably 0.1 to 3 parts, further preferably 0.1 to 2 parts by weight, per 100 parts by weight of the base resin. More than 5 parts of the compound can reduce the resolution of the resist composition.

Preferred examples of the acetylene alcohol derivative which can be added to the resist composition include those having the general formula (S1) or (S2) below.

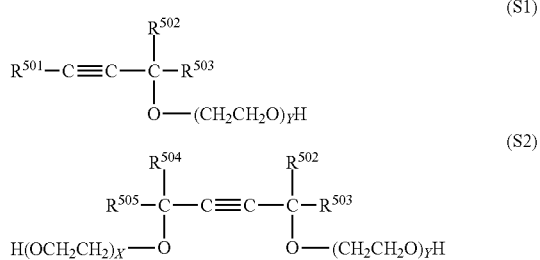

In the formulas, R$^{501}$, R$^{502}$, R$^{503}$, R$^{504}$, and R$^{505}$ are each hydrogen or a straight, branched or cyclic C$_1$-C$_8$ alkyl; and X and Y are each 0 or a positive number, satisfying $0 \leq X \leq 30$, $0 \leq Y \leq 30$, and $0 \leq X+Y \leq 40$.

Preferable examples of the acetylene alcohol derivative include Surfynol 61, Surfynol 82, Surfynol 104, Surfynol 104E, Surfynol 104H, Surfynol 104A, Surfynol TG, Surfynol PC, Surfynol 440, Surfynol 465, and Surfynol 485 from Air Products and Chemicals Inc., and Surfynol E1004 from Nisshin Chemical Industries Ltd.

The acetylene alcohol derivative is preferably added in an amount of 0 to 2 parts, more preferably 0.01 to 2 parts, and even more preferably 0.02 to 1 part by weight per 100 parts by weight of the base resin in the resist composition. More than 2 parts by weight would result in a resist having a low resolution.

Pattern formation using the resist composition of the invention may be carried out by a known lithographic technique. For example, the resist composition is applied onto a substrate such as a silicon wafer by spin coating or the like to form a resist film having a thickness of 0.05 to 2.0 μm, which is then pre-baked on a hot plate at 60 to 150° C. for 0.1 to 10 minutes, and preferably at 80 to 140° C. for 0.5 to 5 minutes. A patterning mask having the desired pattern is then placed over the resist film, and the film exposed through the mask to an electron beam or to high-energy radiation such as deep-UV, excimer laser, or x-ray in a dose of about 1 to 200 mJ/cm$^2$, and preferably about 10 to 100 mJ/cm$^2$. Light exposure may be done by a conventional exposure process or in some cases, by an immersion process of providing liquid (typically water) impregnation between the lens and the resist. The resist film is then post-exposure baked (PEB) on a hot plate at 60 to 150° C. for 0.1 to 5 minutes, and preferably at 80 to 140° C. for 0.5 to 3 minutes. Finally, development is carried out using as the developer an aqueous alkali solution, such as a 0.1 to 5 wt % (preferably 2 to 3 wt %) aqueous solution of tetramethylammonium hydroxide (TMAH), this being done by a conventional method such as dip, puddle or spray development for a period of 0.1 to 3 minutes, and preferably 0.5 to 2 minutes. These steps result in the formation of the desired pattern on the substrate. Of the various types of high-energy radiation that may be used, the resist composition of the invention is best suited to fine pattern formation with, in particular, deep-UV rays having a wavelength of 260 to 120 nm, excimer lasers, x-rays, or electron beams. The desired pattern may not be obtainable outside the upper and lower limits of the above range.

EXAMPLE

Synthesis Examples, Examples and Comparative Examples are given below by way of illustration and not by way of limitation. Mw is weight average molecular weight.

Monomer Synthesis Examples

Ester compounds were synthesized in accordance with the following formulation.

Monomer Synthesis Example 1

Synthesis of 2-methyl-4-oxatricyclo[5.2.1.0$^{2,6}$]decan-3-yl methacrylate

Monomer Synthesis Example 1-1

Synthesis of 2-methyl-4-oxatricyclo[5.2.1.0$^{2,6}$]decan-3-yl acetate

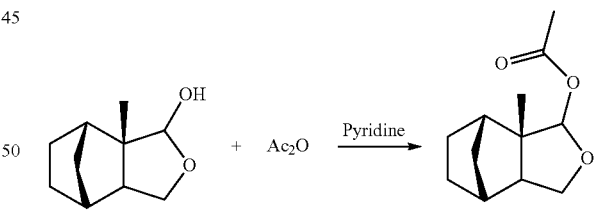

A mixture of 63 g of 2-methyl-4-oxatricyclo[5.2.1.0$^{2,6}$] decan-3-ol, 42 g of pyridine, and 51 g of acetic anhydride was heated at 50° C. for 5 hours. The reaction mixture was concentrated. The concentrate was purified by distillation, obtaining 74 g (yield 96%) of the target compound.

2-methyl-4-oxatricyclo[5.2.1.0$^{2,6}$]decan-3-yl acetate

Colorless liquid
  Boiling point: 84° C./40 Pa
  GC-MS (EI): (m/z)$^+$=29, 43, 55, 67, 79, 93, 107, 122, 151, 167, 209 [(M-H)$^+$]
  IR (thin film): ν=2966, 2879, 1739, 1479, 1463, 1375, 1241, 1222, 1195, 1116, 1083, 1035, 1004, 973, 952, 925, 908 cm$^{-1}$ $^1$H-NMR (600 MHz in CDCl$_3$): δ=1.03 (3H, s), 1.24-1.36 (3H, m), 1.44 (1H, m), 1.52 (1H, m), 1.70 (1H, m), 2.00 (2H, m), 2.02 (3H, s), 2.20 (1H, m), 3.83 (1H, dd, J=27.1, 9.3 Hz), 3.84 (1H, dd, J=32.6, 9.3 Hz), 6.14 (1H, s) ppm $^{13}$C-NMR (150 MHz in CDCl$_3$): δ=21.22, 21.51, 21.97, 23.33, 40.35, 41.19, 47.02, 51.70, 54.14, 68.33, 100.6, 170.5 ppm Monomer Synthesis Example 1-2

Synthesis of 2-methyl-4-oxatricyclo[5.2.1.0$^{2,6}$]decan-3-yl methacrylate

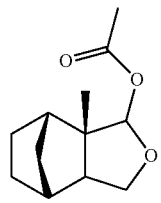

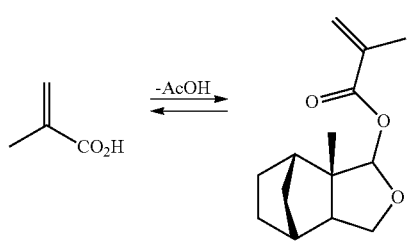

A mixture of 73 g of 2-methyl-4-oxatricyclo[5.2.1.0$^{2,6}$]decan-3-yl acetate, 150 g of methacrylic acid, and 40 mg of 2,2'-methylenebis(6-t-butyl-p-cresol) was heated at 50° C. under atmospheric pressure for 30 minutes, after which under a reduced pressure of 0.20 kPa, the reaction mixture was heated for 18 hours for distilling off the acetic acid formed. The reaction mixture was purified by distillation, obtaining 72 g (yield 91%) of the target compound.

2-methyl-4-oxatricyclo[5.2.1.0$^{2,6}$]decan-3-yl methacrylate

Colorless liquid

Boiling point: 91° C./13 Pa

GC-MS (EI): (m/z)$^+$=29, 41, 55, 67, 79, 93, 107, 121, 133, 151, 167, 235 [(M-H)$^+$]

IR (thin film): ν=2964, 2879, 1722, 1637, 1461, 1380, 1321, 1295, 1170, 1157, 1112, 1079, 1006, 971, 954, 939, 917 cm$^{-1}$ $^1$H-NMR (600 MHz in CDCl$_3$): δ=1.07 (3H, s), 1.23-1.37 (3H, m), 1.56 (1H, m), 1.47 (1H, m), 1.72 (1H, m), 1.91 (3H, m), 2.03 (2H, m), 2.22 (1H, m), 3.85 (1H, dd, J=28.4, 9.6 Hz), 3.86 (1H, dd, J=33.7, 9.6 Hz), 5.54 (1H, m), 6.08 (1H, m), 6.20 (1H, s) ppm $^{13}$C-NMR (150 MHz in CDCl$_3$): δ=18.32, 21.85, 22.13, 23.52, 40.50, 41.35, 47.17, 51.97, 54.58, 68.45, 100.9, 125.7, 136.8, 166.7 ppm Monomer Synthesis Example 2

Synthesis of 4-oxatricyclo[5.2.1.0$^{2,6}$]decan-3-yl methacrylate

The target compound, 4-oxatricyclo[5.2.1.0$^{2,6}$]decan-3-yl methacrylate was synthesized by following the same procedure as in Monomer Synthesis Example 1 aside from using an equimolar amount of 4-oxatricyclo[5.2.1.0$^{2,6}$]decan-3-ol instead of 2-methyl-4-oxatricyclo[5.2.1.0$^{2,6}$]decan-3-ol.

4-oxatricyclo[5.2.1.0$^{2,6}$]decan-3-yl methacrylate

Colorless liquid

Boiling point: 81° C./11 Pa

IR (thin film): ν=2956, 2879, 1722, 1637, 1475, 1452, 1403, 1380, 1363, 1326, 1311, 1297, 1267, 1211, 1153, 1116, 1101, 1049, 1020, 1002, 950, 933, 912, 900, 825, 813, 800 cm$^{-1}$ $^1$H-NMR (600 MHz in CDCl$_3$): δ=1.25-1.40 (2H, m), 1.43 (1H, m), 1.45-1.55 (3H, m), 1.91 (3H, dd), 2.23 (1H, m), 2.42 (1H, m), 2.55-2.70 (2H, m), 3.89 (1H, dd), 3.97 (1H, dd), 5.54 (1H, dq), 6.06 (1H, dq), 6.20 (1H, s)

$^{13}$C-NMR (150 MHz in CDCl$_3$): δ=18.12, 22.41, 23.55, 39.07, 40.28, 41.99, 43.92, 52.36, 68.79, 100.58, 125.49, 136.57, 166.71

Monomer Synthesis Example 3

Synthesis of 3-methyl-2-oxaspiro[4.5]decan-1-yl methacrylate

Monomer Synthesis Example 3-1

Synthesis of 3-methyl-2-oxaspiro[4.5]decan-1-ol

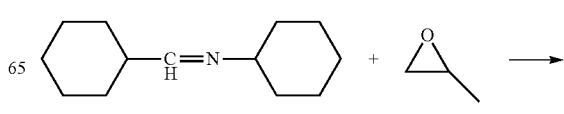

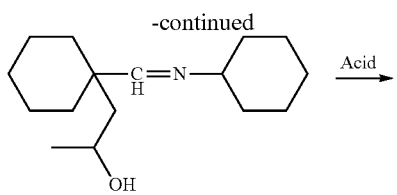

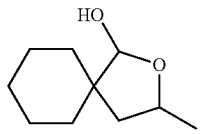

To a mixture of 40 g of ethylmagnesium bromide and 120 g of tetrahydrofuran was added a mixture of 50 g of cyclohexylmethylenecyclohexylamine and 50 g of tetrahydrofuran. The resulting mixture was stirred for 2 hours under tetrahydrofuran reflux conditions. Thereafter, 21 g of propylene oxide was added under ice cooling to the reaction mixture, which was stirred for a further 12 hours at room temperature. Then 30 g of acetic acid was added to quench the reaction, followed by ordinary aqueous workup, obtaining 74 g of a crude product, 1-[(1-cyclohexylimino-methyl)cyclohexyl]propan-2-ol. To 74 g of the crude product were added 16 g of acetic acid, 400 g of hexane, and 280 g of water. The mixture was stirred at 50° C. for 12 hours. The reaction mixture was then subjected to ordinary aqueous workup and distillation for purification, obtaining 28 g (yield 63%) of the target compound, 3-methyl-2-oxaspiro-[4.5]decan-1-ol.

3-methyl-2-oxaspiro[4.5]decan-1-ol colorless liquid
boiling point: 68° C./27 Pa
GC-MS (EI): (m/z)$^+$=29, 41, 55, 67, 82, 95, 109, 124, 137, 155, 169 [(M-H)$^+$]
IR of isomeric mixture (thin film): ν=3404, 2966, 2927, 2854, 1450, 1378, 1348, 1309, 1259, 1174, 1149, 1128, 1106, 1078, 1041, 1002, 919, 908, 879, 811 cm$^{-1}$
$^1$H-NMR (600 MHz in CDCl$_3$): δ=1.28 (3H, d, J=6.2 Hz), 1.30-1.58 (11H, m), 1.88-1.97 (1H, m), 3.34 (1H, s), 4.20 (1H, m), 4.97 (1H, s) ppm (peak assignment of main isomers)
$^{13}$C-NMR (150 MHz in CDCl$_3$): δ=21.87, 23.78, 26.39, 32.15, 33.47, 36.74, 42.33, 48.25, 74.88, 103.0 ppm (peak assignment of main isomers)

Monomer Synthesis Example 3-2

Synthesis of 3-methyl-2-oxaspiro[4.5]decan-1-yl acetate

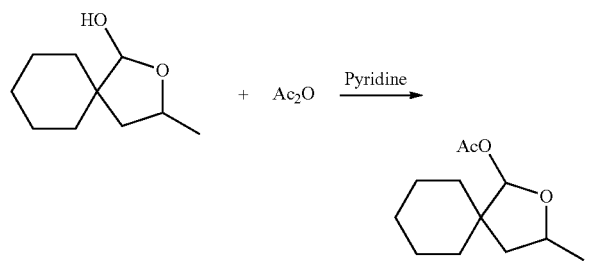

A mixture of 11 g of 3-methyl-2-oxaspiro[4.5]decan-1-ol, 7.7 g of pyridine and 9.2 g of acetic anhydride was heated at 50° C. for 12 hours. The reaction mixture was concentrated. The concentrate was purified by distillation, obtaining 13 g (yield 960) of the target compound, 3-methyl-2-oxaspiro[4.5]decan-1-yl acetate.

3-methyl-2-oxaspiro[4.5]decan-1-yl acetate

Colorless liquid
Boiling point: 74° C./17 Pa
GC-MS (EI): (m/z)$^+$=29, 43, 55, 67, 81, 95, 109, 124, 137, 153, 169, 211 [(M-H)$^+$]
IR of isomeric mixture (thin film): ν=2971, 2931, 2856, 1739, 1452, 1375, 1240, 1132, 1087, 1041, 1008, 989, 954, 927, 898, 881 cm$^{-1}$
$^1$H-NMR (600 MHz in CDCl$_3$): δ=1.24 (3H, d, J=6.2 Hz), 1.27-1.53 (11H, m), 1.91-1.94 (1H, m), 2.01 (3H, m), 4.25-4.30 (1H, m), 5.90 (1H, s) ppm (peak assignment of main isomers)
$^{13}$C-NMR (150 MHz in CDCl$_3$): δ=21.41, 22.58, 23.76, 25.90, 31.86, 33.08, 36.58, 41.77, 47.60, 75.40, 102.7, 170.8 ppm (peak assignment of main isomers)

Monomer Synthesis Example 3-3

Synthesis of 3-methyl-2-oxaspiro[4.5]decan-1-yl methacrylate

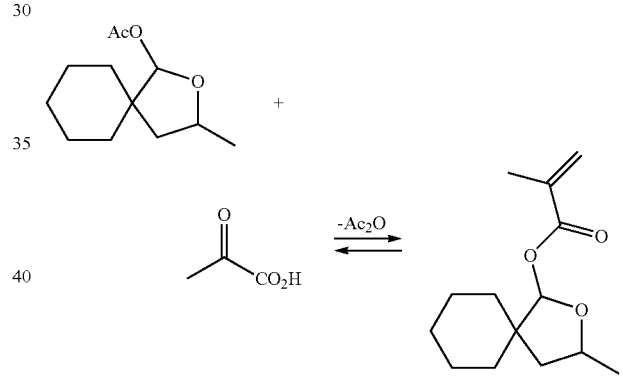

A mixture of 13 g of 3-methyl-2-oxaspiro[4.5]decan-1-yl acetate, 24 g of methacrylic acid, and 13 mg of 2,2'-methylenebis(6-t-butyl-p-cresol) was heated at 50° C. under atmospheric pressure for 30 minutes, after which under a reduced pressure of 0.20 kPa, the reaction mixture was heated for 18 hours for distilling off the acetic acid formed. The reaction mixture was purified by distillation, obtaining 11 g (yield 800) of the target compound, 3-methyl-2-oxaspiro[4.5]decan-1-yl methacrylate.

3-methyl-2-oxaspiro[4.5]decan-1-yl methacrylate colorless liquid
boiling point: 88° C./13 Pa
GC-MS (EI): (m/z)$^+$=29, 41, 55, 69, 81, 95, 109, 124, 137, 153, 169, 237 [(M-H)$^+$]
IR of isomeric mixture (thin film): ν=2971, 2929, 2856, 1720, 1637, 1452, 1402, 1378, 1351, 1319, 1295, 1278, 1226, 1164, 1130, 1083, 1052, 1039, 1006, 989, 954, 906, 892, 860, 846, 811 cm$^{-1}$
$^1$H-NMR (600 MHz in CDCl$_3$): δ=1.26 (3H, d, J=6.2 Hz), 1.28-1.56 (11H, m), 1.92 (3H, t, J=1.0, 1.4 Hz), 2.05 (1H, m), 4.29-4.37 (1H, m), 5.54 (1H, m), 5.98 (1H, s), 6.07 (1H, m) ppm (peak assignment of main isomers)

$^{13}$C-NMR (150 MHz in CDCl$_3$): δ=18.34, 22.52, 23.43, 23.63, 26.10, 31.97, 33.03, 41.96, 47.83, 76.20, 102.9, 125.6, 136.7, 166.7 ppm (peak assignment of main isomers)

Monomer Synthesis Example 4

Synthesis of 2-oxaspiro[5.5]undecan-1-yl methacrylate

Monomer Synthesis Example 4-1

Synthesis of 2-oxaspiro[5.5]undecan-1-ol

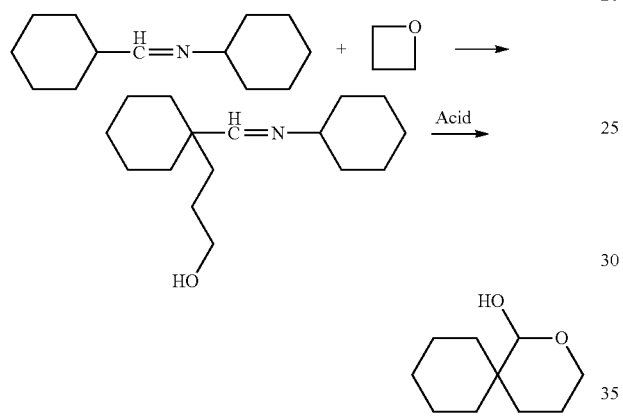

To a mixture of 44 g of ethylmagnesium bromide and 120 g of tetrahydrofuran was added a mixture of 50 g of cyclohexylmethylenecyclohexylamine and 50 g of tetrahydrofuran. The resulting mixture was stirred for 2 hours under tetrahydrofuran reflux conditions. Thereafter, 21 g of oxetane was added under ice cooling to the reaction mixture, which was stirred for a further 20 hours at room temperature. Then 30 g of acetic acid was added to quench the reaction, followed by ordinary aqueous workup, obtaining 67 g of a crude product, 1-[(1-cyclohexyliminomethyl)cyclo-hexyl]propan-1-ol. To 67 g of the crude product were added 16 g of acetic acid, 400 g of hexane, and 280 g of water. The mixture was stirred at 50° C. for 12 hours. The reaction mixture was then subjected to ordinary aqueous workup and distillation for purification, obtaining 22 g (yield 500) of the target compound, 2-oxaspiro[5.5]undecan-1-ol.

Monomer Synthesis Example 4-2

Synthesis of 2-oxaspiro[5.5]undecan-1-yl acetate

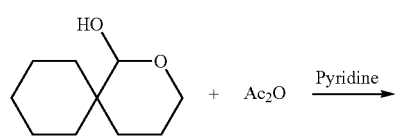

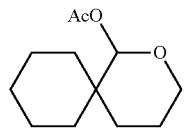

A mixture of 22 g of 2-oxaspiro[5.5]undecan-1-ol, 15 g of pyridine and 19 g of acetic anhydride was heated at 50° C. for 12 hours. The reaction mixture was concentrated. The concentrate was purified by distillation, obtaining 25 g (yield 91%) of the target compound, 2-oxaspiro[5.5]undecan-1-yl acetate.

Monomer Synthesis Example 4-3

Synthesis of 2-oxaspiro[5.5]undecan-1-yl methacrylate

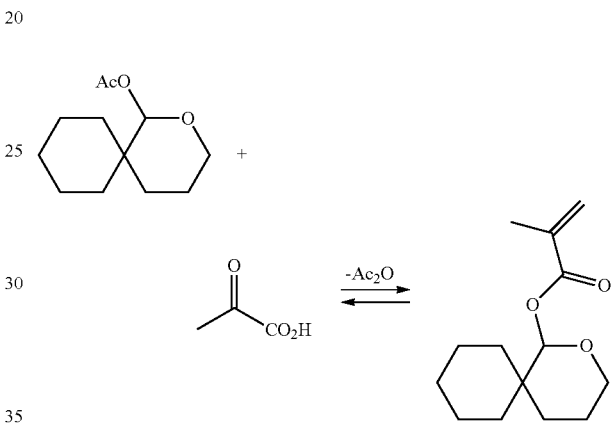

A mixture of 25 g of 2-oxaspiro[5.5]undecan-1-yl acetate, 50 g of methacrylic acid, and 25 mg of 2,2'-methylenebis(6-t-butyl-p-cresol) was heated at 50° C. under atmospheric pressure for 30 minutes, after which under a reduced pressure of 0.20 kPa, the reaction mixture was heated for 18 hours for distilling off the acetic acid formed. The reaction mixture was purified by distillation, obtaining 21 g (yield 74%) of the target compound, 2-oxaspiro[5.5]undecan-1-yl methacrylate.

Monomer Synthesis Example 5

Synthesis of 4-oxatricyclo[4.2.1.0$^{3,7}$]non-5-yl methacrylate

Monomer Synthesis Example 5-1

Synthesis of 4-oxatricyclo[4.2.1.0$^{3,7}$]non-5-yl acetate

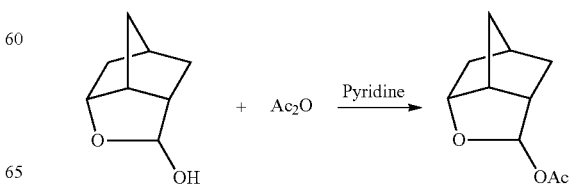

A mixture of 14 g of 4-oxatricyclo[4.2.1.0$^{3,7}$]nonan-5-ol, 12 g of pyridine and 14 g of acetic anhydride was heated at 50° C. for 5 hours. The reaction mixture was concentrated. The concentrate was purified by distillation, obtaining 16 g (yield 88%) of the target compound.

Monomer Synthesis Example 5-2

Synthesis of 4-oxatricyclo[4.2.1.0$^{3,7}$]non-5-yl methacrylate

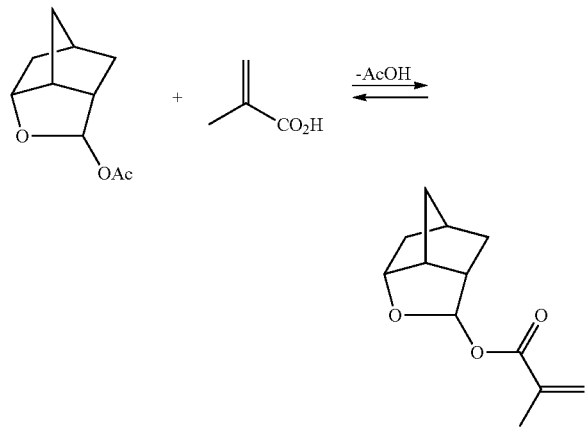

A mixture of 16 g of 4-oxatricyclo[4.2.1.0$^{3,7}$]non-5-yl acetate, 40 g of methacrylic acid, and 16 mg of 2,2'-methylenebis(6-t-butyl-p-cresol) was heated at 50° C. under atmospheric pressure for 30 minutes, after which under a reduced pressure of 0.20 kPa, the reaction mixture was heated for 18 hours for distilling off the acetic acid formed. The reaction mixture was purified by distillation, obtaining 17 g (yield 91%) of the target compound.

Polymer Synthesis Examples

Polymers were synthesized in accordance with the following formulation.

Polymer Synthesis Example 1

Synthesis of Polymer P-01

In a nitrogen blanket, a flask was charged with 8.19 g of 3-methyl-2-oxaspiro[4.5]decan-1-yl methacrylate, 5.07 g of 3-hydroxy-1-adamantyl methacrylate, 6.74 g of 4,8-dioxatricyclo[4.2.1.0$^{3,7}$]nonan-5-on-2-yl methacrylate, 989 mg of 2,2'-azobis(2-methylpropionic acid)dimethyl (MAIB), and 35.0 g of methyl ethyl ketone (MEK) to form a monomer solution. Another flask in a nitrogen blanket was charged with 11.7 g of MEK, which was heated up to 80° C. while stirring. The monomer solution was added dropwise to the hot MEK over 4 hours. After the completion of dropwise addition, the polymerization solution was continuously stirred for 2 hours while keeping the solution temperature at 80° C. The polymerization solution was cooled to room temperature and then added dropwise to 200 g of hexane, with vigorous stirring. The thus precipitated copolymer was filtered. The copolymer was washed twice with a solvent mixture of 22.7 g of MEK and 97.3 g of hexane, and vacuum dried at 50° C. for 20 hours, obtaining the copolymer in white powder form. The copolymer had a weight average molecular weight (Mw) of 9,000 as measured by gel permeation chromatography (GPC) versus polystyrene standards, and a dispersity (Mw/Mn) of 2.35.

Polymer Synthesis Examples 2 to 24

Synthesis of Polymers P-02 to P-24

Polymers P-02 to P-24 were synthesized by the same procedure as above or a well-known procedure.

Comparative Polymer Synthesis Examples 1 to 6

Synthesis of Polymers P-25 to P-30

Polymers P-25 to P-30 were synthesized by the same procedure as above or a well-known procedure.

Resist Preparation Examples

Resist compositions were formulated using the inventive and comparative polymers as a base resin and examined for resist properties.

Resist Preparation Examples 1 to 24 & Comparative Resist Preparation Examples 1 to 6

Resist compositions were prepared by dissolving the inventive polymers (P-01 to P-24), a photoacid generator (PAG), and a basic compound in a solvent in accordance with the formulation shown in Table 1. These compositions were filtered through a Teflon° filter with a pore diameter of 0.2 μm, thereby giving resist solutions (R-01 to R-24). In all runs, the solvent contained 0.01% by weight of surfactant KH-20 (Asahi Glass Co., Ltd.). Comparative resist compositions (R-25 to R-30) were similarly prepared in accordance with the formulation shown in Table 2.

TABLE 1

| Resist | Resin | PAG | Base | Solvent 1 | Solvent 2 |
|---|---|---|---|---|---|
| R-01 | P-01 (80) | PAG-1 (4.4) | Base-1 (0.94) | PGMEA (560) | CyHO (240) |
| R-02 | P-02 (80) | PAG-1 (4.4) | Base-1 (0.94) | PGMEA (560) | CyHO (240) |
| R-03 | P-03 (80) | PAG-1 (4.4) | Base-1 (0.94) | PGMEA (560) | CyHO (240) |
| R-04 | P-04 (80) | PAG-1 (4.4) | Base-1 (0.94) | PGMEA (560) | CyHO (240) |
| R-05 | P-05 (80) | PAG-1 (4.4) | Base-1 (0.94) | PGMEA (560) | CyHO (240) |
| R-06 | P-06 (80) | PAG-1 (4.4) | Base-1 (0.94) | PGMEA (560) | CyHO (240) |
| R-07 | P-07 (80) | PAG-1 (4.4) | Base-1 (0.94) | PGMEA (560) | CyHO (240) |
| R-08 | P-08 (80) | PAG-1 (4.4) | Base-1 (0.94) | PGMEA (560) | CyHO (240) |
| R-09 | P-09 (80) | PAG-1 (4.4) | Base-1 (0.94) | PGMEA (560) | CyHO (240) |
| R-10 | P-10 (80) | PAG-1 (4.4) | Base-1 (0.94) | PGMEA (560) | CyHO (240) |
| R-11 | P-11 (80) | PAG-1 (4.4) | Base-1 (0.94) | PGMEA (560) | CyHO (240) |
| R-12 | P-12 (80) | PAG-1 (4.4) | Base-1 (0.94) | PGMEA (560) | CyHO (240) |
| R-13 | P-13 (80) | PAG-1 (4.4) | Base-1 (0.94) | PGMEA (560) | CyHO (240) |

TABLE 1-continued

| Resist | Resin | PAG | Base | Solvent 1 | Solvent 2 |
|---|---|---|---|---|---|
| R-14 | P-14 (80) | PAG-1 (4.4) | Base-1 (0.94) | PGMEA (560) | CyHO (240) |
| R-15 | P-15 (80) | PAG-1 (4.4) | Base-1 (0.94) | PGMEA (560) | CyHO (240) |
| R-16 | P-16 (80) | PAG-1 (4.4) | Base-1 (0.94) | PGMEA (560) | CyHO (240) |
| R-17 | P-17 (80) | PAG-1 (4.4) | Base-1 (0.94) | PGMEA (560) | CyHO (240) |
| R-18 | P-18 (80) | PAG-1 (4.4) | Base-1 (0.94) | PGMEA (560) | CyHO (240) |
| R-19 | P-19 (80) | PAG-1 (4.4) | Base-1 (0.94) | PGMEA (560) | CyHO (240) |
| R-20 | P-20 (80) | PAG-1 (4.4) | Base-1 (0.94) | PGMEA (560) | CyHO (240) |
| R-21 | P-21 (80) | PAG-1 (4.4) | Base-1 (0.94) | PGMEA (560) | CyHO (240) |
| R-22 | P-22 (80) | PAG-1 (4.4) | Base-1 (0.94) | PGMEA (560) | CyHO (240) |
| R-23 | P-23 (80) | PAG-1 (4.4) | Base-1 (0.94) | PGMEA (560) | CyHO (240) |
| R-24 | P-24 (80) | PAG-1 (4.4) | Base-1 (0.94) | PGMEA (560) | CyHO (240) |

TABLE 2

| Resist | Resin | PAG | Base | Solvent 1 | Solvent 2 |
|---|---|---|---|---|---|
| R-25 | P-25 (80) | PAG-1 (4.4) | Base-1 (0.94) | PGMEA (560) | CyHO (240) |
| R-26 | P-26 (80) | PAG-1 (4.4) | Base-1 (0.94) | PGMEA (560) | CyHO (240) |
| R-27 | P-27 (80) | PAG-1 (4.4) | Base-1 (0.94) | PGMEA (560) | CyHO (240) |
| R-28 | P-28 (80) | PAG-1 (4.4) | Base-1 (0.94) | PGMEA (560) | CyHO (240) |
| R-29 | P-29 (80) | PAG-1 (4.4) | Base-1 (0.94) | PGMEA (560) | CyHO (240) |
| R-30 | P-30 (80) | PAG-1 (4.4) | Base-1 (0.94) | PGMEA (560) | CyHO (240) |

In Tables 1 and 2, the values in parentheses are in parts by weight. The acid generator, base and solvent are designated by abbreviations, which have the following meaning.

PAG-1: triphenylsulfonium nonafluorobutanesulfonate

Base-1: tri(2-methoxymethoxyethyl)amine

PGMEA: 1-methoxyisopropyl acetate

CyHO: cyclohexanone

The resins designated by abbreviations are polymers constructed as in Tables 3 to 6.

TABLE 3

| Resin | Unit 1 | Unit 2 | Unit 3 | Unit 4 | Mw |
|---|---|---|---|---|---|
| P-01 | A-1M (0.30) | B-1M (0.25) | B-2M (0.45) | | 7,200 |
| P-02 | A-1M (0.40) | B-1M (0.25) | B-2M (0.35) | | 7,600 |
| P-03 | A-2M (0.30) | B-1M (0.25) | B-2M (0.45) | | 6,500 |
| P-04 | A-2M (0.40) | B-1M (0.25) | B-2M (0.35) | | 7,800 |
| P-05 | A-3M (0.30) | B-1M (0.25) | B-2M (0.45) | | 7,500 |
| P-06 | A-3M (0.40) | B-1M (0.25) | B-2M (0.35) | | 6,600 |
| P-07 | A-4M (0.30) | B-1M (0.25) | B-2M (0.45) | | 6,800 |
| P-08 | A-4M (0.40) | B-1M (0.25) | B-2M (0.35) | | 6,300 |
| P-09 | A-4M (0.35) | B-1M (0.30) | B-2M (0.35) | | 6,200 |
| P-10 | A-1M (0.30) | A-5M (0.20) | B-1M (0.25) | B-2M (0.25) | 6,500 |
| P-11 | A-2M (0.30) | A-5M (0.20) | B-1M (0.25) | B-2M (0.25) | 7,700 |
| P-12 | A-3M (0.30) | A-5M (0.20) | B-1M (0.25) | B-2M (0.25) | 6,400 |
| P-13 | A-4M (0.30) | A-5M (0.20) | B-1M (0.25) | B-2M (0.25) | 6,200 |
| P-14 | A-1M (0.30) | A-6M (0.20) | B-1M (0.25) | B-2M (0.25) | 7,700 |
| P-15 | A-2M (0.30) | A-6M (0.20) | B-1M (0.25) | B-2M (0.25) | 7,800 |
| P-16 | A-3M (0.30) | A-6M (0.20) | B-1M (0.25) | B-2M (0.25) | 7,500 |
| P-17 | A-4M (0.30) | A-6M (0.20) | B-1M (0.25) | B-2M (0.25) | 6,000 |
| P-18 | A-1M (0.30) | B-1M (0.25) | B-2M (0.35) | B-6M (0.10) | 6,100 |
| P-19 | A-1M (0.30) | B-1M (0.25) | B-2M (0.35) | F-1M (0.10) | 6,300 |
| P-20 | A-1M (0.30) | B-1M (0.25) | B-2M (0.35) | F-2M (0.10) | 6,500 |
| P-21 | A-1M (0.25) | B-1M (0.25) | B-2M (0.35) | F-3M (0.10) | 6,200 |
| P-22 | A-1M (0.30) | B-1M (0.25) | B-3M (0.45) | | 6,400 |
| P-23 | A-1M (0.30) | B-1M (0.25) | B-4M (0.45) | | 6,000 |
| P-24 | A-12C (0.25) | A-13C (0.25) | A-14C (0.50) | | 6,000 |
| P-25 | A-6M (0.30) | B-1M (0.25) | B-2M (0.45) | | 6,000 |
| P-26 | A-7M (0.30) | B-1M (0.25) | B-2M (0.45) | | 6,000 |
| P-27 | A-8M (0.30) | B-1M (0.25) | B-2M (0.45) | | 6,000 |
| P-28 | A-9M (0.30) | B-1M (0.25) | B-2M (0.45) | | 6,000 |
| P-29 | A-10M (0.30) | B-1M (0.25) | B-2M (0.45) | | 6,000 |

TABLE 3-continued

| Resin | Unit 1 | Unit 2 | Unit 3 | Unit 4 | Mw |
|---|---|---|---|---|---|
| P-30 | A-11M (0.30) | B-1M (0.25) | B-2M (0.45) | | 6,000 |

The value in parentheses is an incorporation ratio of a particular unit expressed in molar ratio.

TABLE 4

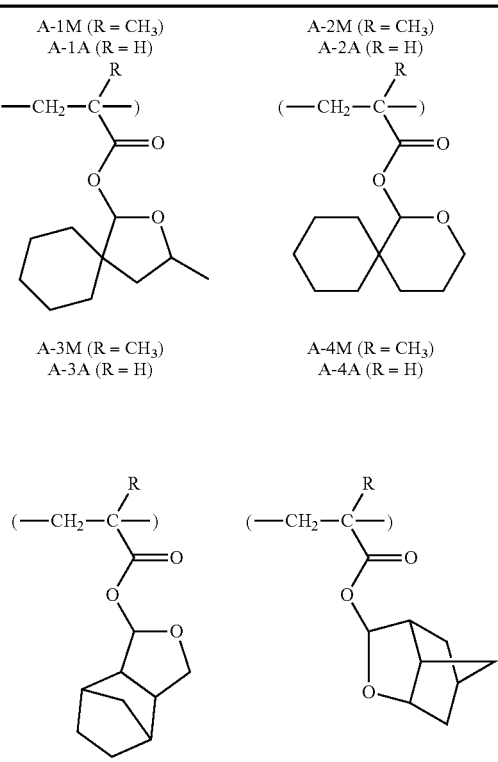

TABLE 4-continued

TABLE 4-continued

TABLE 5

TABLE 6

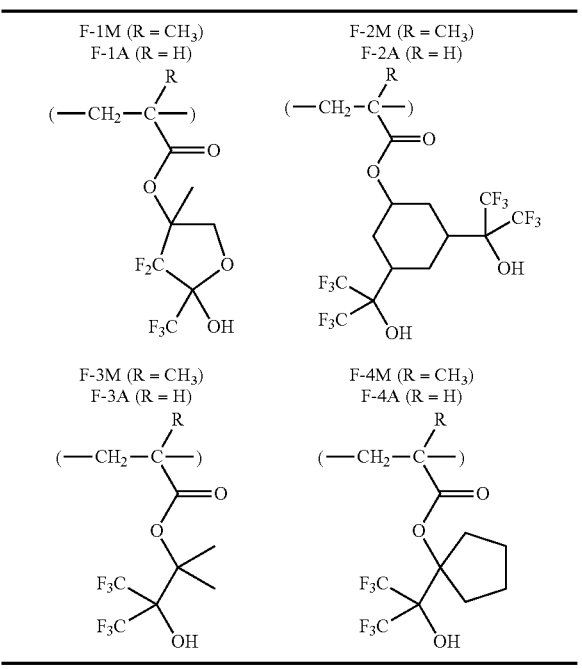

Examples 1 to 24

On silicon wafers having an antireflective coating (ARC29A, Nissan Chemical Industries Ltd.) of 78 nm thick, the resist solutions (R-01 to 24) of the invention were spin coated, then baked at 110° C. for 60 seconds to give resist films having a thickness of 170 nm. Using an ArF excimer laser stepper (Nikon Corp., NA 0.68), the resist films were exposed, baked (PEB) for 60 seconds and then puddle developed for 30 seconds with a 2.38 wt % aqueous solution of tetramethylammonium hydroxide. In this way, 1:1-line-and-space patterns were formed. The PEB step used an optimum temperature for a particular resist composition.

Test 1: Evaluation of Resolution

The pattern-bearing wafers were observed under a top-down scanning electron microscope (TDSEM). The optimum exposure was an exposure dose (mJ/cm$^2$) which provided a 1:1 resolution at the top and bottom of a 0.11-μm 1:1 line-and-space pattern. The maximum resolution of the resist was defined as the minimum line width (in increments of 0.01 μm) of a 1:1 line-and-space pattern that separated at the optimum exposure, with smaller values indicating better resolution.

Table 7 tabulates the test results (maximum resolution) of the resist compositions.

TABLE 7

| Test run | Resist | PEB temp. | Optimum exposure | Maximum resolution | Pattern profile |
|---|---|---|---|---|---|
| 1-1 | R-01 | 125° C. | 42.0 mJ/cm$^2$ | 0.09 μm | rectangular |
| 1-2 | R-02 | 125° C. | 39.0 mJ/cm$^2$ | 0.09 μm | rectangular |
| 1-3 | R-03 | 115° C. | 41.0 mJ/cm$^2$ | 0.09 μm | rectangular |
| 1-4 | R-04 | 110° C. | 42.0 mJ/cm$^2$ | 0.09 μm | rectangular |
| 1-5 | R-05 | 120° C. | 44.0 mJ/cm$^2$ | 0.09 μm | rectangular |
| 1-6 | R-06 | 110° C. | 45.0 mJ/cm$^2$ | 0.09 μm | rectangular |
| 1-7 | R-07 | 110° C. | 45.0 mJ/cm$^2$ | 0.10 μm | rectangular |
| 1-8 | R-08 | 115° C. | 42.0 mJ/cm$^2$ | 0.09 μm | rectangular |
| 1-9 | R-09 | 115° C. | 39.0 mJ/cm$^2$ | 0.09 μm | rectangular |
| 1-10 | R-10 | 120° C. | 43.0 mJ/cm$^2$ | 0.09 μm | rectangular |
| 1-11 | R-11 | 110° C. | 40.0 mJ/cm$^2$ | 0.09 μm | rectangular |
| 1-12 | R-12 | 110° C. | 38.0 mJ/cm$^2$ | 0.09 μm | rectangular |
| 1-13 | R-13 | 110° C. | 44.0 mJ/cm$^2$ | 0.09 μm | rectangular |
| 1-14 | R-14 | 110° C. | 41.0 mJ/cm$^2$ | 0.09 μm | rectangular |
| 1-15 | R-15 | 110° C. | 42.0 mJ/cm$^2$ | 0.09 μm | rectangular |
| 1-16 | R-16 | 110° C. | 37.0 mJ/cm$^2$ | 0.10 μm | rectangular |
| 1-17 | R-17 | 110° C. | 45.0 mJ/cm$^2$ | 0.09 μm | rectangular |
| 1-18 | R-18 | 110° C. | 44.0 mJ/cm$^2$ | 0.09 μm | rectangular |
| 1-19 | R-19 | 105° C. | 40.0 mJ/cm$^2$ | 0.09 μm | rectangular |
| 1-20 | R-20 | 110° C. | 42.0 mJ/cm$^2$ | 0.09 μm | rectangular |
| 1-21 | R-21 | 105° C. | 40.0 mJ/cm$^2$ | 0.09 μm | rectangular |
| 1-22 | R-22 | 110° C. | 41.0 mJ/cm$^2$ | 0.09 μm | rectangular |
| 1-23 | R-23 | 110° C. | 44.0 mJ/cm$^2$ | 0.09 μm | rectangular |
| 1-24 | R-24 | 120° C. | 45.0 mJ/cm$^2$ | 0.09 μm | rectangular |

The data of Table 7 demonstrate that the resist compositions within the scope of the invention have a high resolution.

Test 2: Evaluation of Outgassing

On silicon wafers having an antireflective coating (ARC29A, Nissan Chemical Industries Ltd.) of 78 nm thick, the resist solutions (R-01 to 24) of the invention and the comparative resist solutions (R-29 and R-30) were spin coated, then baked at 110° C. for 60 seconds to give resist films having a thickness of 170 nm. Using an ArF excimer laser scanner S305B (Nikon Corp., NA 0.60), the resist films were subjected to open-frame exposure at a stepwise varying exposure dose, after which the thickness of the film was measured. A percent film thickness reduction is calculated and recorded as [(initial thickness)−(thickness after exposure)]/(initial thickness).

Thereafter, the resist films were heated at 110° C. for 90 seconds, puddle developed for 30 seconds with a 2.38 wt % aqueous solution of tetramethylammonium hydroxide, washed with deionized water for 30 seconds, and spin dried. Herein, Eth is defined as the exposure dose at which the resist film is resolved to the bottom. A percent film thickness reduction resulting from an exposure dose which is 3 times Eth is an index of outgassing. A smaller value indicates a less quantity of outgas and hence, a better property. Tables 8 and 9 tabulate the test results of inventive and comparative resist compositions, respectively.

TABLE 8

| Test run | Resist | Outgas index (%) |
|---|---|---|
| 2-1 | R-01 | 2.1 |
| 2-2 | R-02 | 2.3 |
| 2-3 | R-03 | 1.7 |
| 2-4 | R-04 | 1.9 |
| 2-5 | R-05 | 1.5 |
| 2-6 | R-06 | 2.0 |
| 2-7 | R-07 | 2.0 |
| 2-8 | R-08 | 1.5 |
| 2-9 | R-09 | 2.1 |
| 2-10 | R-10 | 1.9 |
| 2-11 | R-11 | 2.2 |
| 2-12 | R-12 | 1.6 |
| 2-13 | R-13 | 1.8 |
| 2-14 | R-14 | 1.7 |
| 2-15 | R-15 | 2.1 |
| 2-16 | R-16 | 2.3 |
| 2-17 | R-17 | 2.5 |
| 2-18 | R-18 | 1.6 |
| 2-19 | R-19 | 1.7 |
| 2-20 | R-20 | 1.9 |
| 2-21 | R-21 | 1.5 |
| 2-22 | R-22 | 1.8 |
| 2-23 | R-23 | 2.0 |
| 2-24 | R-24 | 2.3 |

TABLE 9

| Test run | Resist | Outgas index (%) |
| --- | --- | --- |
| 2-25 | R-29 | 5.2 |
| 2-26 | R-30 | 9.8 |

It is demonstrated that the resist films using the resist compositions of the invention are minimized in outgassing.

Japanese Patent Application No. 2006-186298 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A polymer comprising at least recurring units derived from a polymerizable ester compound having any one of the following general formulae (1) to (4):

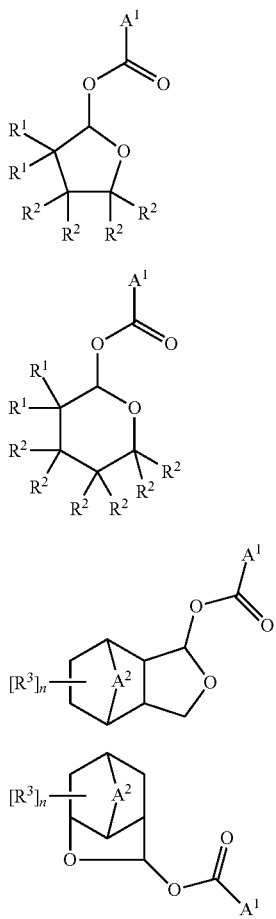

wherein $A^1$ is a polymerizable functional group having a carbon-carbon double bond, $A^2$ is an oxygen atom, methylene or ethylene group, $R^1$ is each independently a straight, branched to or cyclic monovalent hydrocarbon group of 1 to 10 carbon atoms, $R^2$ is each independently a hydrogen atom or a straight, branched or cyclic monovalent hydrocarbon group of 1 to 10 carbon atoms, or a combination of $R^1$, a combination of $R^2$, or a combination of $R^1$ and $R^2$ may bond together to form an aliphatic hydrocarbon ring with some carbon atoms in the oxygen heterocycle to which they are attached, and in that event, each of $R^1$ and $R^2$ is a straight, branched or cyclic alkylene group of 1 to 10 carbon atoms, $R^3$ is each independently a straight, branched or cyclic monovalent hydrocarbon group of 1 to 10 carbon atoms, or a combination of $R^3$ may bond together to form an aliphatic hydrocarbon ring with some carbon atoms in the ring to which they are attached, and in that event, each of $R^3$ is a straight, branched or cyclic alkylene group of 1 to 10 carbon atoms, and n is an integer of 0 to 6, and having a weight average molecular weight of 2,000 to 100,000.

2. The polymer of claim 1, further comprising recurring units of at least one type selected from the following general formula (R1):

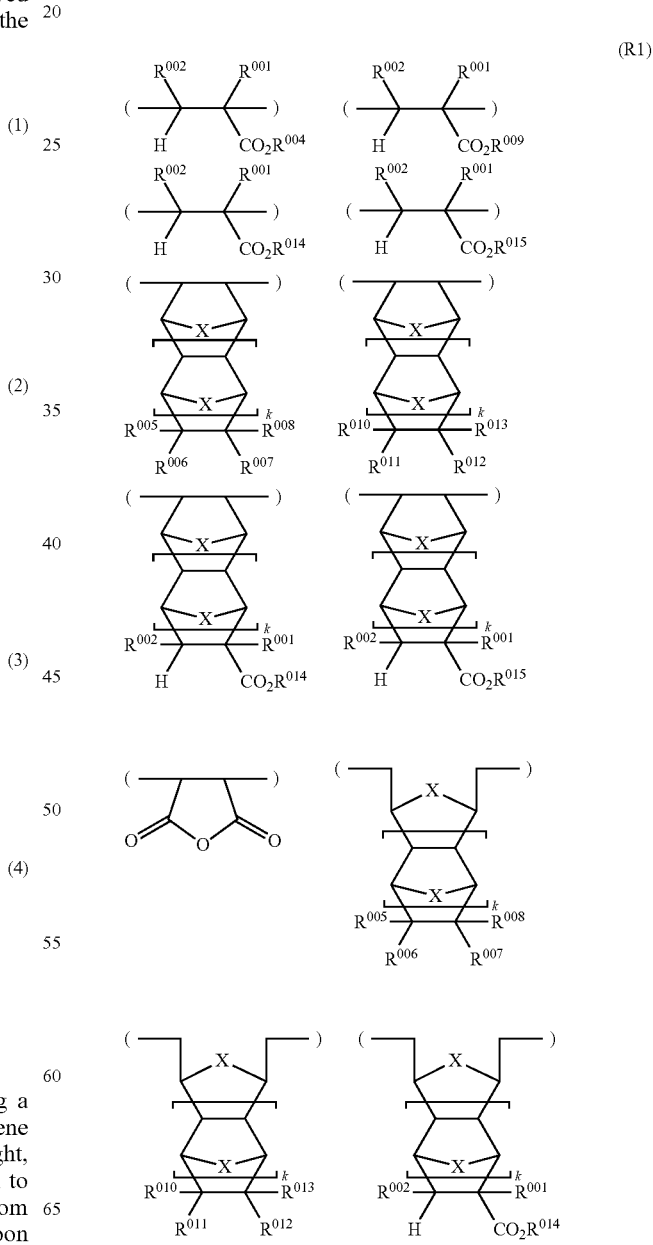

-continued

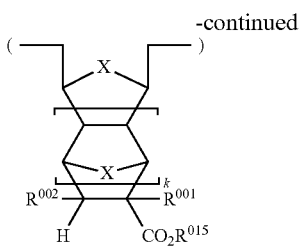

wherein $R^{001}$ is hydrogen, fluorine, methyl, trifluoromethyl or $CH_2CO_2R^{003}$, $R^{002}$ is hydrogen, methyl or $CO_2R^{003}$, $R^{003}$ is a straight, branched or cyclic $C_1$-$C_{15}$ alkyl group, $R^{004}$ is hydrogen or a monovalent hydrocarbon group of 1 to 15 carbon atoms having at least one group selected from among fluorinated substituent groups, carboxyl, hydroxyl and cyano groups, at least one of $R^{005}$ to $R^{008}$ is a carboxyl group or a monovalent hydrocarbon group of 1 to 15 carbon atoms having at least one group selected from among fluorinated substituent groups, carboxyl, hydroxyl and cyano groups while the remaining of $R^{005}$ to $R^{008}$ are each independently hydrogen or straight, branched or cyclic $C_1$-$C_{15}$ alkyl groups, or two of $R^{005}$ to $R^{008}$ may bond together to form an aliphatic hydrocarbon ring with the carbon atom(s) to which they are attached, and in that event, at least one of $R^{005}$ to $R^{008}$ is a divalent hydrocarbon group of 1 to 15 carbon atoms having at least one group selected from fluorinated substituent groups, carboxyl, hydroxyl and cyano groups while the remaining of $R^{005}$ to $R^{008}$ are each independently single bonds, hydrogen atoms or straight, branched or cyclic $C_1$-$C_{15}$ alkyl groups;

$R^{009}$ is a monovalent hydrocarbon group of 3 to 15 carbon atoms containing a —$CO_2$— partial structure, at least one of $R^{010}$ to $R^{013}$ is a monovalent hydrocarbon group of 2 to 15 carbon atoms containing a —$CO_2$— partial structure while the remaining of $R^{010}$ to $R^{013}$ are each independently hydrogen atoms or straight, branched or cyclic $C_1$-$C_{15}$ alkyl groups, or two of $R^{010}$ to $R^{013}$ may bond together to form an aliphatic hydrocarbon ring with the carbon atom(s) to which they are attached, and in that event, at least one of $R^{010}$ to $R^{013}$ is a divalent hydrocarbon group of 1 to 15 carbon atoms having a —$CO_2$— partial structure while the remaining of $R^{010}$ to $R^{013}$ are each independently single bonds, hydrogen atoms or straight, branched or cyclic $C_1$-$C_{15}$ alkyl groups;

$R^{014}$ is a polycyclic hydrocarbon group having 7 to 15 carbon atoms or an alkyl group containing such a polycyclic hydrocarbon group, $R^{015}$ is an acid labile group, X is $CH_2$ or an oxygen atom, and k is 0 or 1.

3. The polymer of claim 1, comprising recurring units derived from the polymerizable ester compound of any one of formulae (1) to (4) in a molar fraction of at least 5%.

4. A resist composition comprising the polymer of claim 1.

5. A resist composition comprising (A) the polymer of claim 1, (B) an acid generator, and (C) an organic solvent.

6. A resist composition comprising (A) the polymer of claim 1, (B) an acid generator, (C) an organic solvent, and (D) a sensitivity regulator.

7. A process for forming a pattern, comprising the steps of applying the resist composition of claim 4 onto a substrate to form a resist coating; heat treating the coating and exposing to high-energy radiation or electron beam through a photomask; and optionally heat treating the exposed coating and developing with a developer.

* * * * *